US009187769B1

(12) United States Patent
Medoff

(10) Patent No.: US 9,187,769 B1
(45) Date of Patent: *Nov. 17, 2015

(54) PROCESSING BIOMASS

(71) Applicant: XYLECO, INC., Woburn, MA (US)

(72) Inventor: Marshall Medoff, Brookline, MA (US)

(73) Assignee: XYLECO, INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/810,158

(22) Filed: Jul. 27, 2015

Related U.S. Application Data

(63) Continuation of application No. 14/704,733, filed on May 5, 2015, now Pat. No. 9,132,407, which is a continuation of application No. 14/580,100, filed on Dec. 22, 2014, now Pat. No. 9,062,328, which is a continuation of application No. 14/215,105, filed on Mar. 17, 2014, now Pat. No. 8,946,489, which is a continuation of application No. 13/656,892, filed on Oct. 22, 2012, now Pat. No. 8,716,537, which is a continuation of application No. 12/719,776, filed on Mar. 8, 2010, now Pat. No. 8,497,366, which is a continuation of application No. 12/417,880, filed on Apr. 3, 2009, now Pat. No. 8,212,087.

(60) Provisional application No. 61/049,404, filed on Apr. 30, 2008, provisional application No. 61/049,413, filed on Apr. 30, 2008, provisional application No. 61/049,415, filed on Apr. 30, 2008, provisional application No. 61/049,419, filed on Apr. 30, 2008, provisional application No. 61/073,496, filed on Jun. 18, 2008.

(51) Int. Cl.
*C07C 27/04* (2006.01)
*C07C 27/00* (2006.01)
*C12P 7/10* (2006.01)
*C12P 19/14* (2006.01)
*C12P 19/02* (2006.01)
*B01J 19/08* (2006.01)

(52) U.S. Cl.
CPC ............... *C12P 7/10* (2013.01); *B01J 19/085* (2013.01); *C07C 27/04* (2013.01); *C12P 19/02* (2013.01); *C12P 19/14* (2013.01); *B01J 2219/08* (2013.01); *C07C 27/00* (2013.01); *C12P 2201/00* (2013.01)

(58) Field of Classification Search
CPC ................................. C07C 27/04; C07C 27/00
USPC ............. 568/878, 880, 902, 903; 204/157.63, 204/257.15
See application file for complete search history.

(56) References Cited

U.S. PATENT DOCUMENTS

| 2,081,130 | A | 5/1937 | Atwell |
| 3,189,460 | A | 6/1965 | Smith |
| 3,352,773 | A | 11/1967 | Schwartz et al. |
| 3,483,005 | A | 12/1969 | Urbain et al. |
| 3,522,091 | A | 7/1970 | Lapidot et al. |
| 3,596,840 | A | 8/1971 | Blomqvist et al. |
| 3,962,054 | A | 6/1976 | Wattiez et al. |
| 4,304,649 | A | 12/1981 | Han et al. |
| 4,324,642 | A | 4/1982 | Durai-Swamy |
| 4,486,585 | A | 12/1984 | Turunen et al. |
| 4,769,082 | A | 9/1988 | Kumakura et al. |
| 5,100,791 | A | 3/1992 | Spindler et al. |
| 5,196,069 | A | 3/1993 | Cullingford et al. |
| 5,242,435 | A | 9/1993 | Murji et al. |
| 5,322,778 | A | 6/1994 | Antrim et al. |
| 5,458,897 | A | 10/1995 | Pare |
| 5,541,236 | A | 7/1996 | DeNicola et al. |
| 6,096,379 | A | 8/2000 | Eckhoff |
| 6,768,042 | B2 | 7/2004 | Yanofsky et al. |
| 7,118,852 | B2 | 10/2006 | Purdum |
| 7,166,650 | B2 | 1/2007 | Muratoglu et al. |
| 7,267,744 | B2 | 9/2007 | Graveson et al. |
| 2004/0129394 | A1 | 7/2004 | Graveson et al. |
| 2004/0171712 | A1 | 9/2004 | Ojeda et al. |
| 2007/0197679 | A1 | 8/2007 | Bellare et al. |
| 2008/0067724 | A1 | 3/2008 | Muratoglu et al. |
| 2008/0078122 | A1 | 4/2008 | Clark |
| 2008/0313954 | A1 | 12/2008 | Lee et al. |
| 2009/0170153 | A1 | 7/2009 | Stuart |
| 2009/0246253 | A1 | 10/2009 | Ding |

OTHER PUBLICATIONS

Rudraraju et al., "Sterilization of Confectioner's Sugar by Gamma Irradiation", AAPS Pharm. Sci., 1999, S1:11.
Taherzadeh et al., "Pretreatment of Lignocellulosic Wastes to Improve Ethanol and Biogas Production: A Review", Int. J. Mol. Sci., vol. 9, 2008, pp. 1621-1651.
DeKerf et al., "Characterization and Disintegration Properties of Irradiated Starch," Int. J. Pharmaceutics, vol. 221, 2001, pp. 69-76.
Mosier et al., "Features of Promising Technologies of Pretreatment of Lignocellulosic Biomass," Bioresource Technol., vol. 96, 2005, pp. 673-686.
Mullins et al., "Enzymatic Hydrolysis and Fermentation of Corn for Fuel Alcohol," Biotechnol. Bioeng., vol. 27, 2004, pp. 321-326.
Nemtanu et al., "Electron Beam Technology for Modifying the Functional Properties of Maize Starch," Nucl. Instrum. Meth. A, vol. 580, 2007, pp. 795-798.
Reinhard et al., "Effect of X-Radiation on Crystalline and Dissolved Sucrose," Radiology, vol. 12, 1929, pp. 151-153.
Wach et al., "Radiation Crosslinking of Carboxymethylcellulose of Various Degree of Substitution at High Concentration in Aqueous Solutions of Natural pH," Radiat. Phys. Chem., vol. 68, 2003, pp. 771-779.

(Continued)

*Primary Examiner* — Elvis O Price
(74) *Attorney, Agent, or Firm* — Leber Patent Law P.C.

(57) ABSTRACT

Biomass (e.g., plant biomass, animal biomass, and municipal waste biomass) is processed to produce useful products, such as fuels. For example, systems can use feedstock materials, such as cellulosic and/or lignocellulosic materials and/or starchy or sugary materials, to produce ethanol and/or butanol, e.g., by fermentation.

18 Claims, 39 Drawing Sheets

(56) References Cited

OTHER PUBLICATIONS

Saeman et al., "Effect of High-Energy Cathode Rays on Cellulose," Ind. Eng. Chem. vol. 44, 1952, pp. 2848-2852.
Sears et al., "Feasibility of Using Ultrasonic Irradiation to Recover Active Biomass from Waste Activated Sludge," J. Biotechnol. vol. 119, pp. 389-399.
Seymour et al., Polymer Chemistry, Third ed. Chapter 9, 1992, p. 288.
Smith et al., "Irradiation Enhancement of Biomass Conversion", Radiat. Phys. Chem., vol. 25, 1985, pp. 27-33.
Sun et al., "Hydrolysis of Lignocellulosic Materials for Ethanol Production: A Review," Bioresource Technol., vol. 83, 2002, pp. 1-11.
Goldemberg, "Ethanol for a Sustainable Energy Future," Science, vol. 31, 2007, pp. 808-810.
Takacs et al., "Effect of Gamma Radiation on Cotton Cellulose," Radiat. Phys. Chem., vol. 55, 1999, pp. 663-666.
Tolan, "Iogen's Process for Producing Ethanol from Cellulosic Biomass," Clean Techn. Environ. Policy, vol. 3, 2002, pp. 339-345.
Usmanov et al., "Change in Certain Properties of Cellulose During Gamma-Irradiation and Storage," Vysokomol. Soyed. A&B, vol. 1, 1980, pp. 77-82.
Vitti et al., "Irradiation (of) Fibrous Residues with Electron Beams Effect on Chemical Composition and Digestability", Sci. Agric., vol. 55, 1998, p. 151 (English).
Vitti et al., "Irradiation (of) Fibrous Residues with Electron Beams Effect on Chemical Composition and Digestibility", Sci. Agric., vol. 55, 1998, p. 151 (Portuguese).
Images—Scientific Instruments, "Radiation—Units of Measurement (Conventional or SI)," Web Page www.imagesco.com/articles/dmad/digital-meter-adapter-pg2.html, Jan. 26, 2011.
Wasik et al., "Free Radicals in Flour, Starch, and Gluten Produced by Ball-Milling, Electric Discharge, and Gamma-Irradiation," Cereal Chem. vol. 50, 1973, pp. 654-660.
Dziedziela et al., "Functional Groups in Gamma-Irradiated Cellulose," Radiat. Phys. Chem., vol. 23, 1984, pp. 723-725.
Ershov et al., "Radiation-Chemical Degradation of Cellulose and Other Polysaccharides," Russ. Chem. Rev., vol. 67, 1998, pp. 315-334.
Farkas, "Radiation Decontamination of Dry Food Ingredients and Processing Aids," J. Food Eng. vol. 3, 1984, pp. 245-264.
Generalova et al., "The Optical Properties of Solid Carbohydrates Irradiated with Gamma Radiation", Zhurnal Prikladnoi Spektroskopii, vol. 5, 1966, pp. 81-83.
Lepifre et al., "Lignin Incorporation Combined with Electron-Beam Irradiation Improves the Surface Water Resistance of Starch Films", Biomacromolecules, vol. 5, 2004, pp. 1678-1686.
Gruenewald, "Electron Irradiation of Dry Food Products", Radiat. Phys. Chem., vol. 22, 1983, pp. 733-741.
Han et al., "Gamma-Ray-Induced Degradation of Lignocellulosic Materials," Biotechnol. Bioeng. vol. 23, 1981, pp. 2525-2535.
Henderson et al., "ESR Study of the Effects of Water, Methanol, and Ethanol on Gamma-Irradiation of Starch,", J. Polym. Sci., vol. 19, 1981, pp. 1721-1732.
Han et al., "Effect of Gamma-Ray Irradiation on Alcohol Production from Corn," Biotechnol. Bioeng. vol. 25, 1983, pp. 2631-2640 (Abstract).
IBA Industrial, "E-Beam Technology," Web Page, www.iba-industrial.com/e-beam-x-ray/e-beam; Feb. 28, 2013.
Mishina et al., "Physical and Chromatographic Observations on Gamma-Irradiated Potato-Starch Granules," Nature, vol. 184 (Supp. 24), 1959, 1867 (Abstract).
Jianquin et al., "Pre-Irradiation Grafting of Temperature Sensitive Hydrogel on Cotton Cellulose Fabric," Radiat. Phys. Chem., vol. 55, 1999, pp. 55-59.
Junior et al., "Sucrose Fermentation by Brazilian Ethanol Production Yeasts in Media Containing Structurally Complex Nitrogen Sources," J. Inst. Brewing, vol. 115, 2009, pp. 191-197.
Krishna et al., "Optimization of Simultaneous Saccharification and Fermentation for the Production of Ethanol from Lignocellulosic Biomass," J. Agric. Food. Chem., vol. 48, 2000, pp. 1971-1976.
Kumakura et al., "Effect of Radiation Pretreatment of Bagasse on Enzymatic and Acid Hydrolysis," Biomass, vol. 3, 1983, pp. 199-208.
Kumakura et al., "Effect of Electron Beam Current on Radiation Pretreatment of Cellulosic Wastes with Electron Beam Accelerator," Radiat. Phys. Chem., vol. 23, 1984, pp. 523-527.
Berger et al., "Volatile Compounds Formed During Gamma Irradiation of Corn Starch," Staerke, vol. 26, 1974, pp. 185-189 (Abstract).
Buchard et al., "The Effects of Ionizing Radiation on the Cellulose of Woodfree Paper," Cellulose, vol. 13, 2006, pp. 601-610.
Lindeman et al., "Ethanol in Brazil: Brief Summary of the State of Industry in 1977," Biotechnol. Bioeng., vol. 21, 1979, pp. 1107-1119.
Mazzei et al., "Radiation Grafting Studies of Acrylic Acid Onto Cellulose Triacetate Membranes," Radiat. Phys. Chem., vol. 64, 2002, pp. 149-160.
McMillan, "Processes for Pretreating Lignocellulosic Biomass: A Review," NREL/TP-421-4978, 1992.
Meyer et al., "Fermentation Using Different Kinds of Sugar", 2010.
Awafo et al., "Effect of Irradiation as a Pretreatment, on Bioconversion of Corn Stover into Protein-Rich Mycelial Biomass of Pleurotus sajor-caju.", Radiat. Phys. Chem. vol. 46, 1995, pp. 1299-1302.
Bartolotta et al., "ESR Solid State Dosimetry: Behaviours of Various Amino Acids and Blend Preparation Procedures", Rad. Prot. Dosimetry, vol. 84, 1999, pp. 293-296.
Baugh et al., "Electron Spin Resonance Study of Gamma-Irradiated Carbohydrate Ices at Low Temperatures," Nature, vol. 221, 1969, pp. 1138-1139.
Beardmore et al., "Gamma-Ray Irradiation as Pretreatment for the Enzymatic Hydrolysis of Cellulose," Biotechnol. Lett., vol. 2, 1980, pp. 435-438.

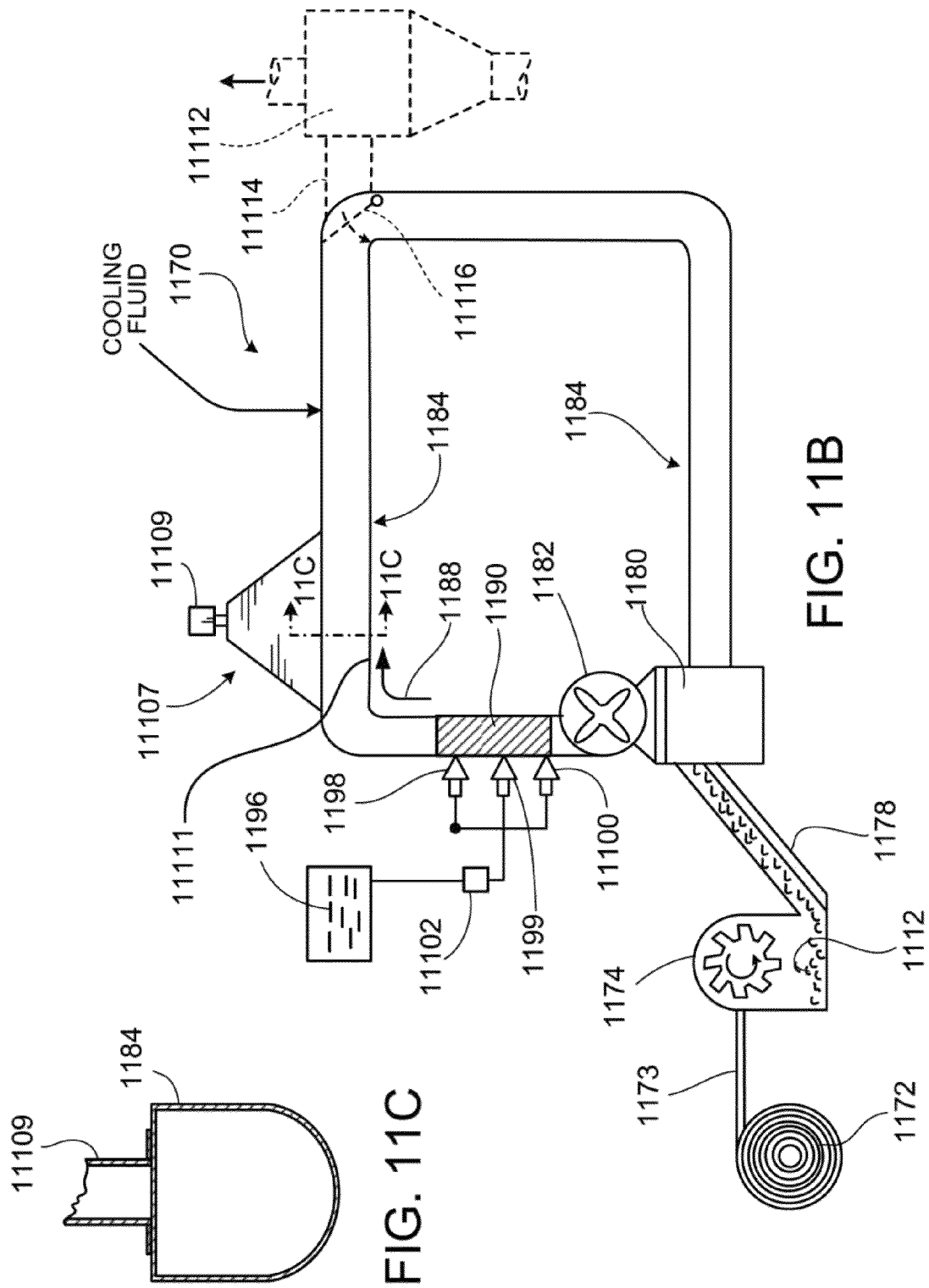

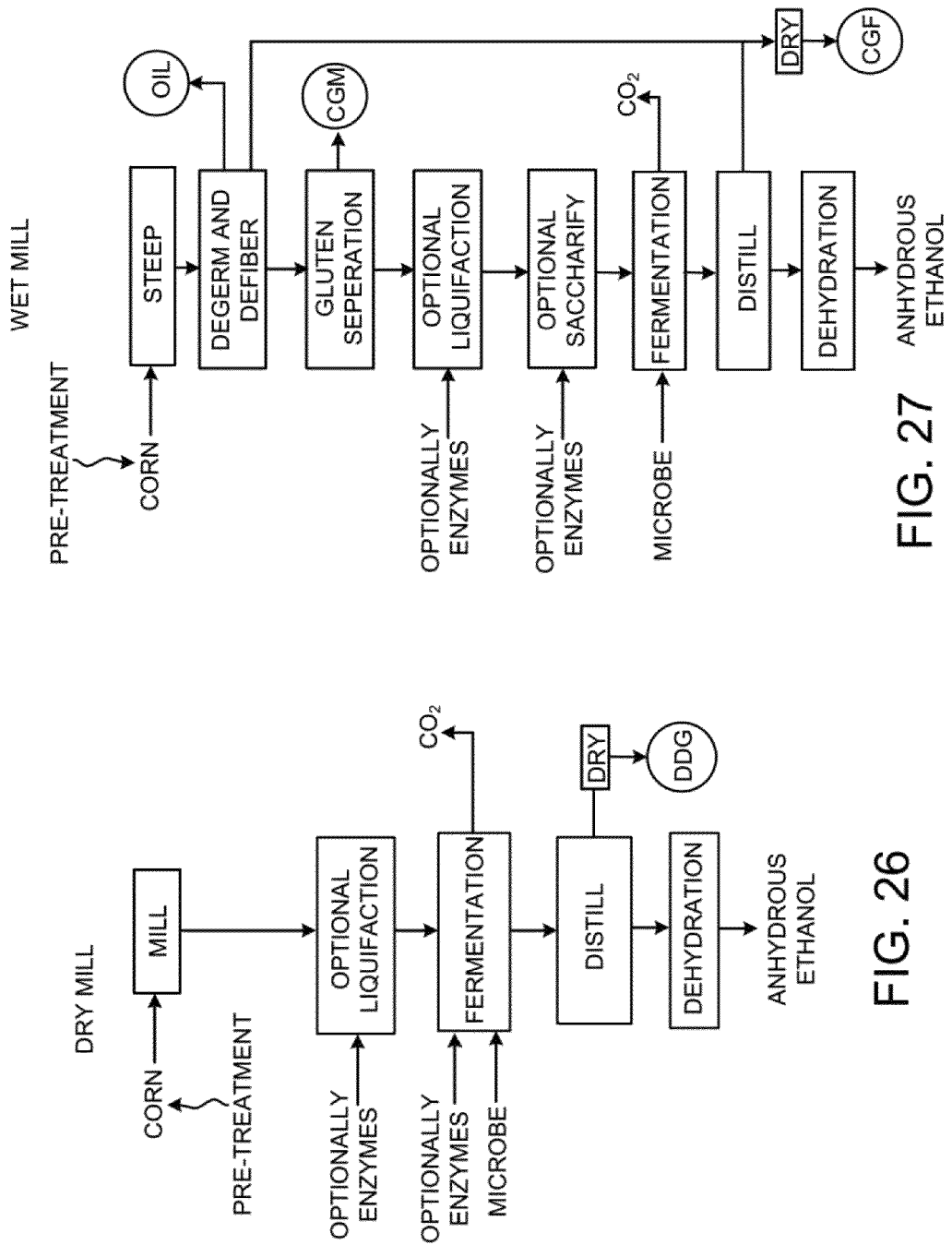

PROCESSING BIOMASS

RELATED APPLICATIONS

This application is a continuation of pending U.S. application Ser. No. 14/704,733, filed May 5, 2015, which is a continuation of U.S. application Ser. No. 14/580,100, filed Dec. 22, 2014, now U.S. Pat. No. 9,062,328, issued on Jun. 23, 2015, which is a continuation of U.S. application Ser. No. 14/215,105, filed Mar. 17, 2014, now U.S. Pat. No. 8,946,489, issued on Feb. 3, 2015, which is a continuation of U.S. application Ser. No. 13/656,892, filed Oct. 22, 2012, now U.S. Pat. No. 8,716,537, issued on May 6, 2014, which is a continuation of U.S. application Ser. No. 12/719,776, filed Mar. 8, 2010, now U.S. Pat. No. 8,497,366, issued on Jul. 30, 2013, which is a continuation of U.S. application Ser. No. 12/417,880, filed Apr. 3, 2009, now U.S. Pat. No. 8,212,087, issued on Jul. 3, 2012, which claims benefit of U.S. provisional App. Nos. 61/049,404, filed Apr. 30, 2008, 61/049,413, filed Apr. 30, 2008, 61/049,415, filed Apr. 30, 2008, 61/049,419, filed Apr. 30, 2008, and 61/073,496, filed Jun. 18, 2008. The entire contents of all of these applications are incorporated by reference herein.

TECHNICAL FIELD

This invention relates to processing biomass, such as methods and systems for processing biomass.

BACKGROUND

Various carbohydrates, such as cellulosic and lignocellulosic materials, e.g., in fibrous form, are produced, processed, and used in large quantities in a number of applications. Often such materials are used once, and then discarded as waste, or are simply considered to be waste materials, e.g., sewage, bagasse, sawdust, and stover.

SUMMARY

Biomass can be processed to alter its structure at one or more levels. The processed biomass can then be used, for example as a source of materials and/or fuel.

In general, the invention pertains to methods of changing a molecular and/or a supramolecular structure of a biomass feedstock. As will be discussed below, in some implementations, the methods include irradiating and quenching the biomass feedstock. In other implementations, the methods include irradiating the feedstock, cooling the feedstock, and again irradiating the feedstock.

Carbohydrate-containing materials (e.g., biomass materials or biomass-derived materials, such as starchy materials, cellulosic materials, lignocellulosic materials, or biomass materials) that are or that include significant amounts of low molecular weight sugars (e.g., monosaccharides, disaccharides, or trisaccharides), can be processed to change their structure, and products can be made from the structurally changed materials. For example, many of the methods described herein can provide cellulosic and/or lignocellulosic materials that have a lower molecular weight and/or crystallinity relative to a native material. Many of the methods provide materials that can be more readily utilized by a variety of microorganisms to produce useful products, such as hydrogen, alcohols (e.g., ethanol or butanol), organic acids (e.g., acetic acid), hydrocarbons, co-products (e.g., proteins) or mixtures of any of these. Many of the products obtained, such as ethanol or n-butanol, can be utilized as a fuel for powering cars, trucks, tractors, ships or trains, e.g., as an internal combustion fuel or as a fuel cell feedstock. Many of the products obtained can also be utilized to power aircraft, such as planes, e.g., having jet engines or helicopters. In addition, the products described herein can be utilized for electrical power generation, e.g., in a conventional steam generating plant or in a fuel cell plant.

In one aspect, the invention features methods that include quenching a biomass feedstock that has been irradiated to ionize the biomass feedstock so that the feedstock has a first level of radicals which are detectable with an electron spin resonance spectrometer, to an extent that the radicals are at a second level lower than the first level. Some methods further include processing the irradiated and quenched biomass feedstock to produce a product.

Some implementations include one or more of the following features.

Quenching can include quenching the radicals to a level that is no longer detectable with the electron spin resonance spectrometer, e.g., less than about $10^{14}$ spins. Quenching can include applying pressure to the biomass, e.g., a pressure of greater than about 1000 psi. Pressure can be applied together with the application of heat. Quenching can include contacting the biomass with a gas capable of reacting with the radicals, e.g., contacting the biomass with a fluid capable of penetrating into the biomass and reacting with the radicals. Quenching can also, or alternatively, include contacting the biomass with an antioxidant. In some cases, the biomass feedstock includes an antioxidant dispersed therein, and quenching includes contacting the antioxidant dispersed in the biomass feedstock with the radicals.

In another aspect, the invention features a method including irradiating a biomass feedstock that has been prepared by reducing one or more dimensions of individual pieces of the biomass feedstock, using an apparatus comprising an accelerator configured to accelerate particles, such as electrons or ions, wherein the apparatus is capable of processing greater than 1,000 tons of biomass material per year, e.g., greater than 10,000, 25,000, 50,000, 100,000, or even greater than 1,000,000 tons of biomass per year.

In a further aspect, the invention features irradiating a biomass feedstock, e.g., with ionizing radiation of electrons or ions, to change a molecular and/or supramolecular structure of the biomass feedstock, cooling the biomass feedstock, and then re-irradiating the biomass feedstock. The two applications of radiation can be the same or different, e.g., the same kind, such as electrons at the same level.

The invention also features products formed by these methods, and systems for performing the methods.

Some implementations of these methods include one or more of the following features.

The biomass feedstock can be cooled to an extent that after cooling, the biomass is at a temperature below its initial temperature prior to irradiation. Cooling of the biomass can include contacting the biomass with a fluid at a temperature below the initial temperature of the biomass or below the temperature of the biomass after irradiation.

Each irradiation of the biomass feedstock can be performed as the biomass feedstock is being pneumatically conveyed in a fluid. Radiation can be applied as the biomass feedstock falls under the influence of gravity. For example, the biomass can be conveyed from a first belt at a first height and captured by a second belt at a second level, lower than the first level, the trailing edge of the first belt and the leading edge of the second belt defining a gap, and ionizing radiation can be applied to the biomass feedstock in the defined gap. During irradiation the biomass can be conveyed past a particle gun and through a beam of charged particles. The biomass feedstock may have a bulk density of less than about 0.25 g/cm$^3$ in a region under and/or above the beam.

In another aspect, the invention features methods of changing a molecular structure and/or a supramolecular structure of a starchy material or of a low molecular weight sugar, such as sucrose, in a biomass feedstock comprising at least about 10 percent by weight of the low molecular weight sugar. The methods include processing a treated biomass feedstock to produce a product, the treated biomass feedstock having been prepared by pretreating a biomass feedstock using a pretreatment method that changes the molecular structure and/or supramolecular structure of the starchy material or of the low molecular weight sugar portion, selected from radiation, sonication, pyrolysis, and oxidation.

Any of the above aspects of the invention can, in some implementations, include one or more of the following features.

The method can further include treating the biomass feedstock with one or more other pretreatment methods, wherein the other pretreatment methods are selected from sonication, pyrolysis, and oxidation.

Radiation can be in the form of an electron beam, which can be applied, for example, at a total dosage of between about 10 MRad and about 50 MRad. The radiation can be ionizing radiation.

Processing can include making a combustible fuel. In some cases, processing includes converting the irradiated material utilizing a microorganism having the ability to convert at least about 1 percent by weight of the biomass to the fuel.

In some implementations, processing comprises fermenting the feedstock, aerobically or anaerobically, to produce a product such as a fuel, e.g., ethanol. For example, processing may comprise contacting the feedstock with a microorganism having the ability to convert at least a portion, e.g., at least about 1 percent by weight, of the feedstock to the product. The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures may be utilized.

The product can include one or more of hydrogen, organic acids, proteins, hydrocarbons, and alcohols, e.g., ethanol, n-propanol, isopropanol, n-butanol, and mixtures thereof. Other examples of products that may be produced by the methods disclosed herein include mono- and polyfunctional C1-C6 alkyl alcohols, mono- and poly-functional carboxylic acids, C1-C6 hydrocarbons, and combinations thereof. Other examples of alcohols include methanol, ethylene glycol, propylene glycol, 1,4-butane diol, glycerin, and combinations thereof. Carboxylic acids include formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid, γ-hydroxybutyric acid, and combinations thereof. Hydrocarbons include methane, ethane, propane, pentane, n-hexane, and combinations thereof. Many of these products may be used as fuels.

The method can further include preparing the biomass feedstock by reducing one or more dimensions of individual pieces of the biomass feedstock.

In some cases, the biomass feedstock has internal fibers, and the biomass feedstock has been sheared to an extent that its internal fibers are substantially exposed. The biomass feedstock can in some cases include or be made up of discrete fibers and/or particles having a maximum dimension of not more than about 0.5 mm.

The biomass feedstock can be prepared and then pretreated, or pretreated and then prepared. The pretreatment method can be selected from, e.g., radiation, such as radiation from a beam of electrons or ions, sonication, pyrolysis, and oxidation. In some embodiments, at least one of the pretreatment methods, e.g., radiation, is performed on the biomass feedstock while the biomass feedstock is exposed to air, nitrogen, oxygen, helium, or argon. In some embodiments, pretreatment can include pretreating the biomass feedstock with steam explosion.

In some embodiments, reducing one or more dimensions of individual pieces of biomass includes shearing, wet or dry grinding, cutting, squeezing, compressing or mixtures of any of these processes. For example, shearing can be performed with a rotary knife cutter. The shearing can produce fibers having an average length-to-diameter ratio of greater than 5/1. In some embodiments, the prepared biomass can have a BET surface area of greater than 0.25 m$^2$/g. The biomass can be sheared to an extent that internal fibers of the biomass are substantially exposed. The biomass can be sheared to an extent that it has a bulk density of less than about 0.35 g/cm$^3$.

In some embodiments, two or more pretreatment methods can be applied to the biomass feedstock, for example radiation and sonication, radiation and oxidation, radiation and pyrolization, sonication and oxidation, sonication and pyrolization, or oxidation and pyrolization. The two or more processes can be performed in any order or at or about the same time.

In some embodiments, the change in molecular structure and/or change in supramolecular structure of the biomass, e.g., the cellulosic or lignocellulosic material or low molecular weight sugar or starchy material, can include a change in any one or more of an average molecular weight, average crystallinity, surface area, degree of polymerization, porosity, branching, grafting, domain size or number, a change in kind or number of chemical functional groups, and a change in formula weight. For example, the change in molecular structure and/or supramolecular structure can include a decrease in either one or both of an average molecular weight and average crystallinity or an increase in either one or both of surface area and porosity.

In some instances, functionalized biomass (biomass in which the number and/or kind of functional groups has been changed) is more soluble and more readily utilized by microorganisms in comparison to un-functionalized biomass. In addition, many of the functionalized materials described herein are less prone to oxidation and can have enhanced long-term stability under ambient conditions.

In some embodiments, at least one pretreatment method can be performed on biomass in which less than about 25 percent by weight of the biomass is in a swollen state, the swollen state being characterized as having a volume of more than about 2.5 percent higher than an unswollen state. In other embodiments, the biomass is mixed with or includes a swelling agent. For example, in any method described herein, the biomass can be mixed with or and include a swelling agent, and the biomass can receive a dose of less than about 10 Mrad of radiation.

The pretreated biomass material can further include, optionally, a buffer, such as sodium bicarbonate or ammonium chloride, an electrolyte, such as potassium chloride or sodium chloride, a growth factor, such as biotin, and/or a base pair such as uracil, a surfactant, a mineral, or a chelating agent.

In some cases, pretreatment is performed while the biomass feedstock is exposed to air, nitrogen, oxygen, helium or argon. Pretreatment may be performed under pressure, e.g., under a pressure of greater than about 2.5 atmospheres. The methods described herein may further include oxidizing the biomass prior to pretreatment.

The biomass feedstock may include, for example, paper, paper products, paper waste, wood, particle board, sawdust, agricultural waste, sewage, silage, grasses, rice hulls, bagasse, cotton, jute, hemp, flax, bamboo, sisal, abaca, straw, corn cobs, corn stover, switchgrass, alfalfa, hay, rice hulls, coconut hair, cotton, synthetic celluloses, seaweed, algae, and mixtures thereof. The biomass may in some cases include a synthetic material.

The biomass can in some cases include a carbohydrate that includes one or more β-1,4-linkages and has a number average molecular weight between about 3,000 and 50,000.

In some implementations, the biomass material includes a starch, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, ocra, sago, sorghum, regular household potatoes, sweet potato, taro, yams, or one or more beans, such as fava beans, lentils, or peas.

In other implementations, the biomass material is or includes a low molecular weight sugar. For example, the biomass materials can include at least about 0.5 percent by weight of a low molecular weight sugar, e.g., at least about 2, 3, 4, 5, 6, 7, 8, 9, 10, 12.5, 25, 35, 50, 60, 70, 80, 90 or even at least about 95 percent by weight of the low molecular weight sugar. In some instances, the biomass is composed substantially of the low molecular weight sugar, e.g., greater than 95 percent by weight, such as 96, 97, 98, 99 or substantially 100 percent by weight of the low molecular weight sugar. Biomass materials that include low molecular weight sugars can be agricultural products or food products, such as sugarcane and sugar beets, or an extract therefrom, e.g., juice from sugarcane or sugar beets. Specific examples of low molecular weight sugars include cellobiose, lactose, sucrose, glucose and xylose, along with derivatives thereof. Processing low molecular weight sugars by any of the methods described herein can make the resulting products more soluble and/or easier to utilize by microbes.

In any of the methods disclosed herein, radiation may be applied from a device that is in a vault.

The term "fibrous material," as used herein, is a material that includes numerous loose, discrete and separable fibers. For example, a fibrous material can be prepared from a bleached Kraft paper fiber source by shearing, e.g., with a rotary knife cutter.

The term "screen," as used herein, means a member capable of sieving material according to size. Examples of screens include a perforated plate, cylinder or the like, or a wire mesh or cloth fabric.

The term "pyrolysis," as used herein, means to break bonds in a material by the application of heat energy. Pyrolysis can occur while the subject material is under vacuum, or immersed in a gaseous material, such as an oxidizing gas, e.g., air or oxygen, or a reducing gas, such as hydrogen.

Oxygen content is measured by elemental analysis by pyrolyzing a sample in a furnace operating at 1300° C. or above.

The terms "biomass" refers to any non-fossilized, i.e., renewable, organic matter. The various types of biomass include plant biomass (defined below), microbial biomass, animal biomass (any animal by-product, animal waste, etc.) and municipal waste biomass (residential and light commercial refuse with recyclables such as metal and glass removed).

The term "plant biomass" and "lignocellulosic biomass" refer to virtually any plant-derived organic matter (woody or non-woody). Plant biomass can include, but is not limited to, agricultural or food crops (e.g., sugarcane, sugar beets or corn kernels) or an extract therefrom (e.g., sugar from sugarcane and corn starch from corn), agricultural crop wastes and residues such as corn stover, wheat straw, rice straw, sugar cane bagasse, and the like. Plant biomass further includes, but is not limited to, trees, woody energy crops, wood wastes and residues such as softwood forest thinnings, barky wastes, sawdust, paper and pulp industry waste streams, wood fiber, and the like. Additionally, grass crops, such as switchgrass and the like have potential to be produced on a large-scale as another plant biomass source. For urban areas, the best potential plant biomass feedstock includes yard waste (e.g., grass clippings, leaves, tree clippings, and brush) and vegetable processing waste.

"Lignocellulosic feedstock," is any type of plant biomass such as, but not limited to, non-woody plant biomass, cultivated crops, such as, but not limited to, grasses, for example, but not limited to, C4 grasses, such as switchgrass, cord grass, rye grass, miscanthus, reed canary grass, or a combination thereof, or sugar processing residues such as bagasse, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the lignocellulosic feedstock may include cellulosic waste material such as, but not limited to, newsprint, cardboard, sawdust, and the like.

Lignocellulosic feedstock may include one species of fiber or alternatively, lignocellulosic feedstock may include a mixture of fibers that originate from different lignocellulosic feedstocks. Furthermore, the lignocellulosic feedstock may comprise fresh lignocellulosic feedstock, partially dried lignocellulosic feedstock, fully dried lignocellulosic feedstock or a combination thereof.

For the purposes of this disclosure, carbohydrates are materials that are composed entirely of one or more saccharide units or that include one or more saccharide units. The saccharide units can be functionalized about the ring with one or more functional groups, such as carboxylic acid groups, amino groups, nitro groups, nitroso groups or nitrile groups and still be considered carbohydrates. Carbohydrates can be polymeric (e.g., equal to or greater than 10-mer, 100-mer, 1,000-mer, 10,000-mer, or 100,000-mer), oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different.

Examples of polymeric carbohydrates include cellulose, xylan, pectin, and starch, while cellobiose and lactose are examples of dimeric carbohydrates. Examples of monomeric carbohydrates include glucose and xylose.

Carbohydrates can be part of a supramolecular structure, e.g., covalently bonded into the structure. Examples of such materials include lignocellulosic materials, such as those found in wood.

A starchy material is one that is or includes significant amounts of starch or a starch derivative, such as greater than about 5 percent by weight starch or starch derivative. For purposes of this disclosure, a starch is a material that is or includes an amylose, an amylopectin, or a physical and/or chemical mixture thereof, e.g., a 20:80 or 30:70 percent by weight mixture of amylose to amylopectin. For example, rice, corn, and mixtures thereof are starchy materials. Starch derivatives include, e.g., maltodextrin, acid-modified starch, base-modified starch, bleached starch, oxidized starch, acetylated starch, acetylated and oxidized starch, phosphate-modified starch, genetically-modified starch and starch that is resistant to digestion.

For purposes of this disclosure, a low molecular weight sugar is a carbohydrate or a derivative thereof that has a formula weight (excluding moisture) that is less than about 2,000, e.g., less than about 1,800, 1,600, less than about 1,000, less than about 500, less than about 350 or less than about 250. For example, the low molecular weight sugar can be a monosaccharide, e.g., glucose or xylose, a disaccharide, e.g., cellobiose or sucrose, or a trisaccharide.

A combustible fuel is a material capable of burning in the presence of oxygen. Examples of combustible fuels include ethanol, n-propanol, n-butanol, hydrogen and mixtures of any two or more of these.

Swelling agents as used herein are materials that cause a discernable swelling, e.g., a 2.5 percent increase in volume over an unswollen state of cellulosic and/or lignocellulosic materials, when applied to such materials as a solution, e.g., a water solution. Examples include alkaline substances, such as sodium hydroxide, potassium hydroxide, lithium hydroxide and ammonium hydroxides, acidifying agents, such as mineral acids (e.g., sulfuric acid, hydrochloric acid and phosphoric acid), salts, such as zinc chloride, calcium carbonate, sodium carbonate, benzyltrimethylammonium sulfate, and basic organic amines, such as ethylene diamine.

A "sheared material," as used herein, is a material that includes discrete fibers in which at least about 50% of the discrete fibers have a length/diameter (L/D) ratio of at least about 5, and that has an uncompressed bulk density of less than about 0.6 g/cm$^3$. A sheared material is thus different from a material that has been cut, chopped or ground.

Changing a molecular structure of a biomass feedstock, as used herein, means to change the chemical bonding arrangement, such as the type and quantity of functional groups, or conformation of the structure. For example, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or an changing an overall domain size.

This application incorporates by reference herein the entire contents of International Application No. PCT/US2007/022719, filed on Oct. 26, 2007. The full disclosures of each of the following U.S. patent applications, which are being filed concurrently herewith, are hereby incorporated by reference herein: U.S. application Ser. No. 12/417,707, now U.S. Pat. No. 7,867,358, issued on Jan. 11, 2011, U.S. application Ser. No. 12/417,720, now U.S. Pat. No. 7,846,295, issued on Dec. 7, 2010, U.S. patent application Ser. No. 12/417,699, now U.S. Pat. No. 7,931,784, issued on Apr. 26, 2011, U.S. application Ser. No. 12/417,840, now U.S. Pat. No. 8,236,535, issued on Aug. 7, 2012, U.S. application Ser. No. 12/417,900, U.S. application Ser. No. 12/417,880, now U.S. Pat. No. 8,212,087, issued on Jul. 3, 2012, U.S. application Ser. No. 12/417,723, U.S. application Ser. No. 12/417,786, now U.S. Pat. No. 8,025,098, issued on Sep. 27, 2011, U.S. application Ser. No. 12/417,904, now U.S. Pat. No. 7,867,359, issued on Jan. 11, 2011.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, Appendices, patent applications, patents, and other references mentioned herein or attached hereto are incorporated by reference in their entirety for all that they contain. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 11B is a schematic side view of a system for irradiating a low bulk density material, while FIG. 11C is cross-sectional of the system taken along 11C-11C.

FIG. 26 is a block diagram illustrating a dry milling process for corn kernels.

FIG. 27 is a block diagram illustrating a wet milling process for corn kernels.

FIG. 32 is a schematic side view of a sonication apparatus, while

DETAILED DESCRIPTION

Figure 1:
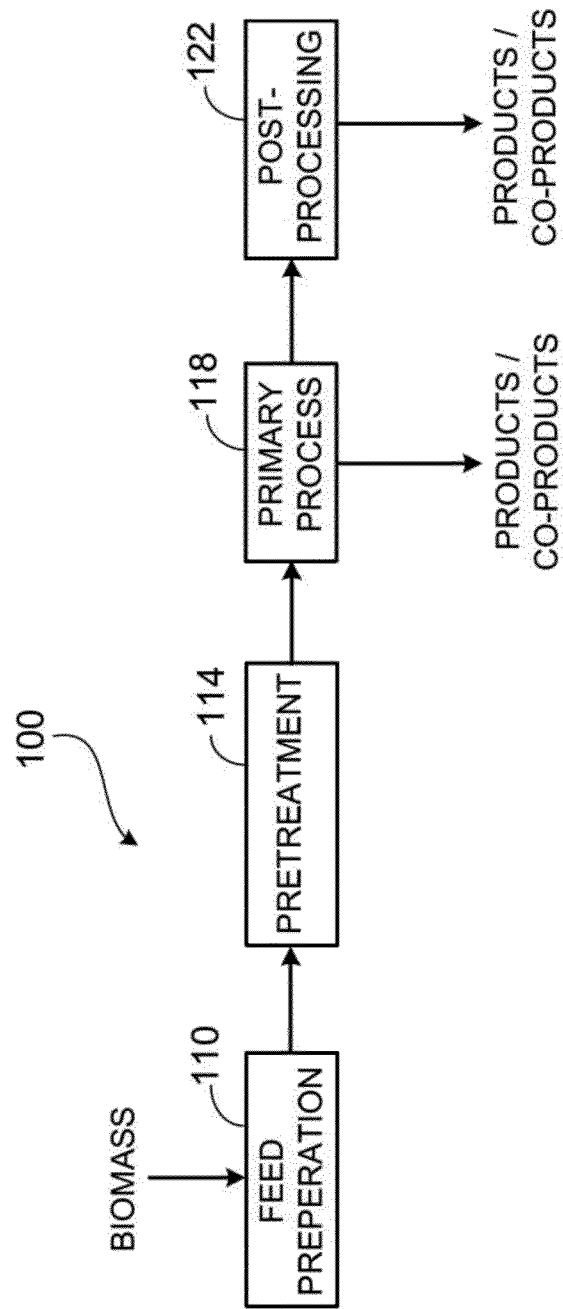
FIG. 1 is a block diagram illustrating conversion of biomass into products and co-products.

Systems and processes are described herein that can use various biomass materials, such as cellulosic materials, lignocellulosic materials, starchy materials or materials that are or that include low molecular weight sugars, as feedstock materials. Such materials are often readily available, but can be difficult to process, e.g., by fermentation, or can gives suboptimal yields at a slow rate. In some cases, the difficulty in processing stems at least in part from the recalcitrance of the feedstock. Processing steps are described herein that can reduce this recalcitrance and thereby facilitate conversion of the biomass feedstock to a desired product.

In the processes described herein, feedstock materials are first physically prepared for processing, often by size reduction of raw feedstock materials. Physically prepared feedstock can then be pretreated or processed using one or more of radiation (which may in some cases be under controlled thermal conditions), sonication, oxidation, pyrolysis, and steam explosion. The various pretreatment systems and methods can be used in combinations of two, three, or even four of these technologies. Other techniques which may be used to enhance the processing of the feedstock are described herein, for example cooling the feedstock between irradiating steps and quenching the biomass feedstock after irradiation.

Functionalized materials are also disclosed herein, having desired types and amounts of functionality, such as carboxylic acid groups, enol groups, aldehyde groups, ketone groups, nitrile groups, nitro groups, or nitroso groups, which can be prepared using the methods described herein. Such functionalized materials can be, e.g., more soluble, easier to utilize by various microorganisms or can be more stable over the long term, e.g., less prone to oxidation.

In some cases, the feedstock can include low molecular weight sugars or starchy materials, as will be discussed in detail herein.

Types of Biomass

Generally, any biomass material that is or includes carbohydrates composed entirely of one or more saccharide units or that include one or more saccharide units can be processed by any of the methods described herein. For example, the biomass material can be cellulosic or lignocellulosic materials, starchy materials, such as kernels of corn, grains of rice or other foods, or materials that are or that include one or more low molecular weight sugars, such as sucrose or cellobiose.

For example, such materials can include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these. Suitable materials include those listed in the Summary section, above.

Fiber sources include cellulosic fiber sources, including paper and paper products (e.g., polycoated paper and Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Natural or synthetic fiber sources can be obtained from virgin scrap textile materials, e.g., remnants or they can be post consumer waste, e.g., rags. When paper products are used as fiber sources, they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Also, the fiber source can be obtained or derived from human (e.g., sewage), animal or plant wastes. Additional fiber sources have been described in U.S. Pat. Nos. 6,448,307, 6,258,876, 6,207,729, 5,973,035 and 5,952,105.

Microbial biomass includes biomass derived from naturally occurring or genetically modified unicellular organisms and/or multicellular organisms, e.g., organisms from the ocean, lakes, bodies of water, e.g., salt water or fresh water, or on land, and that contains a source of carbohydrate (e.g., cellulose). Microbial biomass can include, but is not limited to, for example protists (e.g., animal (e.g., protozoa such as flagellates, amoeboids, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Animal biomass includes any organic waste material such as animal-derived waste material or excrement or human waste material or excrement (e.g., manure and sewage).

In some embodiments, the carbohydrate is or includes a material having one or more β-1,4-linkages and having a number average molecular weight between about 3,000 and 50,000. Such a carbohydrate is or includes cellulose (I), which is derived from (β-glucose 1) through condensation of β(1→4)-glycosidic bonds. This linkage contrasts itself with that for α(1→4)-glycosidic bonds present in starch and other carbohydrates.

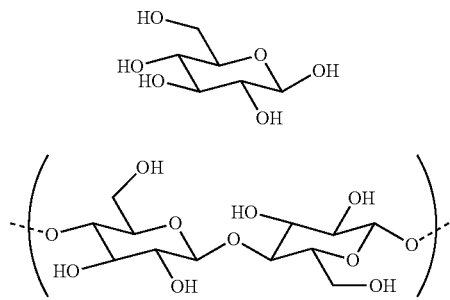

Starchy Materials

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, ocra, sago, sorghum, regular household potatoes, sweet potato, taro, yams, or one or more beans, such as favas, lentils or peas. A blend of any two or more starchy materials is also a starchy material. Starch sources include, e.g., wheat, barley, corn and potatoes. In particular embodiments, the starchy material is derived from corn. Various corn starches and derivatives are described in "Corn Starch," Corn Refiners Association (11$^{th}$ Edition, 2006), which is included as Appendix A in U.S. Pat. No. 8,212,087.

A starch (e.g., CAS#9005-25-8 and chemical formula $(C_6H_{10}O_5)_n$) generally comprises a mixture of amylose and amylopectin (usually in 20:80 or 30:70 ratios) and generally exists as a homopolymer of repeating anhydroglucose units joined by an α-glucosidic on the next starch unit through hemiacetal linkages. Starch molecules typically are made up of 1,4-linkages are referred to as amylose while 1,6-linkages serve as the branching point in branched starch molecules called amylopectin.

Granular Structure

TABLE 1

Granule Size of Various Starches

| Starch Species | Granule Size Range (μm) (Coulter Counter) | Average size (μm) |
|---|---|---|
| Waxy Rice | 2-13 | 5.5 |
| High Amylose Corn | 4-22 | 9.8 |
| Corn | 5-25 | 14.3 |
| Cassava | 3-28 | 14 |
| Sorghum | 3-27 | 16 |
| Wheat | 3-34 | 6.5, 19.5 |
| Sweet Potato | 4-40 | 18.5 |
| Arrowroot | 9-40 | 23 |
| Sago | 15-50 | 33 |
| Potato | 10-70 | 36 |
| Canna (Aust. Arrowroot) | 22-85 | 53 |

Plants store starch within specialized organelles called amyloplasts where they are deposited to form granules. These granules are comprised of newly-synthesized starch layered around a hilum nucleus, and vary in diameter from 2 to 130 microns. The size and shape of the granule is characteristic of the plant's origin and serves as a way of identifying the source of a particular starch (Table 1). The structure of the granule of grain is crystalline with the starch molecules orienting in such a way as to form radially oriented crystals giving rise to the phenomenon of birefringence. When a beam of polarized light is directed through a starch granule, the granule is divided by dark lines into four wedge-shaped sections. This cross-hatching or cross is characteristic of spherocrystalline structures.

Amylose

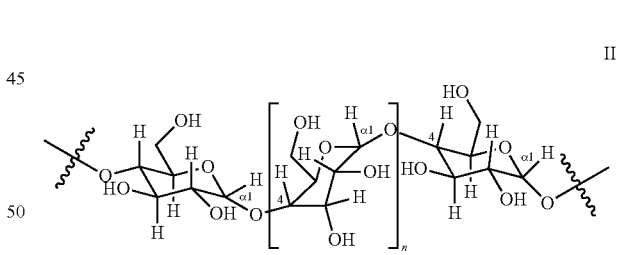

Amylose molecules consist of single mostly-unbranched chains with 500-20,000 α-(1,4)-D-glucose units depending on the source. The α(1,4) bonds promote the formation of a helix structure. The structural formula of amylose is pictured in II where the number of repeated glucose subunits (n) can be many thousands (usually in the range of 300 to 3000). Amylose starch is less readily digested than amylopectin; however, it takes up less space so is preferred for storage in plants. Amylose makes up about 30% of the stored starch in plants. The digestive enzyme amylase works on the ends of the starch molecule, breaking it down into sugars.

Amylose molecules contribute to gel formation because the linear chains can orient parallel to each other, moving close enough together to bond. Probably due to the ease with which amylose molecules slip past each other in the cooked paste, they do not contribute significantly to viscosity.
Amylopectin Genetically Modified Starch Genetically modified starch, which refers to starch from genetically engineered plants, has been modified to reduce

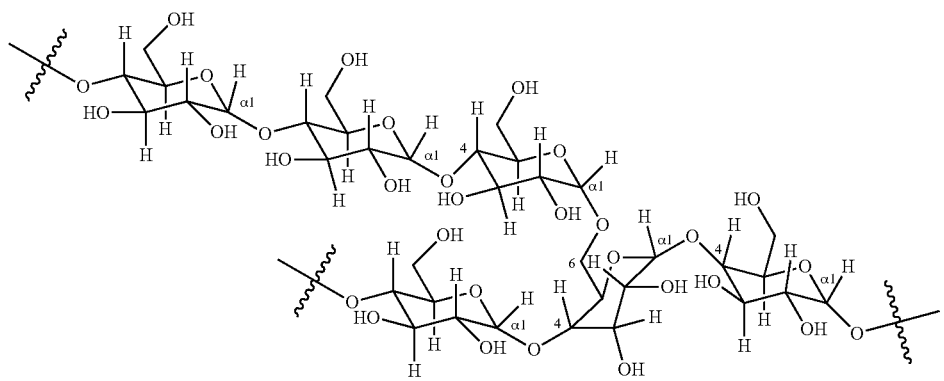

III

Amylopectin is formed by non-random α-(1,6)-branching of the amylose-type α-(1,4)-D-glucose structure. As can be seen in III, glucose units are linked in a linear way with α (1,4) bonds. Branching takes place with α (1,6) bonds occurring every 24 to 30 glucose units and is determined by br\anching enzymes. Each amylopectin molecule contains a million or so residues, about 5% of which form the branch points.

The branched amylopectin molecules give viscosity to the cooked paste due to the role it serves in maintaining the swollen granule. Their side chains and bulky shape keep amylopectin molecules from orienting closely enough to hydrogen bond together, so they do not usually contribute to gel formation.
Source Plants hydrolyze starch releasing the glucose subunits when energy is required. By far the largest source of starch is corn (maize) with other commonly used sources being wheat, potato, tapioca and rice. The relative proportions of amylose to amylopectin and 1,6-linkage branch-points are established genetically and are relatively constant for each species of starch. For example, amylomaizes contain over 50% amylase, whereas "waxy" maize has almost none (~3%).
Unprocessed Starch Starch that is produced by the corn wet milling process and then dried is referred to as common, regular, or unmodified corn starch. Various forms of corn starch exist including, fine or coarse powders, flakes, pearls or even larger particles. Unmodified starch can be minimally processed by adjusting the pH, by mild heat treatment, or by adding small quantities of chemicals or adjuvants before or after drying in order to optimize performance. As an example, enzyme conversion of starch to sugars can be accelerated by adjusting the pH of the starch.

By far the most consumed polysaccharide in the human diet is starch. Starch (in particular cornstarch) is used in cooking for thickening foods such as sauces. In industry, it is used in the manufacturing of adhesives, paper, textiles, and as a mold in the manufacture of sweets such as wine gums and jelly beans. Papermaking is the largest non-food application for starches globally, consuming millions of metric tons annually. In a typical sheet of copy paper for example, the starch content may be as high as 8%. Both chemically modified and unmodified starches are used in papermaking.

The chemical composition of starch, highly oxygenated carbon molecules, makes starch an excellent product for use as a chemical feedstock.

the need for chemical processing (reducing cost, toxicity, or environmentally hazardous processes), or in order to produce novel carbohydrates which might not naturally occur in the plant species being harvested. The modification in this sense refers to the genetic engineering of the plant DNA, and not the later processing or treatment of the starch or starch granules.

Genetically modified starch is of particular interest in the manufacture of biodegradable polymers and non-cellulose feedstock in the paper industry, as well as the creation of new food additives. For example, waxy maize was studied extensively in the 1950's for its desirable properties. Waxy maize starch, which is essentially 100% amylopectin, yields pastes that are almost clear when cool, non-congealing, and when dried in thin films, yields a translucent, water-soluble coating often used for thickening a wide variety of prepared foods. Genetic modification of this starch to try and increase the amylose content could potentially result in an excellent film former and might be spun into a fiber. Research in this area resulted in the commercial development of two corn hybrids, one containing about 55%, the other about 70% amylose, and recently research has resulted in developing a starch with 80% amylose.
Modified Starch Modified starch is a food additive which is prepared by treating starch or starch granules, causing the starch to be partially degraded. Modified starch is used as a thickening agent, stabilizer, or an emulsifier. Apart from food products, modified starch is also found in pharmaceuticals. Starches are modified for a number of reasons including, to increase their stability to excessive heat, acid, and freezing; to change their texture; or to lengthen or shorten gelatinization time.
Acid-Modified Starch Acid-treated starch, usually simply referred to as "modified starch", is prepared by treating starch or starch granules with inorganic acids. The primary reaction taking place during acid treatment is hydrolysis of glucosidic bonds in starch molecules. Acid modification reduces the chain length of the starch, but does not substantially change the molecular configuration. In this method, a starch-water suspension is agitated while being subjected to mild treatment with dilute mineral acid at temperatures elevated but below the starch gelatinization temperature. Upon achieving the desired viscosity, the acid is neutralized with sodium carbonate and the starch is filtered, washed, and dried.

Oxidized Corn Starch

Another method for reducing viscosity is oxidation. Although oxidizing agents such as chlorine, hydrogen peroxide and potassium permanganate can be used, oxidized starches produced by the wet milling process are almost always made using sodium hypochlorite as the oxidizing agent. Aqueous starch suspensions under agitation are treated with dilute sodium hypochlorite containing a small excess of sodium hydroxide (NaOH) and heated to 120° F. When the desired viscosity is achieved, the oxidized starch slurry is treated with a reducing agent such as sodium bisulfite to remove excess hypochlorite, the pH is adjusted, and the starch is filtered, washed and finally dried. Treatment of starch with an oxidizing agent randomly converts hydroxyl groups to carboxyl or carbonyl groups, which results in the cleavage of the adjacent glucosidic bond. Oxidized starches are used in batters and breading as they adhere quite well to meats.

Dextrins

Dextrins are a group of low molecular weight carbohydrates produced by the dry heating or roasting of unmodified starch, with or without an acid or alkaline catalyst. Other dextrinization methods utilize a fluid bed, in which unmodified starch is placed in a reactor and suspended or "fluidized" in a stream of heated air. The starch is then acidified and heated until the desired end product is obtained. During dextrinization, the granule is not destroyed but granule integrity is disrupted. When dextrins are suspended in water and heated, the granules swell and separate into layers that eventually break free and disperse. Dextrins are mixtures of linear $\alpha$-(1,4)-linked D-glucose polymers starting with an $\alpha$-(1,6) bond. Industrial production is, in general, performed by acidic hydrolysis of potato starch. Dextrins are water-soluble, white to slightly yellow solids that are optically active. Under analysis, dextrins can be detected with iodine solution, giving a red coloration.

There are three major types of dextrins: white, yellow, and British gums. White dextrins have a white color and have reduced viscosities, and cold water solubilities ranging from 5 to over 90%. White dextrins are used to make very soft gels. Yellow dextrins (produced with less acid, higher temperatures, and more time) are yellow in color and have higher water solubility. Yellow dextrins are used for making high solids pastes that are very tacky and, when applied in thin films, dry rapidly. Finally, British gums are produced by adding little or no acid to very dry starch and then roasting while gradually increasing the temperature. They are tan to light brown in color and are used to prepare nearly solid gels through very soft gels to viscous liquids.

Cyclodextrins

Figure 4:
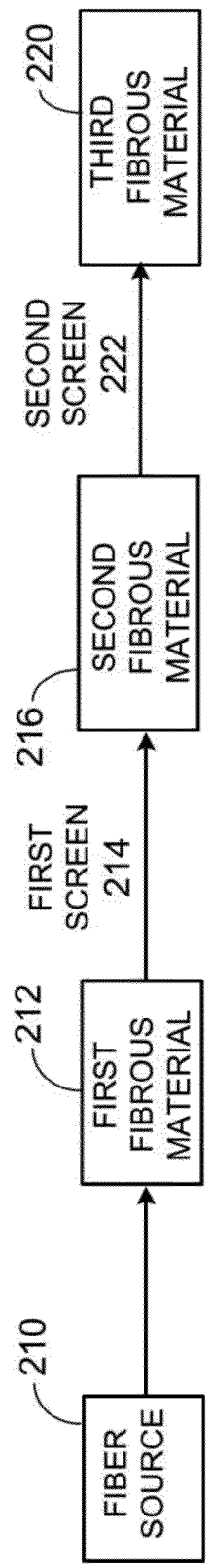
FIG. 4 is block diagram illustrating conversion of a fiber source into a first, second and third fibrous material.

Cyclodextrins are non-reducing cyclic glucose oligosaccharides resulting from the cyclomaltodextrin glucanotransferase catalyzed degradation of starch. There are three common cyclodextrins with 6, 7 or 8 D-glucopyranonsyl residues ($\alpha$-, $\beta$-, and $\gamma$-cyclodextrin, respectively) linked by $\alpha$-1,4 glycosidic bonds (FIG. 4). All three cyclodextrins have similar structures (bond lengths and orientations) apart from the structural necessities of accommodating a different number of glucose residues. They present a bottomless bowl-shaped (truncated cone) molecule stiffened by hydrogen bonding between the 3-OH and 2-OH groups around the outer rim. Cyclodextrins are used for encapsulation for controlled flavor release, masking odors and tastes, stabilizing emulsions, increasing foaming power, and controlling or masking color.

Starch Derivatives (Crosslinked and Stabilization)

Starch can be chemically derivatized at the primary and secondary hydroxyl positions, which imparts different properties than those found in the parent starch. This is presumably due to disruption of hydrogen bonds. Two types of derivatives are prepared commercially, crosslinked/inhibited and stabilization. Crosslinked starches, sometimes referred to as inhibited starches, are made by reacting hydroxyl groups on two different molecules within a granule with a bifunctional agent. Reagents such as phosphorus oxychloride or sodium trimetaphosphate may be used as crosslinking agents. Very small amounts of these agents can exert a marked effect on the behavior of the cooked starch.

Starch can be stabilized against gelling using monofunctional reagents. These reagents react with hydroxyl groups on the starch to introduce substituent groups that interfere with hydrogen bonding effects thereby increasing their water combining capacity or viscosity, or imparting a positive charge to the starch molecule. Reagents used in the stabilization of starch through disruption of hydrogen bonding include, ethylene oxide to produce hydroxyethyl starch, acetic anhydride to produce starch acetates, succinic anhydride to produce starch succinates, monosodium orthophosphate or sodium tripolyphosphate to produce starch phosphates, and propylene oxide to produce hydroxypropyl starches. Reagents that impart a positive charge to the starch molecule include tertiary or quaternary amines to produce cationic starches.

Pregelatinized Starch

Suspensions of many starches and starch derivatives can be gelatinized and dried to yield a broad variety of pregelatinized starches. This is done on a single drum dryer with applicator rolls. The starch slurry is heated to gelatinize it, instantaneously dried and ground to desired granulation requirement. Pregelatinized starch is used to thicken instant desserts such as puddings, allowing the food to thicken with the addition of cold water or milk. Similarly, cheese sauce granules (such as in Macaroni and Cheese or lasagna) or gravy granules may be thickened with boiling water without the product going lumpy. Commercial pizza toppings containing modified starch will thicken when heated in the oven, keeping them on top of the pizza, and then become runny when cooled.

Bleached Starches

Bleaching by very light oxidation is carried out using sodium hypochlorite, sodium chlorite, hydrogen peroxide, potassium permanganate, peracetic acid, or ammonium persulfate with sulfur dioxide. Interaction with the starch molecules must be very small since no change occurs in the physical properties of the starch or its solution except in its color. Theoretically, there will be production of a few aldehyde or carboxyl groups. Only trace amounts of sodium chloride, sodium sulfate or sodium acetate remain in the final product. The bleached starch is recovered on continuous filters or centrifuges using copious amounts of water to remove trace amounts of inorganic salts formed from the bleaching agent, dried and packaged.

Low Molecular Weight Sugars

Biomass materials that include low molecular weight sugars can, e.g., include at least about 0.5 percent by weight of the low molecular sugar, e.g., at least about 2, 3, 4, 5, 6, 7, 8, 9, 10, 12.5, 25, 35, 50, 60, 70, 80, 90 or even at least about 95 percent by weight of the low molecular weight sugar. In some instances, the biomass is composed substantially of the low molecular weight sugar, e.g., greater than 95 percent by weight, such as 96, 97, 98, 99 or substantially 100 percent by weight of the low molecular weight sugar.

Biomass materials that include low molecular weight sugars can be agricultural products or food products, such as sugarcane and sugar beets or an extract therefrom, e.g., juice from sugarcane, or juice from sugar beets. Biomass materials that include low molecular weight sugars can be substantially pure extracts, such as raw or crystallized table sugar (sucrose). Low molecular weight sugars include sugar derivatives. For example, the low molecular weight sugars can be oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different.

Specific examples of low molecular weight sugars include cellobiose, lactose, sucrose, glucose and xylose, along with derivatives thereof. In some instances, sugar derivatives are more rapidly dissolved in solution or utilized by microbes to provide a useful material, such as ethanol or butanol. Several such sugars and sugar derivatives are shown below.

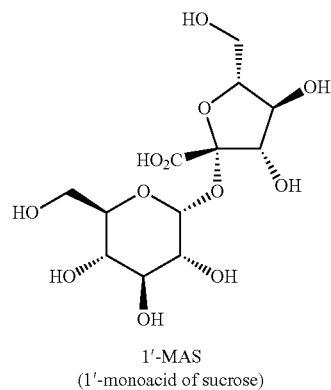

1'-MAS
(1'-monoacid of sucrose)

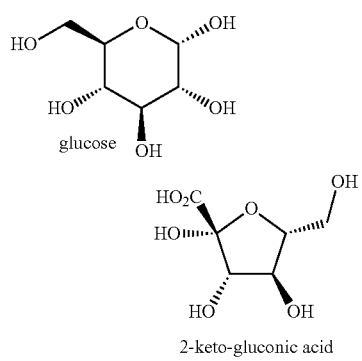

glucose 2-keto-gluconic acid

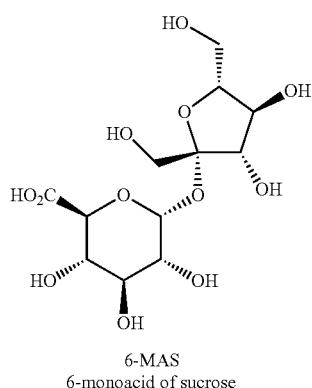

6-MAS
6-monoacid of sucrose

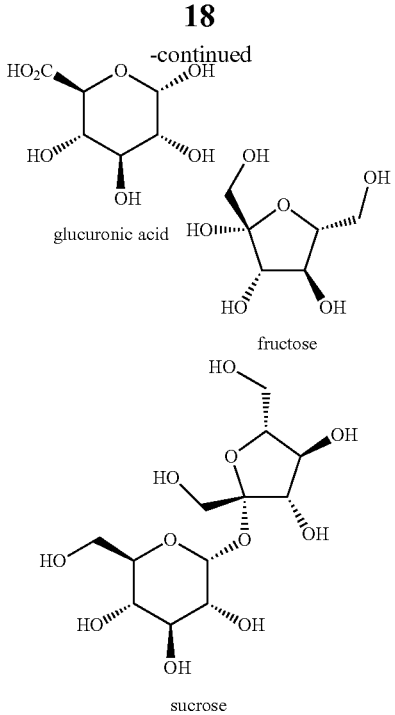

glucuronic acid fructose sucrose

Ethanol from Low Molecular Weight Sugars

More than half of world ethanol production is produced from sugar and sugar byproducts, with Brazil being by far the world leader. Currently, there is no commercial production of ethanol from sugarcane or sugar beets in the United States, where 97 percent of ethanol is produced from corn.

Technologically, the process of producing ethanol from sugar is simpler than converting corn into ethanol. Converting corn into ethanol requires additional cooking (wet milling process) and the application of enzymes, whereas the conversion of sugar requires only a yeast fermentation process. The energy requirement for converting sugar into ethanol is about half that for corn. However, the technology and direct energy costs are but one of several factors that determine the feasibility of ethanol production. Other factors include relative production costs (including feedstocks), conversion rates, proximity to processing facilities, alternative prices and government policies, facility construction and processing costs. As other countries have shown that it can be economically feasible to produce ethanol from sugar and other new feedstocks are researched, interest in the United States in ethanol production from sugar has increased.

In response to the growing interest around sugar and ethanol, USDA released a study in July 2006 titled: "The Economic Feasibility of Ethanol Production from Sugar in the United States" which is incorporated herein by reference in its entirety. The report found that at the current market prices for ethanol, converting sugarcane, sugar beets and molasses to ethanol would be profitable (see Table 1).

TABLE 1

Current Market Prices for Ethanol

| Feedstock | Total Costs* | Processing Costs* |
| --- | --- | --- |
| Corn (wet milling/dry milling): | $1.03/1.05 | $0.63/0.52 |
| Raw Sugarcane | $2.40 | $0.92 |
| Raw Sugar beets | $2.35 | $0.77 |
| Molasses** | $1.27 | $0.36 |

TABLE 1-continued

Current Market Prices for Ethanol

| Feedstock | Total Costs* | Processing Costs* |
|---|---|---|
| Raw Sugar** | $3.48 | $0.36 |
| Refined sugar** | $3.97 | $0.36 |

*Per gallon
**Excludes transportation costs

Sugar Beets

Sugar beets are an annual crop grown in 11 states across a variety of climatic conditions, from the hot climate of the Imperial Valley of California to the colder climates of Montana and North Dakota. Sugar beet byproducts include beet pulp, which can be sold for animal feed, and molasses, which is also sold for animal feed or further processed to extract more sugar.

Sugar beet processing facilities convert raw sugar beets directly into refined sugar in a 1-step process. While planted sugar beet acreage has fallen slightly since the 1990s, sugar production actually increased due to investments in new processing equipment, the adoption of new technologies, improved crop varieties and enhanced technologies for the de-sugaring of molasses. Sugar beets are very bulky and relatively expensive to transport and must be processed fairly quickly before the sucrose deteriorates. Therefore, all sugar beet processing plants are located in the production areas.

Sugarcane

Sugarcane is a perennial tropical crop produced in four states: Florida, Hawaii, Louisiana and Texas. Byproducts of sugarcane processing include molasses and bagasse, the fibrous material that remains after sugar is pressed from the sugarcane. Bagasse is often burned as fuel to help power the sugarcane mills. Sugarcane is initially processed into raw sugar at mills near the cane fields. Like beets, cane is bulky and relatively expensive to transport and must be processed as soon as possible to minimize sucrose deterioration. The raw sugar is then shipped to refineries to produce refined sugar.

Sugar beets have gained a greater share of U.S. sugar production over the past decade, now accounting for 58.8 percent of the nation's sugar output while sugarcane fell to 41.2 percent.

Molasses

The most widely used sugar for ethanol fermentation is blackstrap molasses which contains about 35-40 wt. % sucrose, 15-20 wt. % invert sugars such as glucose and fructose, and 28-35 wt. % of non-sugar solids. Blackstrap (syrup) is collected as a by-product of cane sugar manufacture. The molasses is diluted to a mash containing ca 10-20 wt. % sugar. After the pH of the mash is adjusted to about 4-5 with mineral acid, it is inoculated with the yeast, and the fermentation is carried out non-aseptically at 20-32° C. for about 1-3 days. The fermented beer, which typically contains approximately 6-10 wt. % ethanol, is then set to the product recovery in purification section of the plant.

Ethanol production (using 141 gallons per ton of sucrose conversion factor) was calculated for sugarcane, sugar beets and molasses below.

Sugarcane:
   12.24% raw sugar recovery rate, plus 41.6 pounds of sucrose from cane molasses
      1 ton of sugarcane=235.0 pounds of sucrose from raw sugar
      and 41.6 lbs of sucrose from molasses
      =276.6 pounds (0.1383 tons) sucrose
      =19.5 gallons of ethanol
   or 0.051 tons of sugarcane per gallon of ethanol produced Sugar beets:
   15.58% refined sugar recovery rate, plus 40.0 pounds of sucrose from beet molasses
      1 ton of sugar beets=311.6 pounds of sucrose from refined sugar
      and 40.0 pounds of sucrose from beet molasses
      =351.6 pounds (0.1758 tons) of sucrose
      =24.8 gallons of ethanol
   or 0.040 tons of sugar beets per gallon of ethanol produced Molasses:
   49.2% total sugars as sucrose
   1 ton of molasses=984 pounds (0.492 tons) of sucrose
   =69.4 gallons of ethanol
   or 28.8 pounds of molasses per gallon of ethanol produced
   or 2.45 gallons of molasses per gallon of ethanol produced
      (using a conversion of 1.0 gallon of molasses=11.74 pounds of weight)

Raw Sugar:
   96.0% totals sugars as sucrose
   1 ton of raw sugar=1920 pounds (0.96 tons) of sucrose
   =135.4 gallons of ethanol
   or 14.77 pounds of raw sugar per gallon of ethanol produced Refined Beet Sugar:
   100.0% total sugars as sucrose
   1 ton of refined sugar=2000 pounds (1.0 ton) of sucrose
   =141.0 gallons of ethanol
   or 14.18 pounds of refined sugar per gallon of ethanol produced Results from this study have several important implications concerning the production of ethanol from sugar crops in the United States. First, under existing fermentation technology, corn is currently the cheapest feedstock available for use in the production of ethanol in the United States. Second, given current and future projected sugar and ethanol market prices, it appears that the production of sugar is the most profitable use of sugarcane or sugar beets. Third, cellulosic conversion of biomass into ethanol offers the potential for a wide variety of feedstocks to be used in ethanol production. Systems and processes are described herein that can utilize these low molecular weight to produce ethanol more rapidly and more cost effectively.

Blends of any biomass materials described herein can be utilized for making any of the products described herein, such as ethanol. For example, blends of cellulosic materials and starchy materials can be utilized for making any product described herein.

Systems for Treating Biomass

FIG. 1 shows a system 100 for converting biomass, particularly biomass with significant cellulosic and lignocellulosic components and/or starchy components, into useful products and co-products. System 100 includes a feed preparation subsystem 110, a pretreatment subsystem 114, a primary process subsystem 118, and a post-processing subsystem 122. Feed preparation subsystem 110 receives biomass in its raw form, physically prepares the biomass for use as feedstock by downstream processes (e.g., reduces the size of and homogenizes the biomass), and stores the biomass both in its raw and feedstock forms. Biomass feedstock with significant cellulosic and/or lignocellulosic components, or starchy components can have a high average molecular weight and crystallinity that can make processing the feedstock into useful products (e.g., fermenting the feedstock to produce ethanol) difficult. For example, others have used acids, bases and enzymes to process cellulosic, lignocellulosic or starchy feedstocks. As described herein, in some embodiments, such treatments are unnecessary, or are necessary only in small or catalytic amounts.

Pretreatment subsystem 114 receives feedstock from the feed preparation subsystem 110 and prepares the feedstock for use in primary production processes by, for example, reducing the average molecular weight and crystallinity of the feedstock. Primary process subsystem 118 receives pretreated feedstock from pretreatment subsystem 114 and produces useful products (e.g., ethanol, other alcohols, pharmaceuticals, and/or food products). In some cases, the output of primary process subsystem 118 is directly useful but, in other cases, requires further processing provided by post-processing subsystem 122. Post-processing subsystem 122 provides further processing to product streams from primary process system 118 which require it (e.g., distillation and denaturation of ethanol) as well as treatment for waste streams from the other subsystems. In some cases, the co-products of subsystems 114, 118, 122 can also be directly or indirectly useful as secondary products and/or in increasing the overall efficiency of system 100. For example, post-processing subsystem 122 can produce treated water to be recycled for use as process water in other subsystems and/or can produce burnable waste which can be used as fuel for boilers producing steam and/or electricity.

The optimum size for biomass conversion plants is affected by factors including economies of scale and the type and availability of biomass used as feedstock. Increasing plant size tends to increase economies of scale associated with plant processes. However, increasing plant size also tends to increase the costs (e.g., transportation costs) per unit of feedstock. Studies analyzing these factors suggest that the appropriate size for biomass conversion plants can range from 1000 to 10,000 or more dried tons of feedstock per day depending at least in part on the type of feedstock used. The type of feedstock can also impact plant storage requirements with plants designed primarily for processing feedstock whose availability varies seasonally (e.g., corn stover) requiring more on- or of-site feedstock storage than plants designed to process feedstock whose availability is relatively steady (e.g., waste paper).

Physical Preparation

In some cases, methods of processing begin with a physical preparation of the feedstock, e.g., size reduction of raw feedstock materials, such as by cutting, grinding, shearing, ball milling, nip-roll processing, or chopping. In some cases, the material can be reduced into particles using a hammermill, disk-refiner, or flaker. In some cases, loose feedstock (e.g., recycled paper, starchy materials, or switchgrass) is prepared by shearing or shredding. Screens and/or magnets can be used to remove oversized or undesirable objects such as, for example, rocks or nails from the feed stream.

Feed preparation systems can be configured to produce feed streams with specific characteristics such as, for example, specific maximum sizes, specific length-to-width, or specific surface areas ratios. As a part of feed preparation, the bulk density of feedstocks can be controlled (e.g., increased or decreased).

Size Reduction

In some embodiments, the material to be processed is in the form of a fibrous material that includes fibers provided by shearing a fiber source. For example, the shearing can be performed with a rotary knife cutter.

Figure 2:
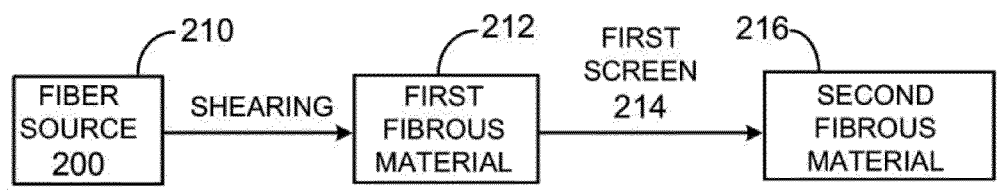
FIG. 2 is block diagram illustrating conversion of a fiber source into a first and second fibrous material.

For example, and by reference to FIG. 2, a fiber source 210 is sheared, e.g., in a rotary knife cutter, to provide a first fibrous material 212. The first fibrous material 212 is passed through a first screen 214 having an average opening size of 1.59 mm or less (¹⁄₁₆ inch, 0.0625 inch) to provide a second fibrous material 216. If desired, fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through the first screen are performed concurrently. The shearing and the passing can also be performed sequentially, e.g., in a batch-type process.

Figure 3:
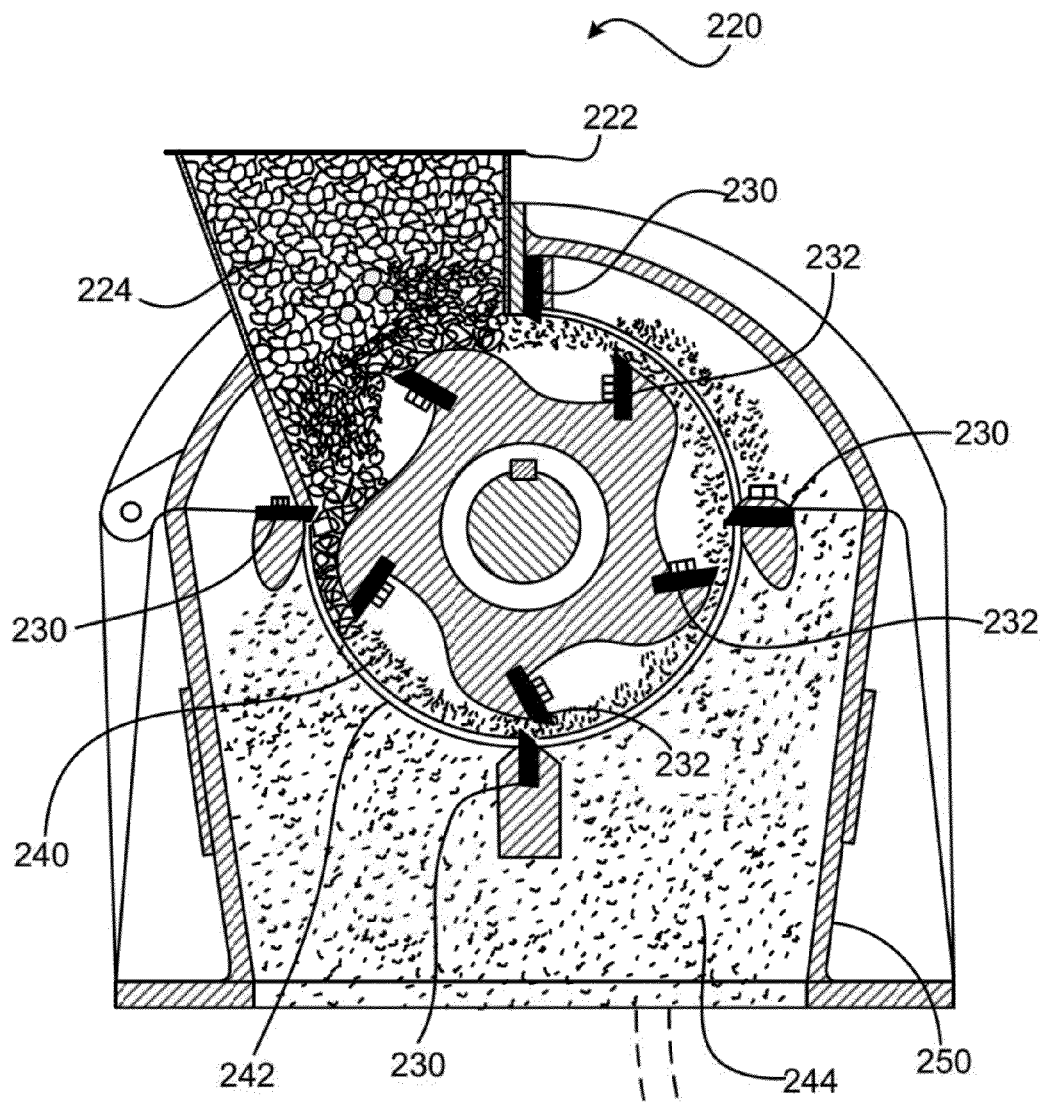
FIG. 3 is a cross-sectional view of a rotary knife cutter.

For example, a rotary knife cutter can be used to concurrently shear the fiber source and screen the first fibrous material. Referring to FIG. 3, a rotary knife cutter 220 includes a hopper 222 that can be loaded with a shredded fiber source 224 prepared by shredding the fiber source. Shredded fiber source is sheared between stationary blades 230 and rotating blades 232 to provide a first fibrous material 240. First fibrous material 240 passes through screen 242, and the resulting second fibrous material 244 is captured in bin 250. To aid in the collection of the second fibrous material, the bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source 252 is utilized to maintain the bin below nominal atmospheric pressure.

Shearing can be advantageous for "opening up," "stressing," or even reducing the molecular weight of the fibrous materials, making the cellulose of the materials more susceptible to chain scission and/or reduction of crystallinity. The open materials can also be more susceptible to oxidation when irradiated.

The fiber source can be sheared in a dry state, a hydrated state (e.g., having up to ten percent by weight absorbed water), or in a wet state, e.g., having between about 10 percent and about 75 percent by weight water. The fiber source can even be sheared while partially or fully submerged under a liquid, such as water, ethanol, or isopropanol.

The fiber source can also be sheared in a gas (such as a stream or atmosphere of gas other than air), e.g., oxygen or nitrogen, or steam.

Other methods of making the fibrous materials include, e.g., stone grinding, mechanical ripping or tearing, pin grinding, ball milling, nip-roll processing, or air attrition milling.

If desired, the fibrous materials can be separated, e.g., continuously or in batches, into fractions according to their length, width, density, material type, or some combination of these attributes.

For example, ferrous materials can be separated from any of the fibrous materials by passing a fibrous material that includes a ferrous material past a magnet, e.g., an electromagnet, and then passing the resulting fibrous material through a series of screens, each screen having different sized apertures.

The fibrous materials can also be separated, e.g., by using a high velocity gas, e.g., air. In such an approach, the fibrous materials are separated by drawing off different fractions, which can be characterized photonically, if desired. Such a separation apparatus is discussed, e.g., in Lindsey et al, U.S. Pat. No. 6,883,667.

The fibrous materials can have a low moisture content, e.g., less than about 7.5, 5, 3, 2.5, 2, 1.5, 1, or 0.5% by weight before processing. This material can be irradiated with a beam of particles, such as electrons or protons. The irradiation can be immediately following preparation of the material, or after a moisture reduction step, e.g., drying at approximately 105° C. for 4-18 hours, so that the moisture content is, e.g., less than about 0.5% before use.

If desired, lignin can be removed from any of the fibrous materials that include lignin. Also, to aid in the breakdown of the materials that include the cellulose, the material can be treated prior to irradiation with heat, a chemical (e.g., mineral acid, base or a strong oxidizer such as sodium hypochlorite) and/or an enzyme.

In some embodiments, the average opening size of the first screen is less than 0.79 mm (1/32 inch, 0.03125 inch), e.g., less than 0.51 mm (1/50 inch, 0.02000 inch), less than 0.40 mm (1/64 inch, 0.015625 inch), less than 0.23 mm (0.009 inch), less than 0.20 mm (1/128 inch, 0.0078125 inch), less than 0.18 mm (0.007 inch), less than 0.13 mm (0.005 inch), or even less than less than 0.10 mm (1/256 inch, 0.00390625 inch). The screen is prepared by interweaving monofilaments having an appropriate diameter to give the desired opening size. For example, the monofilaments can be made of a metal, e.g., stainless steel. As the opening sizes get smaller, structural demands on the monofilaments may become greater. For example, for opening sizes less than 0.40 mm, it can be advantageous to make the screens from monofilaments made from a material other than stainless steel, e.g., titanium, titanium alloys, amorphous metals, nickel, tungsten, rhodium, rhenium, ceramics, or glass. In some embodiments, the screen is made from a plate, e.g., a metal plate, having apertures, e.g., cut into the plate using a laser. In some embodiments, the open area of the mesh is less than 52%, e.g., less than 41%, less than 36%, less than 31%, less than 30%.

In some embodiments, the second fibrous material is sheared and passed through the first screen, or a different sized screen. In some embodiments, the second fibrous material is passed through a second screen having an average opening size equal to or less than that of first screen.

Referring to FIG. 4, a third fibrous material 220 can be prepared from the second fibrous material 216 by shearing the second fibrous material 216 and passing the resulting material through a second screen 222 having an average opening size less than the first screen 214.

Generally, the fibers of the fibrous materials can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (i.e., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

The average length-to-diameter ratio of the second fibrous material 14 can be, e.g., greater than 8/1, 10/1, 15/1, 20/1, 25/1, or even greater than 50/1. An average length of the second fibrous material 14 can be, e.g., between about 0.5 mm and 2.5 mm, e.g., between about 0.75 mm and 1.0 mm, and an average width (i.e., diameter) of the second fibrous material 14 can be, e.g., between about 5 μm and 50 μm, e.g., between about 10 μm and 30 μm.

In some embodiments, a standard deviation of the length of the second fibrous material 14 is less than 60 percent of an average length of the second fibrous material 14, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the second fibrous material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$. A porosity of the second fibrous material 14 can be, e.g., greater than 20 percent, greater than 25 percent, greater than 35 percent, greater than 50 percent, greater than 60 percent, greater than 70 percent, e.g., greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, a ratio of the average length-to-diameter ratio of the first fibrous material to the average length-to-diameter ratio of the second fibrous material is, e.g., less than 1.5, e.g., less than 1.4, less than 1.25, less than 1.1, less than 1.075, less than 1.05, less than 1.025, or even substantially equal to 1.

In particular embodiments, the second fibrous material is sheared again and the resulting fibrous material passed through a second screen having an average opening size less than the first screen to provide a third fibrous material. In such instances, a ratio of the average length-to-diameter ratio of the second fibrous material to the average length-to-diameter ratio of the third fibrous material can be, e.g., less than 1.5, e.g., less than 1.4, less than 1.25, or even less than 1.1.

In some embodiments, the third fibrous material is passed through a third screen to produce a fourth fibrous material. The fourth fibrous material can be, e.g., passed through a fourth screen to produce a fifth material. Similar screening processes can be repeated as many times as desired to produce the desired fibrous material having the desired properties.

Densification

Densified materials can be processed by any of the methods described herein, or any material described herein, e.g., any fibrous material described herein, can be processed by any one or more methods described herein, and then densified as described herein.

A material, e.g., a fibrous material, having a low bulk density can be densified to a product having a higher bulk density. For example, a material composition having a bulk density of 0.05 $g/cm^3$ can be densified by sealing the fibrous material in a relatively gas impermeable structure, e.g., a bag made of polyethylene or a bag made of alternating layers of polyethylene and a nylon, and then evacuating the entrapped gas, e.g., air, from the structure. After evacuation of the air from the structure, the fibrous material can have, e.g., a bulk density of greater than 0.3 $g/cm^3$, e.g., 0.5 $g/cm^3$, 0.6 $g/cm^3$, 0.7 $g/cm^3$ or more, e.g., 0.85 $g/cm^3$. After densification, the product can processed by any of the methods described herein, e.g., irradiated, e.g., with gamma radiation. This can be advantageous when it is desirable to transport the material to another location, e.g., a remote manufacturing plant, where the fibrous material composition can be added to a solution, e.g., to produce ethanol. After piercing the substantially gas impermeable structure, the densified fibrous material can revert to nearly its initial bulk density, e.g., greater than 60 percent of its initial bulk density, e.g., 70 percent, 80 percent, 85 percent or more, e.g., 95 percent of its initial bulk density. To reduce static electricity in the fibrous material, an antistatic agent can be added to the material.

In some embodiments, the structure, e.g., bag, is formed of a material that dissolves in a liquid, such as water. For example, the structure can be formed from a polyvinyl alcohol so that it dissolves when in contact with a water-based system. Such embodiments allow densified structures to be added directly to solutions that include a microorganism, without first releasing the contents of the structure, e.g., by cutting.

Figure 5:
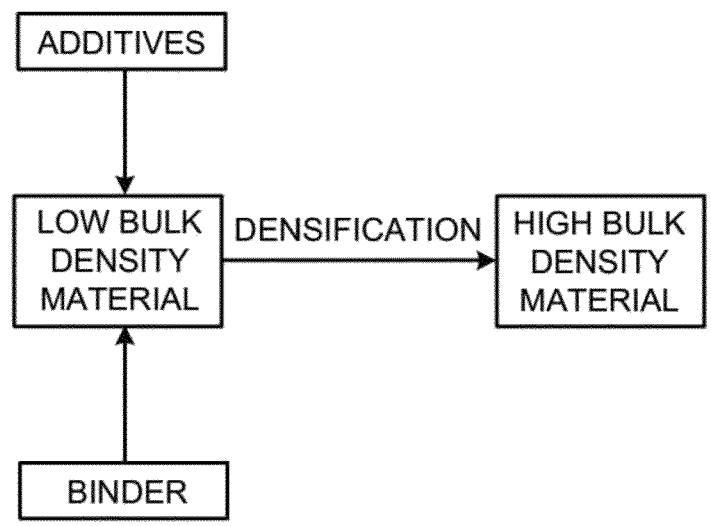
FIG. 5 is block diagram illustrating densification of a material.

Referring to FIG. 5, a biomass material can be combined with any desired additives and a binder, and subsequently densified by application of pressure, e.g., by passing the material through a nip defined between counter-rotating pressure rolls or by passing the material through a pellet mill. During the application of pressure, heat can optionally be applied to aid in the densification of the fibrous material. The densified material can then be irradiated.

In some embodiments, the material prior to densification has a bulk density of less than 0.25 g/cm$^3$, e.g., 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

The preferred binders include binders that are soluble in water, swollen by water, or that has a glass transition temperature of less 25° C., as determined by differential scanning calorimetry. By water-soluble binders, we mean binders having a solubility of at least about 0.05 weight percent in water. By water swellable binders, we mean binders that increase in volume by more than 0.5 percent upon exposure to water.

In some embodiments, the binders that are soluble or swollen by water include a functional group that is capable of forming a bond, e.g., a hydrogen bond, with the fibers of the fibrous material, e.g., cellulosic fibrous material. For example, the functional group can be a carboxylic acid group, a carboxylate group, a carbonyl group, e.g., of an aldehyde or a ketone, a sulfonic acid group, a sulfonate group, a phosphoric acid group, a phosphate group, an amide group, an amine group, a hydroxyl group, e.g., of an alcohol, and combinations of these groups, e.g., a carboxylic acid group and a hydroxyl group. Specific monomeric examples include glycerin, glyoxal, ascorbic acid, urea, glycine, pentaerythritol, a monosaccharide or a disaccharide, citric acid, and tartaric acid. Suitable saccharides include glucose, sucrose, lactose, ribose, fructose, mannose, arabinose and erythrose. Polymeric examples include polyglycols, polyethylene oxide, polycarboxylic acids, polyamides, polyamines and polysulfonic acids polysulfonates. Specific polymeric examples include polypropylene glycol (PPG), polyethylene glycol (PEG), polyethylene oxide, e.g., POLYOX®, copolymers of ethylene oxide and propylene oxide, polyacrylic acid (PAA), polyacrylamide, polypeptides, polyethylenimine, polyvinylpyridine, poly(sodium-4-styrenesulfonate) and poly(2-acrylamido-methyl-1-propanesulfonic acid).

In some embodiments, the binder includes a polymer that has a glass transition temperature less than 25° C. Examples of such polymers include thermoplastic elastomers (TPEs). Examples of TPEs include polyether block amides, such as those available under the tradename PEBAX®, polyester elastomers, such as those available under the tradename HYTREL®, and styrenic block copolymers, such as those available under the tradename KRATON®. Other suitable polymers having a glass transition temperature less than 25° C. include ethylene vinyl acetate copolymer (EVA), polyolefins, e.g., polyethylene, polypropylene, ethylene-propylene copolymers, and copolymers of ethylene and alpha olefins, e.g., 1-octene, such as those available under the tradename ENGAGE®. In some embodiments, e.g., when the material is a fiberized polycoated paper, the material is densified without the addition of a separate low glass transition temperature polymer.

In a particular embodiment, the binder is a lignin, e.g., a natural or synthetically modified lignin.

A suitable amount of binder added to the material, calculated on a dry weight basis, is, e.g., from about 0.01 percent to about 50 percent, e.g., 0.03 percent, 0.05 percent, 0.1 percent, 0.25 percent, 0.5 percent, 1.0 percent, 5 percent, 10 percent or more, e.g., 25 percent, based on a total weight of the densified material. The binder can be added to the material as a neat, pure liquid, as a liquid having the binder dissolved therein, as a dry powder of the binder, or as pellets of the binder.

Figure 6:
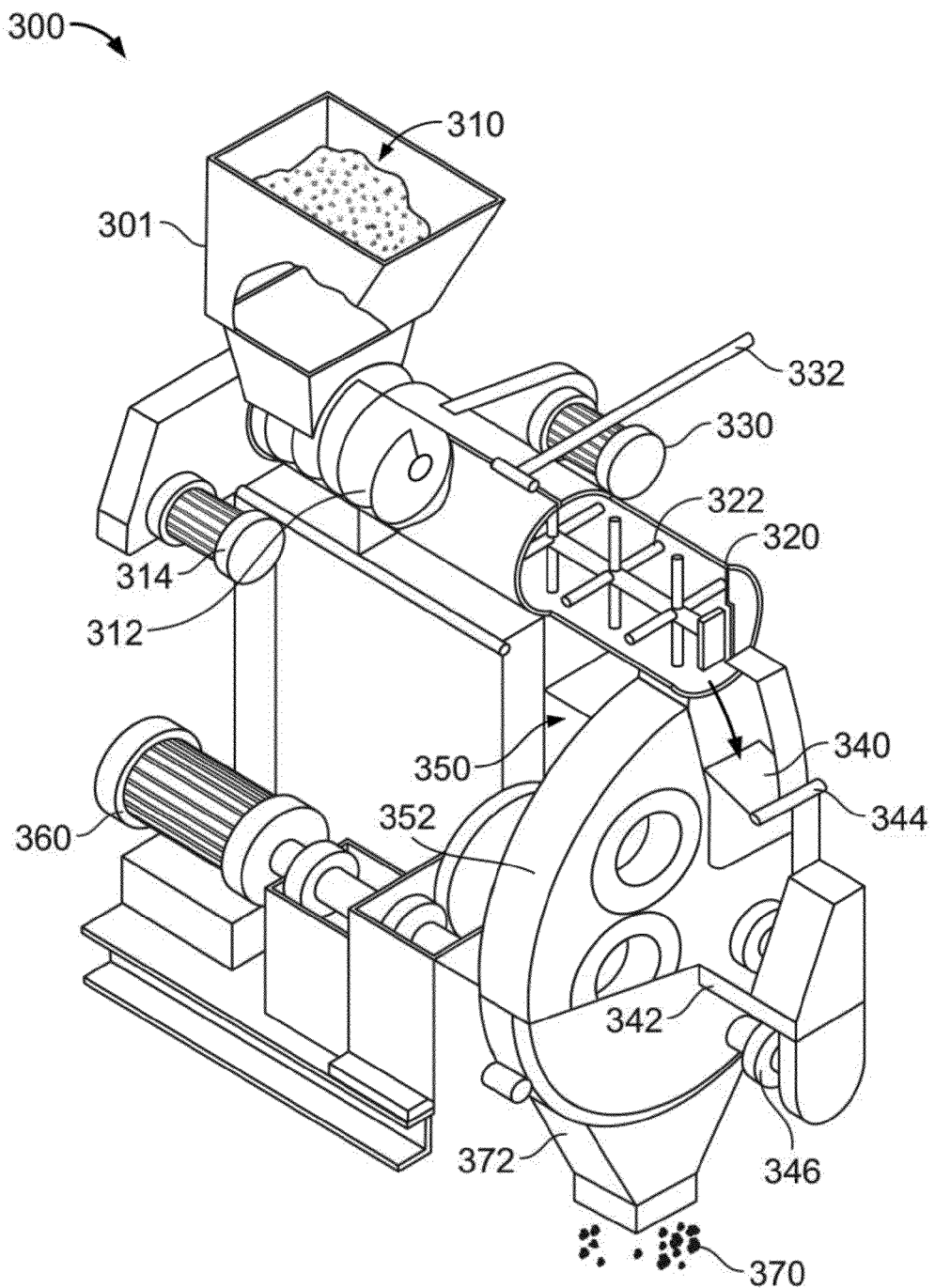
FIG. 6 is a perspective view of a pellet mill.

The densified fibrous material can be made in a pellet mill. Referring to FIG. 6, a pellet mill 300 has a hopper 301 for holding undensified material 310 that includes carbohydrate-containing materials, such as cellulose. The hopper communicates with an auger 312 that is driven by variable speed motor 314 so that undensified material can be transported to a conditioner 320 that stirs the undensified material with paddles 322 that are rotated by conditioner motor 330. Other ingredients, e.g., any of the additives and/or fillers described herein, can be added at inlet 332. If desired, heat may be added while the fibrous material is in the conditioner. After being conditioned, the material passes from the conditioner through a dump chute 340, and to another auger 342. The dump chute, as controlled by actuator 344, allows for unobstructed passage of the material from conditioner to auger. Auger is rotated by motor 346, and controls the feeding of the fibrous material into die and roller assembly 350. Specifically, the material is introduced into a hollow, cylindrical die 352, which rotates about a horizontal axis and which has radially extending die holes 250. Die 352 is rotated about the axis by motor 360, which includes a horsepower gauge, indicating total power consumed by the motor. Densified material 370, e.g., in the form of pellets, drops from chute 372 and are captured and processed, such as by irradiation.

The material, after densification, can be conveniently in the form of pellets or chips having a variety of shapes. The pellets can then be irradiated. In some embodiments, the pellets or chips are cylindrical in shape, e.g., having a maximum transverse dimension of, e.g., 1 mm or more, e.g., 2 mm, 3 mm, 5 mm, 8 mm, 10 mm, 15 mm or more, e.g., 25 mm. Other convenient shapes include pellets or chips that are plate-like in form, e.g., having a thickness of 1 mm or more, e.g., 2 mm, 3 mm, 5 mm, 8 mm, 10 mm or more, e.g., 25 mm; a width of, e.g., 5 mm or more, e.g., 10 mm, 15 mm, 25 mm, 30 mm or more, e.g., 50 mm; and a length of 5 mm or more, e.g., 10 mm, 15 mm, 25 mm, 30 mm or more, e.g., 50 mm.

Figure 7A:
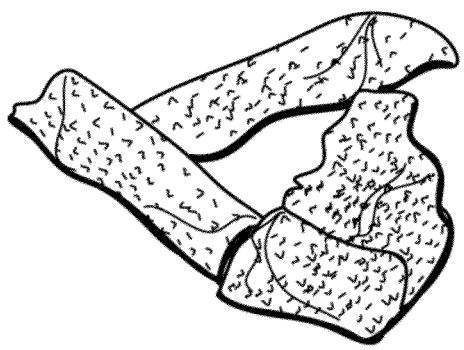
FIG. 7A is a densified fibrous material in pellet form.
Figure 7B:
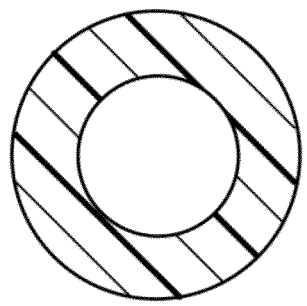
FIG. 7B is a transverse cross-section of a hollow pellet in which a center of the hollow is in-line with a center of the pellet.
Figure 7C:
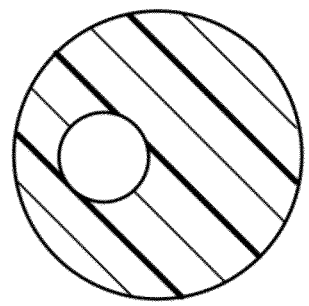
FIG. 7C is a transverse cross-section of a hollow pellet in which a center of the hollow is out of line with the center of the pellet.

Referring now FIG. 7A-7D, pellets can be made so that they have a hollow inside. As shown, the hollow can be generally in-line with the center of the pellet (FIG. 7B), or out of line with the center of the pellet (FIG. 7C). Making the pellet hollow inside can increase the rate of dissolution in a liquid after irradiation.

Figure 7D:
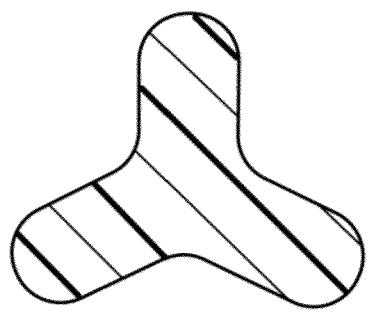
FIG. 7D is a transverse cross-section of a tri-lobal pellet.

Referring now to FIG. 7D, the pellet can have, e.g., a transverse shape that is multi-lobal, e.g., tri-lobal as shown, or tetra-lobal, penta-lobal, hexa-lobal or deca-lobal. Making the pellets in such transverse shapes can also increase the rate of dissolution in a solution after irradiation.

Alternatively, the densified material can be in any other desired form, e.g., the densified material can be in the form of a mat, roll or bale.

EXAMPLES

In one example, half-gallon juice cartons made of unprinted white Kraft board having a bulk density of 20 lb/ft$^3$ can be used as a feedstock. Cartons can be folded flat and then fed into a shredder to produce a confetti-like material having a width of between 0.1 inch and 0.5 inch, a length of between 0.25 inch and 1 inch and a thickness equivalent to that of the starting material (about 0.075 inch). The confetti-like material can be fed to a rotary knife cutter, which shears the confetti-like pieces, tearing the pieces apart and releasing fibrous material.

In some cases, multiple shredder-shearer trains can be arranged in series with output. In one embodiment, two shredder-shearer trains can be arranged in series with output from the first shearer fed as input to the second shredder. In another embodiment, three shredder-shearer trains can be arranged in series with output from the first shearer fed as input to the second shredder and output from the second shearer fed as input to the third shredder. Multiple passes through shredder-shearer trains are anticipated to decrease particle size and increase overall surface area within the feedstream.

In another example, fibrous material produced from shredding and shearing juice cartons can be treated to increase its bulk density. In some cases, the fibrous material can be sprayed with water or a dilute stock solution of POLYOX™ WSR N10 (polyethylene oxide) prepared in water. The wetted fibrous material can then be processed through a pellet mill operating at room temperature. The pellet mill can increase the bulk density of the feedstream by more than an order of magnitude.

Pretreatment

Physically prepared feedstock can be pretreated for use in primary production processes by, for example, reducing the average molecular weight and crystallinity of the feedstock and/or increasing the surface area and/or porosity of the feedstock.

In some embodiments, the cellulosic and/or lignocellulosic material includes a first cellulose having a first number average molecular weight and the resulting carbohydrate includes a second cellulose having a second number average molecular weight lower than the first number average molecular weight. For example, the second number average molecular weight is lower than the first number average molecular weight by more than about twenty-five percent, e.g., 2×, 3×, 5×, 7×, 10×, 25×, even 100× reduction.

In some embodiments, the first cellulose has a first crystallinity and the second cellulose has a second crystallinity lower than the first crystallinity, such as lower than about two, three, five, ten, fifteen or twenty-five percent lower.

In some embodiments, the first cellulose has a first level of oxidation and the second cellulose has a second level of oxidation higher than the first level of oxidation, such as two, three, four, five, ten or even twenty-five percent higher.

Pretreatment processes can include one or more of irradiation, sonication, oxidation, pyrolysis, and steam explosion. The various pretreatment systems and methods can be used in combinations of two, three, or even four of these technologies.

Pretreatment Combinations

In some embodiments, biomass can be processed by applying two or more of any of the processes described herein, such as two, three, four or more of radiation, sonication (or any other disruption technique described herein, e.g., treatment with a rotor-stator disruptor), oxidation, pyrolysis, and steam explosion either with or without prior, intermediate, or subsequent feedstock preparation as described herein. The processes can be applied to the biomass in any order or concurrently. For example, a carbohydrate can be prepared by applying radiation, sonication, oxidation, pyrolysis, and, optionally, steam explosion to a cellulosic and/or lignocellulosic material (in any order or concurrently). The provided carbohydrate-containing material can then be converted by one or more microorganisms, such as bacteria, yeast, or mixtures of yeast and bacteria, to a number of desirable products, as described herein. Multiple processes can provide materials that can be more readily utilized by a variety of microorganisms because of their lower molecular weight, lower crystallinity, and/or enhanced solubility. Multiple processes can provide synergies and can reduce overall energy input required in comparison to any single process.

For example, in some embodiments, feedstocks are provided that include a carbohydrate that is produced by a process that includes irradiating and sonicating, irradiating and oxidizing, irradiating and pyrolyzing, or irradiating and steam-exploding (in either order or concurrently) a cellulosic and/or a lignocellulosic material. The provided feedstock can then be contacted with a microorganism having the ability to convert at least a portion, e.g., at least about 1 percent by weight, of the feedstock to the product, such as the combustible fuel.

Pretreatment Conditions

In some embodiments, the process does not include hydrolyzing the cellulosic and/or lignocellulosic material, such as with an acid, e.g., a mineral acid, such as hydrochloric or sulfuric acid, an enzyme or a base. If desired, some or none of the feedstock can include a hydrolyzed material. For example, in some embodiments, at least about seventy percent by weight of the feedstock is an unhydrolyzed material, e.g., at least at 95 percent by weight of the feedstock is an unhydrolyzed material. In some embodiments, substantially all of the feedstock is an unhydrolyzed material. For example, treatment with alkali can be avoided.

Any feedstock or any reactor or fermentor charged with a feedstock can include a buffer, such as sodium bicarbonate, ammonium chloride or Tris; an electrolyte, such as potassium chloride, sodium chloride, or calcium chloride; a growth factor, such as biotin and/or a base pair such as uracil or an equivalent thereof; a surfactant, such as Tween® or polyethylene glycol; a mineral, such as such as calcium, chromium, copper, iodine, iron, selenium, or zinc; or a chelating agent, such as ethylene diamine, ethylene diamine tetraacetic acid (EDTA) (or its salt form, e.g., sodium or potassium EDTA), or dimercaprol.

When radiation is utilized, it can be applied to any sample that is dry or wet, or even dispersed in a liquid, such as water. For example, irradiation can be performed on cellulosic and/or lignocellulosic material in which less than about 25 percent by weight of the cellulosic and/or lignocellulosic material has surfaces wetted with a liquid, such as water. In some embodiments, irradiating is performed on cellulosic and/or lignocellulosic material in which substantially none of the cellulosic and/or lignocellulosic material is wetted with a liquid, such as water.

In some embodiments, any processing described herein occurs with the cellulosic and/or lignocellulosic material remaining dry as acquired or after the material has been dried, e.g., using heat and/or reduced pressure. For example, in some embodiments, the cellulosic and/or lignocellulosic material has less than about five percent by weight retained water, measured at 25° C. and at fifty percent relative humidity.

The feedstock can be treated so that it has a low moisture content, e.g., less than about 7.5, 5, 3, 2.5, 2, 1.5, 1, or 0.5% by weight. This material can be irradiated with a beam of particles, such as electrons or protons. The irradiation can be immediately following preparation of the material or after a moisture reduction step, e.g., drying at approximately 105° C. for 4-18 hours.

If desired, a swelling agent, as defined herein, can be utilized in any process described herein. In some embodiments, when a cellulosic and/or lignocellulosic material is processed using radiation, less than about 25 percent by weight of the cellulosic and/or lignocellulosic material is in a swollen state, the swollen state being characterized as having a volume of more than about 2.5 percent higher than an unswollen state, e.g., more than 5.0, 7.5, 10, or 15 percent higher than the unswollen state. In specific embodiments when radiation is utilized, the cellulosic and/or lignocellulosic material includes a swelling agent, and swollen cellulosic and/or lignocellulosic receives a dose of less than about 10 Mrad. In other embodiments, when radiation is utilized on a cellulosic and/or lignocellulosic material, substantially none of the cellulosic and/or lignocellulosic material is in a swollen state.

In some embodiments, no chemicals, e.g., no swelling agents, are added to the biomass prior to irradiation. For example, in some of these embodiments no alkaline substances (such as sodium hydroxide, potassium hydroxide, lithium hydroxide and ammonium hydroxides), acidifying agents (such as mineral acids (e.g., sulfuric acid, hydrochloric acid and phosphoric acid)), salts, such as zinc chloride, calcium carbonate, sodium carbonate, benzyltrimethylammonium sulfate, or basic organic amines, such as ethylene diamine, are added prior to irradiation or other processing. In some cases, no additional water is added. For example, the biomass prior to processing can have less than 0.5 percent by weight added chemicals, e.g., less than 0.4, 0.25, 0.15 or 0.1 percent by weight added chemicals. In some instances, the biomass has no more than a trace, e.g., less than 0.05 percent by weight added chemicals, prior to irradiation. In other instances, the biomass prior to irradiation has substantially no added chemicals or swelling agents. Avoiding the use of such chemicals can also be extended throughout processing, e.g., at all times prior to fermentation, or at all times.

When radiation is utilized in any process, it can be applied while the cellulosic and/or lignocellulosic is exposed to air, oxygen-enriched air, or even oxygen itself, or blanketed by an inert gas such as nitrogen, argon, or helium. When maximum oxidation is desired, an oxidizing environment is utilized, such as air or oxygen. The distance from the radiation source can also be optimized to maximize reactive gas formation, e.g., ozone and/or oxides of nitrogen.

When radiation is utilized, it may be applied to biomass, such as cellulosic and/or lignocellulosic material, under a pressure of greater than about 2.5 atmospheres, such as greater than 5, 10, 15, 20 or even greater than about 50 atmospheres.

When the process includes radiation, the irradiating can be performed utilizing an ionizing radiation, such as gamma rays, x-rays, energetic ultraviolet radiation, such as ultraviolet C radiation having a wavelength of from about 100 nm to about 280 nm, a beam of particles, such as a beam of electrons, slow neutrons or alpha particles. In some embodiments, irradiating includes two or more radiation sources, such as gamma rays and a beam of electrons, which can be applied in either order or concurrently.

Any processing technique described herein can be used at a pressure above or below normal, earth-bound atmospheric pressure. For example, any process that utilizes radiation, sonication, oxidation, pyrolysis, steam explosion, or combinations of any of these processes to provide materials that include a carbohydrate can be performed under high pressure, which can increase reaction rates. For example, any process or combination of processes can be performed at a pressure greater than about normal atmospheric pressure, e.g., at a pressure of greater than about 25 MPa, e.g., greater than 50 MPa, 75 MPa, 100 MPa, 150 MPa, 200 MPa, 250 MPa, 350 MPa, 500 MPa, 750 MPa, 1,000 MPa, or greater than 1,500 MPa.

Radiation Treatment

One or more irradiation processing sequences can be used to process raw feedstock from a wide variety of different sources to extract useful substances from the feedstock, and to provide partially degraded organic material which functions as input to further processing steps and/or sequences. Irradiation can reduce the molecular weight and/or crystallinity of feedstock. In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. The doses applied depend on the desired effect and the particular feedstock. For example, high doses of radiation can break chemical bonds within feedstock components and low doses of radiation can increase chemical bonding (e.g., cross-linking) within feedstock components. In some instances when chain scission is desirable and/or polymer chain functionalization is desirable, particles heavier than electrons, such as protons, helium nuclei, argon ions, silicon ions, neon ions carbon ions, phoshorus ions, oxygen ions or nitrogen ions can be utilized. When ring-opening chain scission is desired, positively charged particles can be utilized for their Lewis acid properties for enhanced ring-opening chain scission. For example, when oxygen-containing functional groups are desired, irradiation in the presence of oxygen or even irradiation with oxygen ions can be performed. For example, when nitrogen-containing functional groups are desirable, irradiation in the presence of nitrogen or even irradiation with nitrogen ions can be performed.

Figure 8:
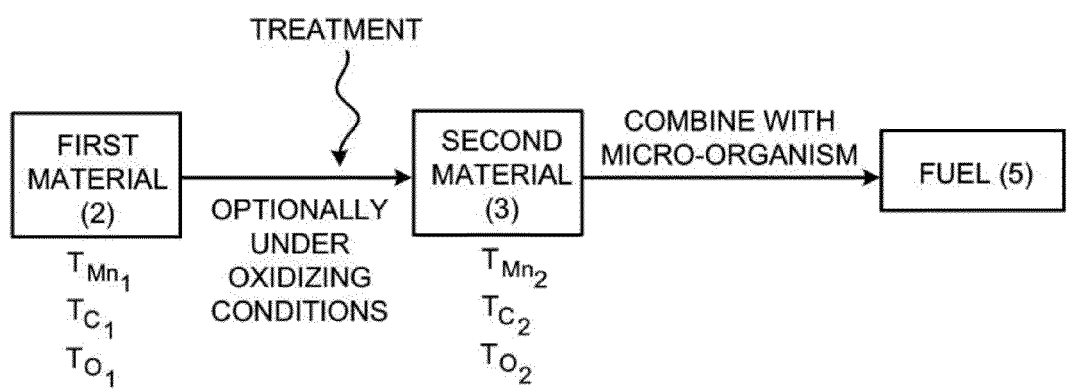
FIG. 8 is a block diagram illustrating a treatment sequence for processing feedstock.

Referring to FIG. 8, in one method, a first material 2 that is or includes cellulose having a first number average molecular weight ($^T M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material 3 that includes cellulose having a second number average molecular weight ($^T M_{N2}$) lower than the first number average molecular weight. The second material (or the first and second material) can be combined with a microorganism (e.g., a bacterium or a yeast) that can utilize the second and/or first material to produce a product, e.g., a fuel 5 that is or includes hydrogen, an alcohol (e.g., ethanol or butanol, such as n-, sec- or t-butanol), an organic acid, a hydrocarbon or mixtures of any of these.

Since the second material 3 has cellulose having a reduced molecular weight relative to the first material, and in some instances, a reduced crystallinity as well, the second material is generally more dispersible, swellable and/or soluble in a solution containing a microorganism. These properties make the second material 3 more susceptible to chemical, enzymatic and/or biological attack relative to the first material 2, which can greatly improve the production rate and/or production level of a desired product, e.g., ethanol. Radiation can also sterilize the materials.

In some embodiments, the second number average molecular weight ($M_{n2}$) is lower than the first number average molecular weight ($^T M_{n1}$) by more than about 10 percent, e.g., 15, 20, 25, 30, 35, 40, 50 percent, 60 percent, or even more than about 75 percent.

In some instances, the second material has cellulose that has as crystallinity ($^T C_2$) that is lower than the crystallinity ($^T C_1$) of the cellulose of the first material. For example, ($^T C_2$) can be lower than ($^T C_1$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($^T O_2$) that is higher than the level of oxidation ($^T O_1$) of the first material. A higher level of oxidation of the material can aid in its dispersibility, swellability and/or solubility, further enhancing the materials susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the biomass via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, a copy of which is included as Appendix B of U.S. Pat. No. 8,212,087; Chu, William T., "Overview of Light-Ion Beam Therapy", Columbus-Ohio, ICRU-IAEA Meeting, 18-20 March 2006, a copy of which is included as Appendix C of U.S. Pat. No. 8,212,087; Iwata, Y. et al., "Alternating-Phase-Focused IH-DTL for Heavy-Ion Medical Accelerators", Proceedings of EPAC 2006, Edinburgh, Scotland, a copy of which is included as Appendix D of U.S. Pat. No. 8,212,087, and Leitner, C. M. et al., "Status of the Superconducting ECR Ion Source Venus", Proceedings of EPAC 2000, Vienna, Austria, a copy of which is included as Appendix E of U.S. Pat. No. 8,212,087.

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient.

Electromagnetic radiation is subclassified as gamma rays, x rays, ultraviolet rays, infrared rays, microwaves, or radiowaves, depending on its wavelength.

Figure 9:
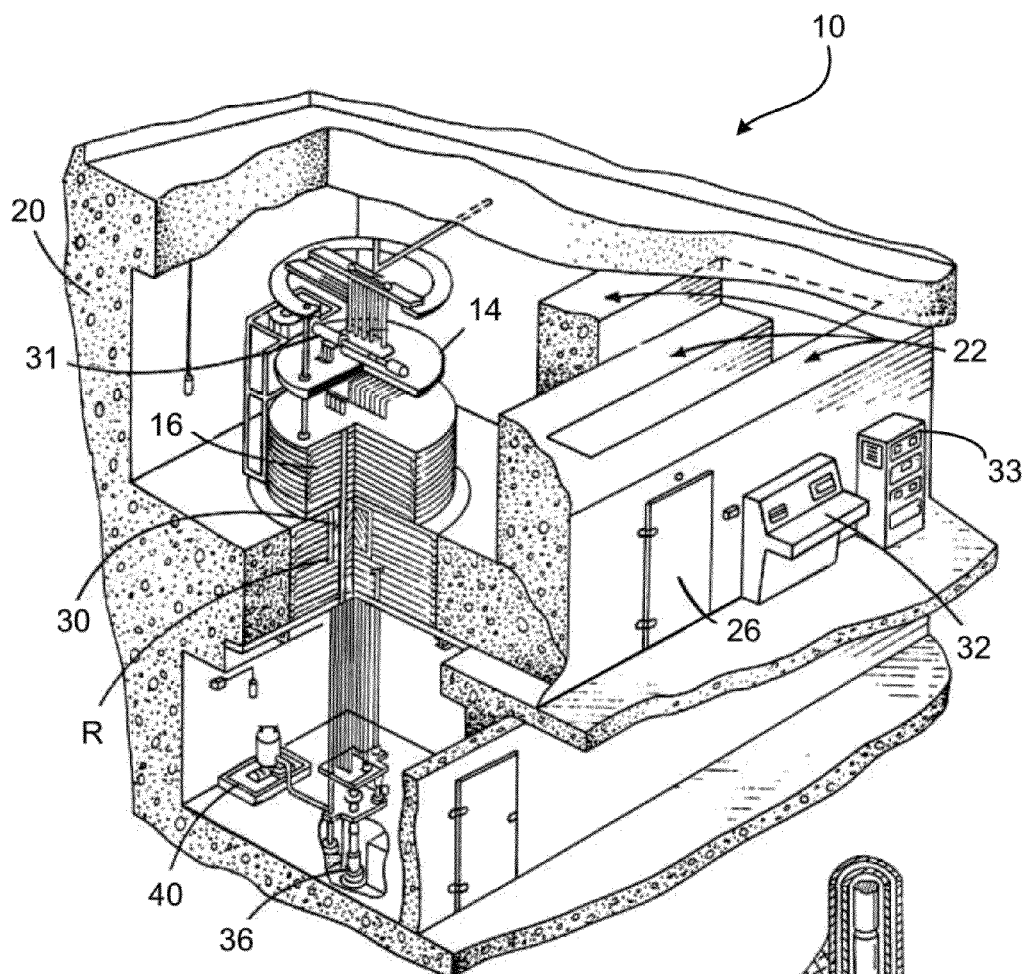
FIG. 9 is a perspective, cut-away view of a gamma irradiator housed in a concrete vault.
Figure 10:
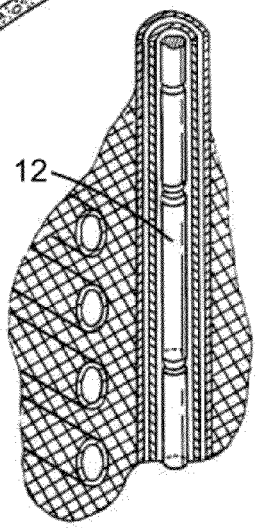
FIG. 10 is an enlarged perspective view of region R of FIG. 9.

For example, gamma radiation can be employed to irradiate the materials. Referring to FIGS. 9 and 10 (an enlarged view of region R), a gamma irradiator 10 includes gamma radiation sources 408, e.g., $^{60}$Co pellets, a working table 14 for holding the materials to be irradiated and storage 16, e.g., made of a plurality iron plates, all of which are housed in a concrete containment chamber (vault) 20 that includes a maze entranceway 22 beyond a lead-lined door 26. Storage 16 includes a plurality of channels 30, e.g., sixteen or more channels, allowing the gamma radiation sources to pass through storage on their way proximate the working table.

In operation, the sample to be irradiated is placed on a working table. The irradiator is configured to deliver the desired dose rate and monitoring equipment is connected to an experimental block 31. The operator then leaves the containment chamber, passing through the maze entranceway and through the lead-lined door. The operator mans a control panel 32, instructing a computer 33 to lift the radiation sources 12 into working position using cylinder 36 attached to a hydraulic pump 40.

Gamma radiation has the advantage of a significant penetration depth into a variety of material in the sample. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Provisional Application Ser. No. 61/073,665, the complete disclosure of which is incorporated herein by reference.

Electron Beam

In some embodiments, a beam of electrons is used as the radiation source. A beam of electrons has the advantages of high dose rates (e.g., 1, 5, or even 10 Mrad per second), high throughput, less containment, and less confinement equipment. Electron beams can also have up to 80 percent electrical efficiency, allowing for a low energy usage, which can translate into a low cost of operation and low greenhouse gas emissions corresponding to the small amount of energy used. Electrons can also be more efficient at causing chain scission. In addition, electrons having energies of 4-10 MeV can have a penetration depth of 5 to 30 mm or more, such as 40 mm. In low bulk density materials, such as many of the materials described herein, e.g., materials having a bulk density of less than about 0.5 g/cm$^3$, electrons having energies in the 4-10 MeV range can penetrate 4-8 inches or even more.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Figure 11:
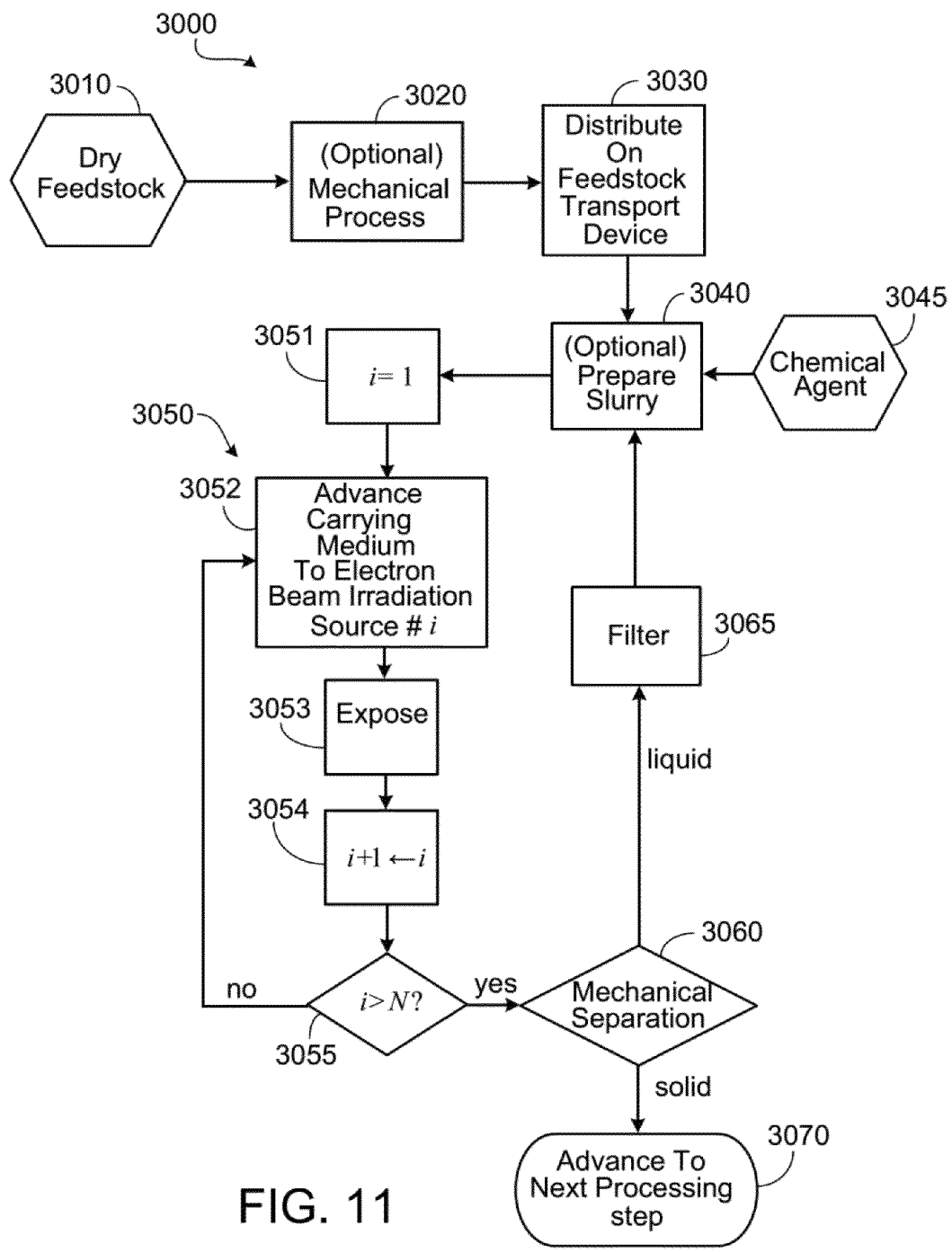
FIG. 11 is a block diagram illustrating an electron beam irradiation feedstock pretreatment sequence.

FIG. 11 shows a process flow diagram 3000 that includes various steps in an electron beam irradiation feedstock pretreatment sequence. In first step 3010, a supply of dry feedstock is received from a feed source. As discussed above, the dry feedstock from the feed source may be pre-processed prior to delivery to the electron beam irradiation devices. For example, if the feedstock is derived from plant sources, certain portions of the plant material may be removed prior to collection of the plant material and/or before the plant material is delivered by the feedstock transport device. Alternatively, or in addition, as expressed in optional step 3020, the biomass feedstock can be subjected to mechanical processing (e.g., to reduce the average length of fibers in the feedstock) prior to delivery to the electron beam irradiation devices.

In step 3030, the dry feedstock is transferred to a feedstock transport device (e.g., a conveyor belt) and is distributed over the cross-sectional width of the feedstock transport device approximately uniformly by volume. This can be accomplished, for example, manually or by inducing a localized vibration motion at some point in the feedstock transport device prior to the electron beam irradiation processing.

In some embodiments, a mixing system introduces a chemical agent 3045 into the feedstock in an optional process 3040 that produces a slurry. Combining water with the processed feedstock in mixing step 3040 creates an aqueous feedstock slurry that may be transported through, for example, piping rather than using, for example, a conveyor belt.

The next step 3050 is a loop that encompasses exposing the feedstock (in dry or slurry form) to electron beam radiation via one or more (say, N) electron beam irradiation devices. The feedstock slurry is moved through each of the N "showers" of electron beams at step 3052. The movement may either be at a continuous speed through and between the showers, or there may be a pause through each shower, followed by a sudden movement to the next shower. A small slice of the feedstock slurry is exposed to each shower for some predetermined exposure time at step 3053.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. Effectiveness of depolymerization of the feedstock slurry depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete. Tradeoffs in considering electron energies include energy costs; here, a lower electron energy may be advantageous in encouraging depolymerization of certain feedstock slurry (see, for example, Bouchard, et al, Cellulose (2006) 13: 601-610).

It may be advantageous to provide a double-pass of electron beam irradiation in order to provide a more effective depolymerization process. For example, the feedstock transport device could direct the feedstock (in dry or slurry form) underneath and in a reverse direction to its initial transport direction. Double-pass systems can allow thicker feedstock slurries to be processed and can provide a more uniform depolymerization through the thickness of the feedstock slurry.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available.

Once a portion of feedstock slurry has been transported through the N electron beam irradiation devices, it may be necessary in some embodiments, as in step 3060, to mechanically separate the liquid and solid components of the feedstock slurry. In these embodiments, a liquid portion of the feedstock slurry is filtered for residual solid particles and recycled back to the slurry preparation step 3040. A solid portion of the feedstock slurry is then advanced on to the next processing step 3070 via the feedstock transport device. In other embodiments, the feedstock is maintained in slurry form for further processing.

Heavy Ion Particle Beams

Particles heavier than electrons can be utilized to irradiate carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phosphorus ions, oxygen ions or nitrogen ions can be utilized. In some embodiments, particles heavier than electrons can induce higher amounts of chain scission. In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

Doses

In some embodiments, the irradiating (with any radiation source or a combination of sources) is performed until the material receives a dose of at least 0.05 Mrad, e.g., at least 0.1, 0.25, 1.0, 2.5, 5.0, or 10.0 Mrad. In some embodiments, the irradiating is performed until the material receives a dose of between 1.0 Mrad and 6.0 Mrad, e.g., between 1.5 Mrad and 4.0 Mrad. In other embodiments, irradiating is performed at a dose between about 0.1 MRad and about 10 MRad, e.g., between about 0.25 MRad and about 9 MRad, between about 0.5 MRad and about 7.5 MRad or between about 0.75 MRad and about 5 MRad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

In one example of the use of radiation as a pretreatment, half-gallon juice cartons made of un-printed polycoated white Kraft board having a bulk density of 20 lb/ft$^3$ are used as a feedstock. Cartons are folded flat and then fed into a sequence of three shredder-shearer trains arranged in series with output from the first shearer fed as input to the second shredder, and output from the second shearer fed as input to the third shredder. The fibrous material produced by the shredder-shearer train can be sprayed with water and processed through a pellet mill operating at room temperature. The densified pellets can be placed in a glass ampoule which is evacuated under high vacuum and then back-filled with argon gas. The ampoule is sealed under argon. Alternatively, in another example, the ampoule is sealed under an atmosphere of air. The pellets in the ampoule are irradiated with gamma radiation for about 3 hours at a dose rate of about 1 Mrad per hour to provide an irradiated material in which the cellulose has a lower molecular weight than the starting material.

Additives to Enhance Molecular Weight Breakdown During Irradiation

In some embodiments, prior to irradiation, various materials, e.g., solids or liquids, can be added to the biomass to enhance molecular weight reduction. In those instances in which a liquid is utilized, the liquid can be in contact with outer surfaces of the biomass and/or the liquid can be in interior portions of the biomass, e.g., infused into the biomass.

For example, the material can be a neutral weak base, such as alanine, ammonia, ammonia/water mixture, e.g., 25 percent by weight ammonia in water, water, methyl amine, dimethyl amine, trimethyl amine, pyridine, or a anionic base, such as a salt of acetic acid (e.g., sodium acetate), sodium carbonate, sodium bicarbonate or a salt of an ion of hydrogen sulfide (e.g., sodium hydrosulfide).

Alternatively, the material can be a neutral weak acid, such as formic acid, acetic acid, trichloroacetic acid, water, hydrogen sulfide or a cationic acid, such as an ammonium salt.

Quenching and Controlled Functionalization of Biomass

After treatment with one or more ionizing radiations, such as photonic radiation (e.g., X-rays or gamma-rays), e-beam radiation or particles heavier than electrons that are positively or negatively charged (e.g., protons or carbon ions), any of the carbohydrate-containing materials or mixtures described herein become ionized; that is, they include radicals at levels that are detectable with an electron spin resonance spectrometer. The current limit of detection of the radicals is about $10^{14}$ spins at room temperature. After ionization, any biomass material that has been ionized can be quenched to reduce the level of radicals in the ionized biomass, e.g., such that the radicals are no longer detectable with the electron spin resonance spectrometer. For example, the radicals can be quenched by the application of a sufficient pressure to the biomass and/or by utilizing a fluid in contact with the ionized biomass, such as a gas or liquid, that reacts with (quenches) the radicals. Using a gas or liquid to at least aid in the quenching of the radicals can be used to functionalize the ionized biomass with a desired amount and kind of functional groups, such as carboxylic acid groups, enol groups, aldehyde groups, nitro groups, nitrile groups, amino groups, alkyl amino groups, alkyl groups, chloroalkyl groups or chlorofluoroalkyl groups. In some instances, such quenching can improve the stability of some of the ionized biomass materials. For example, quenching can improve the resistance of the biomass to oxidation. Functionalization by quenching can also improve the solubility of any biomass described herein, can improve its thermal stability, and can improve material utilization by various microorganisms. For example, the functional groups imparted to the biomass material by the quenching can act as receptor sites for attachment by microorganisms, e.g., to enhance cellulose hydrolysis by various microorganisms.

Figure 11A:
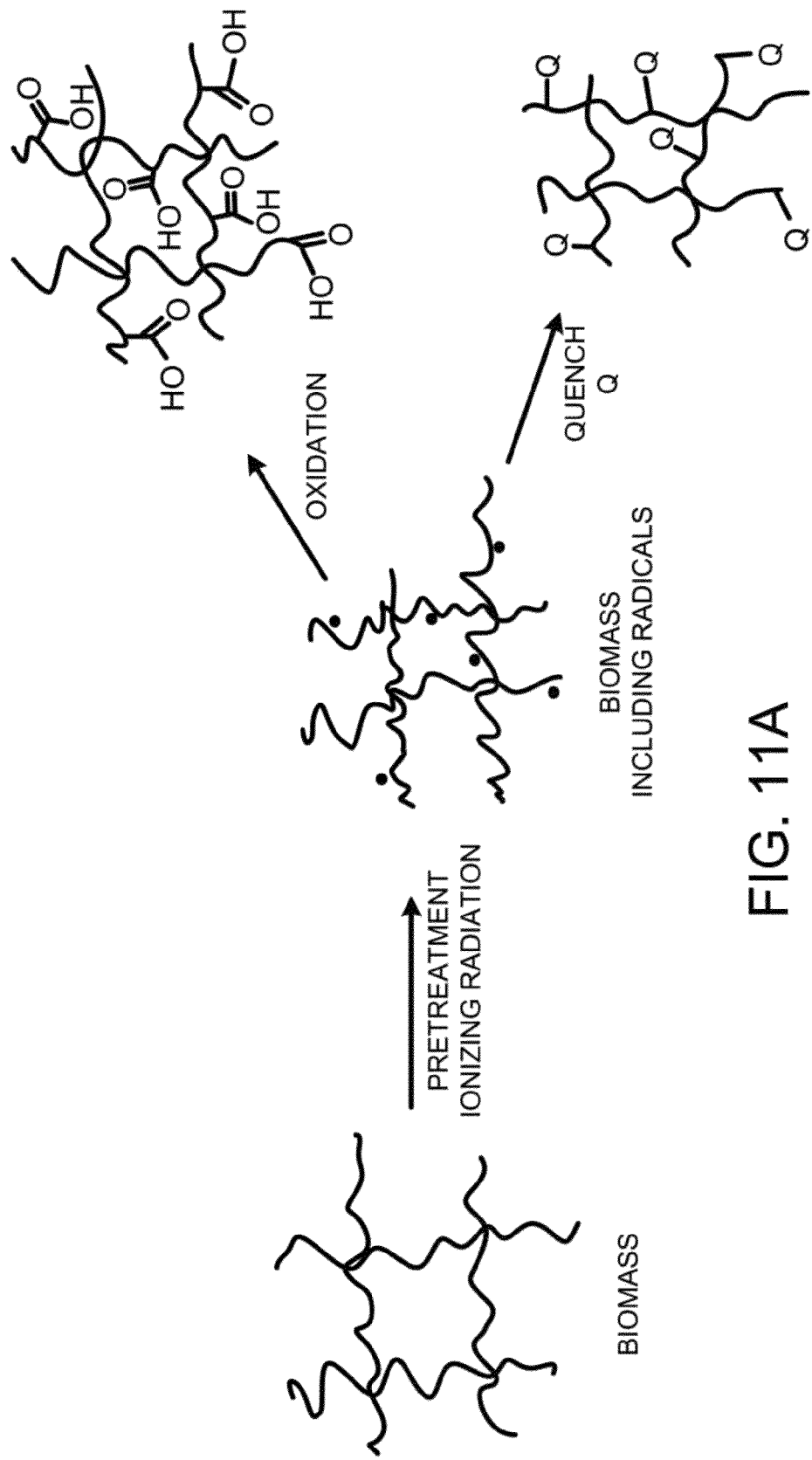
FIG. 11A is a schematic representation of biomass being ionized, and then oxidized or quenched.

FIG. 11A illustrates changing a molecular and/or a supramolecular structure of a biomass feedstock by pretreating the biomass feedstock with ionizing radiation, such as with electrons or ions of sufficient energy to ionize the biomass feedstock, to provide a first level of radicals. As shown in FIG. 11A, if ionized biomass remains in the atmosphere, it will be oxidized, such as to an extent that carboxylic acid groups are generated by reacting with the atmospheric oxygen. In some instances with some materials, such oxidation is desired because it can aid in the further breakdown in molecular weight of the carbohydrate-containing biomass, and the oxidation groups, e.g., carboxylic acid groups can be helpful for solubility and microorganism utilization in some instances. However, since the radicals can "live" for some time after irradiation, e.g., longer than 1 day, 5 days, 30 days, 3 months, 6 months or even longer than 1 year, materials properties can continue to change over time, which in some instances, can be undesirable. Detecting radicals in irradiated samples by electron spin resonance spectroscopy and radical lifetimes in such samples is discussed in Bartolotta et al., Physics in Medicine and Biology, 46 (2001), 461-471 and in Bartolotta et al., Radiation Protection Dosimetry, Vol. 84, Nos. 1-4, pp. 293-296 (1999) which are included as Appendix F and Appendix G, respectively, in U.S. Pat. No. 8,212,087. As shown in FIG. 11A, the ionized biomass can be quenched to functionalize and/or to stabilize the ionized biomass. At any point, e.g., when the material is "alive", "partially alive" or fully quenched, the pretreated biomass can be converted into a product, e.g., a fuel, a food, or a composite.

In some embodiments, the quenching includes an application of pressure to the biomass, such as by mechanically deforming the biomass, e.g., directly mechanically compressing the biomass in one, two, or three dimensions, or applying pressure to a fluid in which the biomass is immersed, e.g., isostatic pressing. In such instances, the deformation of the material itself brings radicals, which are often trapped in crystalline domains, in close enough proximity so that the radicals can recombine, or react with another group. In some instances, the pressure is applied together with the application of heat, such as a sufficient quantity of heat to elevate the temperature of the biomass to above a melting point or softening point of a component of the biomass, such as lignin, cellulose or hemicellulose. Heat can improve molecular mobility in the polymeric material, which can aid in the quenching of the radicals. When pressure is utilized to quench, the pressure can be greater than about 1000 psi, such as greater than about 1250 psi, 1450 psi, 3625 psi, 5075 psi, 7250 psi, 10000 psi or even greater than 15000 psi.

In some embodiments, quenching includes contacting the biomass with a fluid, such as a liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the biomass with a liquid, e.g., a liquid soluble in, or at least capable of penetrating into the biomass and reacting with the radicals, such as a diene, such as 1,5-cyclooctadiene. In some specific embodiments, the quenching includes contacting the biomass with an antioxidant, such as Vitamin E. If desired, the biomass feedstock can include an antioxidant dispersed therein, and the quenching can come from contacting the antioxidant dispersed in the biomass feedstock with the radicals.

Other methods for quenching are possible. For example, any method for quenching radicals in polymeric materials described in Muratoglu et al., U.S. Patent Application Publication No. 2008/0067724 and Muratoglu et al., U.S. Pat. No. 7,166,650, which are included as Appendix H and Appendix I, respectively, in U.S. Pat. No. 8,212,087, can be utilized for quenching any ionized biomass material described herein. Furthermore any quenching agent (described as a "sensitizing agent" in the above-noted Muratoglu disclosures) and/or any antioxidant described in either Muratoglu reference can be utilized to quench any ionized biomass material.

Functionalization can be enhanced by utilizing heavy charged ions, such as any of the heavier ions described herein. For example, if it is desired to enhance oxidation, charged oxygen ions can be utilized for the irradiation. If nitrogen functional groups are desired, nitrogen ions or anions that includes nitrogen can be utilized. Likewise, if sulfur or phosphorus groups are desired, sulfur or phosphorus ions can be used in the irradiation.

In some embodiments, after quenching any of the quenched ionized materials described herein can be further treated with one or more of radiation, such as ionizing or non-ionizing radiation, sonication, pyrolysis, and oxidation for additional molecular and/or supramolecular structure change.

Particle Beam Exposure in Fluids

In some cases, the cellulosic or lignocellulosic materials can be exposed to a particle beam in the presence of one or more additional fluids (e.g., gases and/or liquids). Exposure of a material to a particle beam in the presence of one or more additional fluids can increase the efficiency of the treatment.

In some embodiments, the material is exposed to a particle beam in the presence of a fluid such as air. Particles accelerated in any one or more of the types of accelerators disclosed herein (or another type of accelerator) are coupled out of the accelerator via an output port (e.g., a thin membrane such as a metal foil), pass through a volume of space occupied by the fluid, and are then incident on the material. In addition to directly treating the material, some of the particles generate additional chemical species by interacting with fluid particles (e.g., ions and/or radicals generated from various constituents of air, such as ozone and oxides of nitrogen). These generated chemical species can also interact with the material, and can act as initiators for a variety of different chemical bond-breaking reactions in the material. For example, any oxidant produced can oxidize the material, which can result in molecular weight reduction.

In certain embodiments, additional fluids can be selectively introduced into the path of a particle beam before the beam is incident on the material. As discussed above, reactions between the particles of the beam and the particles of the introduced fluids can generate additional chemical species, which react with the material and can assist in functionalizing the material, and/or otherwise selectively altering certain properties of the material. The one or more additional fluids can be directed into the path of the beam from a supply tube, for example. The direction and flow rate of the fluid(s) that is/are introduced can be selected according to a desired exposure rate and/or direction to control the efficiency of the overall treatment, including effects that result from both particle-based treatment and effects that are due to the interaction of dynamically generated species from the introduced fluid with the material. In addition to air, exemplary fluids that can be introduced into the ion beam include oxygen, nitrogen, one or more noble gases, one or more halogens, and hydrogen.

Irradiating Low Bulk Density Biomass Materials and Cooling Irradiated Biomass

During treatment of biomass materials with ionizing radiation, especially at high dose rates, such as at rates greater than 0.15 Mrad per second, e.g., 0.25 Mrad/s, 0.35 Mrad/s, 0.5 Mrad/s, 0.75 Mrad/s or even greater than 1 Mrad/sec, biomass materials can retain significant quantities of heat so that the temperature of the biomass materials becomes elevated. While higher temperatures can, in some embodiments, be advantageous, e.g., when a faster reaction rate is desired, it is advantageous to control the heating of the biomass to retain control over the chemical reactions initiated by the ionizing radiation, such as crosslinking, chain scission and/or grafting, e.g., to maintain process control. Low bulk density materials, such as those having a bulk density of less than about 0.4 g/cm$^3$, e.g., less than about 0.35, 0.25 or less about 0.15 g/cm$^3$, especially when combined with materials that have thin cross-sections, such as fibers having small transverse dimensions, are generally easier to cool. In addition, photons and particles can generally penetrate further into and through materials having a relatively low bulk density, which can allow for the processing of larger volumes of materials at higher rates, and can allow for the use of photons and particles that having lower energies, e.g., 0.25 Mev, 0.5 MeV, 0.75 MeV or 1.0 MeV, which can reduce safety shielding requirements. Many of the biomass materials described herein can be processed in one or more of the systems shown in FIGS. 11B, 11C, 11D and 11E, which are described below. The systems shown allow one or more types of ionizing radiation, such as relativistic electrons or electrons in combination with X-rays, to be applied to low bulk density biomass materials at high dose rates, such as at a rate greater than 1.0, 1.5, 2.5 Mrad/s or even greater than about 5.0 Mrad/s, and then to allow for cooling of the biomass prior to applying radiation for a second, third, fourth, fifth, sixth, seventh, eighth, ninth or even a tenth time.

For example, in one method of changing a molecular and/or a supramolecular structure of a biomass feedstock, the biomass is pretreated at a first temperature with ionizing radiation, such as photons, electrons or ions (e.g., singularly or multiply charged cations or anions), for a sufficient time and/or a sufficient dose to elevate the biomass feedstock to a second temperature higher than the first temperature. The pretreated biomass is then cooled to a third temperature below the second temperature. Finally, if desired, the cooled biomass can be treated one or more times with radiation, e.g., with ionizing radiation. If desired, cooling can be applied to the biomass after and/or during each radiation treatment.

The biomass feedstock can be physically prepared as discussed above, e.g., by reducing one or more dimensions of individual pieces of the biomass feedstock so that the feedstock can be more efficiently processed, e.g., more easily cooled and/or more easily penetrated by an ionizing radiation.

In some implementations, the ionizing radiation is applied at a total dose of less than 25 Mrad or less than 10 Mrad, such as less than 5 Mrad or less than 2.5 Mrad, and at a rate of more than 0.25 Mrad per second, such as more than 0.5, 0.75 or greater than 1.0 Mrad/s, prior to cooling the biomass.

The pretreating of the biomass feedstock with ionizing radiation can be performed as the biomass feedstock is being pneumatically conveyed in a fluid, such as a in a gas, e.g., nitrogen or air. To aid in molecular weight breakdown and/or functionalization of the materials, the gas can be saturated with any swelling agent described herein and/or water vapor. For example, acidic water vapor can be utilized. To aid in molecular weight breakdown, the water can be acidified with an organic acid, such as formic, or acetic acid, or a mineral acid, such as sulfuric or hydrochloric acid.

The pretreating of the biomass feedstock with ionizing radiation can be performed as the biomass feedstock falls under the influence of gravity. This procedure can effectively reduce the bulk density of the biomass feedstock as it is being processed and can aid in the cooling of the biomass feedstock. For example, the biomass can be conveyed from a first belt at a first height above the ground and then can be captured by a second belt at a second level above the ground lower than the first level. For example, in some embodiments, the trailing edge of the first belt and the leading edge of the second belt define a gap. Advantageously, the ionizing radiation, such as a beam of electrons, protons, or other ions, can be applied at the gap to prevent damage to the biomass conveyance system.

Cooling of the biomass can include contacting the biomass with a fluid, such as a gas, at a temperature below the first or second temperature, such as gaseous nitrogen at or about 77 K. Even water, such as water at a temperature below nominal room temperature (e.g., 25 degrees Celsius) can be utilized.

Often advantageously, the biomass feedstock has internal fibers, and prior to irradiation with the ionizing radiation, the biomass feedstock has been sheared to an extent that its internal fibers are substantially exposed. This shearing can provide a low bulk density material having small cross-sectional dimensions, which can aid in the breakdown and/or functionalization of the biomass. For example, in some embodiments, the biomass is or includes discrete fibers and/or particles having a maximum dimension of not more than about 0.5 mm, such as not more than about 0.25 mm, not more than about 0.1 mm or not more than about 0.05 mm.

In some embodiments, the biomass feedstock to which the ionizing radiation is applied has a bulk density of less than about 0.35 g/cm$^3$, such as less than about 0.3, 0.25, 0.20, or less than about 0.15 g/cm$^3$ during the application of the ionizing radiation. In such embodiments, the biomass feedstock can be cooled, and then ionizing radiation can be applied to the cooled biomass. In some advantageous embodiments, the biomass feedstock is or includes discrete fibers and/or particles having a maximum dimension of not more than about 0.5 mm, such as not more than about 0.25 mm, not more than about 0.1 mm, not more than about 0.05 mm, or not more than about 0.025 mm.

FIGS. 11B and 11C show a fibrous material generating, treating, conveying and irradiating device 1170 (shielding not illustrated in the drawings). In operation, paper sheet 1173, e.g., scrap bleached Kraft paper sheet, is supplied from a roll 1172 and delivered to a fiberizing apparatus 1174, such as a rotary shearer. The sheet 1173 is converted into fibrous material 1112 and is delivered to a fiber-loading zone 1180 by conveyer 1178. If desired, the fibers of the fibrous material can be separated, e.g., by screening, into fractions having different L/D ratios. In some embodiments, the fibrous material 1112 of generally a low bulk density and advantageously thin cross-section, is delivered continuously to zone 1180; in other embodiments, the fibrous material is delivered in batches. A blower 1182 in loop 1184 is positioned adjacent to the fiber-loading zone 1180 and is capable of moving a fluid medium, e.g., air, at a velocity and volume sufficient to pneumatically circulate the fibrous material 1112 in a direction indicated by arrow 1188 through loop 1184.

In some embodiments, the velocity of air traveling in the loop is sufficient to uniformly disperse and transport the fibrous material around the entire loop 1184. In some embodiments, the velocity of flow is greater than 2,500 feet/minute, e.g., 5,000 feet/minute, 6,000 feet/minute or more, e.g., 7,500 feet/minute or 8,500 feet/minute.

The entrained fibrous material 1112 traversing the loop passes an application zone 1190, which forms part of loop 1184. Here, any desired additives described herein are applied, such as a liquid, such as water, which may be acidified or made basic. In operation, application zone 1190 applies an additive, such as a liquid solution 1196, to the circulating fibrous material via nozzles 98, 99 and 11100.

When a liquid is applied, the nozzles produce an atomized spray or mist, which impacts the fibers as the fibers pass in proximity to the nozzles. Valve 11102 is operated to control the flow of liquid to the respective nozzles 1198, 1199, and 11100. After a desired quantity of additive is applied, the valve 11102 is closed.

In some embodiments, the application zone 1190 is two to one hundred feet long or more, e.g., 125 feet, 150 feet, 250 feet long or more, e.g., 500 feet long. Longer application zones allow for application of liquid over a longer period of time during passage of fibrous material through application zone 1190. In some embodiments, the nozzles are spaced apart, e.g., by from about three to about four feet, along the length of loop 1184.

As the fibrous material moves in loop 1184 and through the irradiating portion of the loop 11107 that includes a horn 11109 for delivering ionizing radiation, ionizing radiation is applied to the fibrous material (shielding is not shown).

As the irradiated fibrous material moves around loop 1184, it cools by the action of gases, such as air, circulating at high speeds in the loop. The material is bathed in reactive gases, such as ozone and/or oxides of nitrogen that are produced from the action of the ionizing radiation on the circulating gases, such as air. After passing through the irradiating portion 11107, a cooling fluid, such as a liquid (e.g., water) or a gas, such as liquid nitrogen at 77 K, can be injected into loop 1184 to aid in the cooling of the fibrous material. This process can be repeated more than one time if desired, e.g., 2, 3, 4, 5, 6, 7, 8, 9, 10 times or more, e.g., 15 times, to deliver the desired dose to the fibrous material. While, as shown, the long axis of the horn is along the direction of flow, in some implementations, the long axis of the horn is transverse to the direction of the flow. In some implementations, a beam of electrons is utilized as a principal ionizing radiation source and X-rays as a secondary ionizing radiation source. X-rays can be generated by having a metal target, such as a tantalum target 11111, on the inside of loop 1184 such that when electrons strike the target, X-rays are emitted.

After a desired dose is delivered to the fibrous material, the fibrous material can be removed from loop 1184 via a separator 11112, which is selectively connected to loop 1184 by section 11114 and gate valve 11116. When valve 11116 is opened, another valve is also opened to allow air to enter the loop 1184 to compensate for air exiting through separator 11112.

Figure 11E:
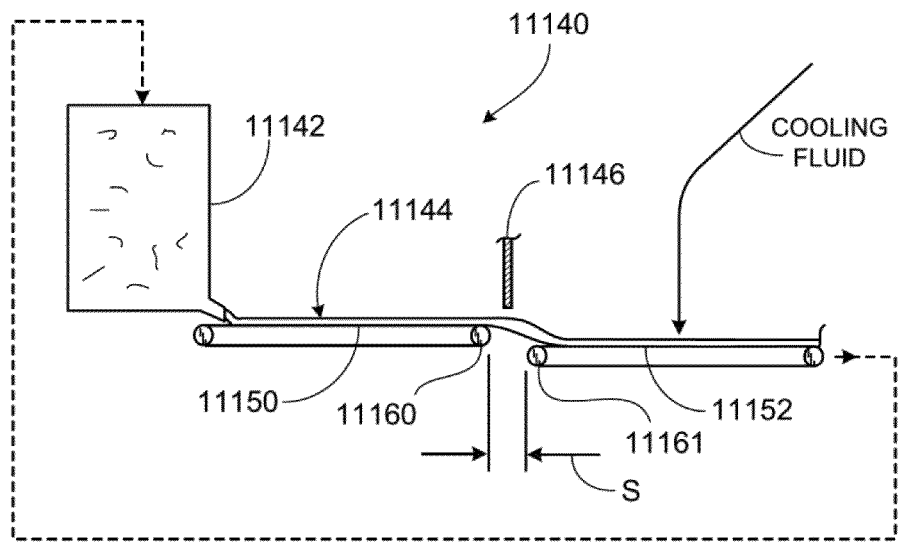
FIG. 11E is a schematic side-view of another system for irradiating a low bulk density material.
Figure 11D:
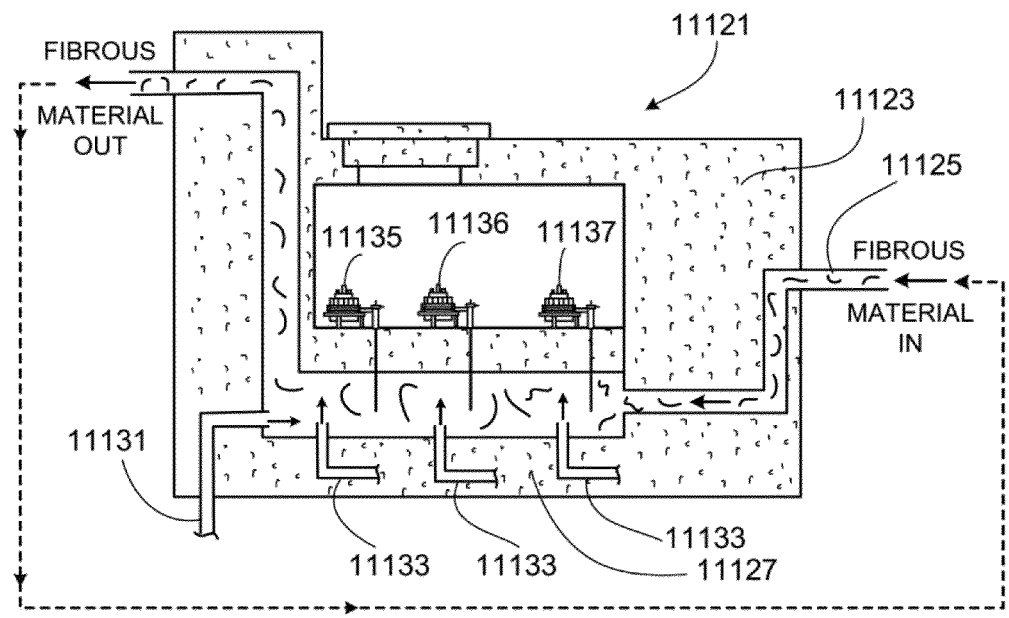
FIG. 11D is a schematic cross-sectional view of a fluidized bed system for irradiating a low bulk density material.

FIG. 11D shows a fluidized bed fibrous irradiating device 11121 with shielding. Fibrous material in a fluid, such as a gas, such as air under pressure, is delivered to a shielded containment vessel 11123 via piping 11125 and into a shielded fluidized bed portion 11127. Counter-current streams 11131 of fluid, such as a gas, and transverse streams 11133 of fluid, such as a gas, that can be the same as or different from the fluid delivered counter-currently, combine to cause turbulence in the bed portion. Ionizing radiation is applied to the fluidized bed portion as the fibrous material is conveyed through the bed portion. For example, as shown, three beams of electrons from three Rhodotron® machines 11135, 11136 and 11137 can be utilized. Advantageously, each beam can penetrate into the fluidized bed a different depth and/or each beam can emit electrons of a different energy, such as 1, 3, and 5 MeV. As the irradiated fibrous material moves through the system, it cools by the action of gases, such as air, circulating at high speeds in the system and it is bathed in reactive gases, such as ozone and/or oxides of nitrogen, that are produced from the action of the ionizing radiation on the circulating gases, such as air. If desired, the process can be repeated a desired number of times until the fibrous material has received a desired dose. While the fluidized bed has been illustrated such that its long axis is horizontal with the ground, in other implementations, the long axis of the bed is perpendicular to the ground so that the fibrous material falls under the influence of gravity.

FIG. 11E shows another fibrous material conveying and irradiating device 11140 without shielding. Fibrous material 11144 is delivered from a bin 11142 to a first conveyer 11150 at a first level above the ground and then the material is transferred to a second conveyer 11152 at a lower height than the first conveyer. The trailing edge 11160 of the first conveyer and the leading edge 11161 of the second conveyer 11152 define a gap with a spacing S. For example, the spacing S can be between 4 inches and about 24 inches. Material 11144 has enough momentum to free fall under gravity and then to be captured by the second conveyer 11152 without falling into the gap. During the free fall, ionizing radiation is applied to the material. This arrangement can be advantageous in that the ionizing radiation is less likely to damage the conveying system because the conveying system is not directly contacted by the radiation.

After the material passes through the irradiating portion, a cooling fluid, such as a liquid (e.g., water) or a gas, such as liquid nitrogen at 77 K, can be applied to the material to aid in the cooling of the fibrous material. This process can be repeated more than one time if desired, e.g., 2, 3, 4, 5, 6, 7, 8, 9, 10 times or more, e.g., 15 times, to deliver the desired dose to the fibrous material. While, as shown, the long axis of the horn is transverse to the direction of the material flow, other beam arrangements are possible. In some implementations, a beam of electrons is utilized as a principal ionizing radiation source and X-rays as a secondary ionizing radiation source. X-rays can be generated by having a metal target, such as a tantalum target, in the gap on the opposite side of the material, such that as the electrons that pass through the material they strike the target, generating X-rays.

Sonication and Other Biomass Disruption Processes

One or more sonication processing sequences can be used to process raw feedstock from a wide variety of different sources to extract useful substances from the feedstock, and to provide partially degraded organic material which functions as input to further processing steps and/or sequences. Sonication can reduce the molecular weight and/or crystallinity of feedstock, such as one or more of any of the biomass materials described herein, e.g., one or more carbohydrate sources, such as cellulosic or lignocellulosic materials, or starchy materials.

Referring again to FIG. 8, in one method, a first material 2 that includes cellulose having a first number average molecular weight ($^{T}M_{n1}$) is dispersed in a medium, such as water, and sonicated and/or otherwise cavitated, to provide a second material 3 that includes cellulose having a second number average molecular weight ($^{T}M_{n2}$) lower than the first number average molecular weight. The second material (or the first and second material in certain embodiments) can be combined with a microorganism (e.g., a bacterium or a yeast) that can utilize the second and/or first material to produce a fuel 5 that is or includes hydrogen, an alcohol, an organic acid, a hydrocarbon or mixtures of any of these.

Since the second material has cellulose having a reduced molecular weight relative to the first material, and in some instances, a reduced crystallinity as well, the second material is generally more dispersible, swellable, and/or soluble in a solution containing the microorganism, e.g., at a concentration of greater than $10^6$ microorganisms/mL. These properties make the second material 3 more susceptible to chemical, enzymatic, and/or microbial attack relative to the first material 2, which can greatly improve the production rate and/or production level of a desired product, e.g., ethanol. Sonication can also sterilize the materials, but should not be used while the microorganisms are supposed to be alive.

In some embodiments, the second number average molecular weight ($^{T}M_{n2}$) is lower than the first number average molecular weight ($^{T}M_{n1}$) by more than about 10 percent, e.g., 15, 20, 25, 30, 35, 40, 50 percent, 60 percent, or even more than about 75 percent.

In some instances, the second material has cellulose that has as crystallinity ($^{T}C_{2}$) that is lower than the crystallinity ($^{T}C_{1}$) of the cellulose of the first material. For example, ($^{T}C_{2}$) can be lower than ($^{T}C_{1}$) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($^{T}O_{2}$) that is higher than the level of oxidation ($^{T}O_{1}$) of the first material. A higher level of oxidation of the material can aid in its dispersibility, swellability and/or solubility, further enhancing the materials susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Without wishing to be bound by any particular theory, it is believed that sonication breaks bonds in the cellulose by creating bubbles in the medium containing the cellulose, which grow and then violently collapse. During the collapse of the bubble, which can take place in less than a nanosecond, the implosive force raises the local temperature within the bubble to about 5100 K (even higher in some instance; see, e.g., Suslick et al., Nature 434, 52-55) and generates pressures of from a few hundred atmospheres to over 1000 atmospheres or more. It is these high temperatures and pressures that break the bonds. In addition, without wishing to be bound by any particular theory, it is believed that reduced crystallinity arises, at least in part, from the extremely high cooling rates during collapse of the bubbles, which can be greater than about $10^{11}$ K/second. The high cooling rates generally do not allow the cellulose to organize and crystallize, resulting in materials that have reduced crystallinity. Ultrasonic systems and sonochemistry are discussed in, e.g., Olli et al., U.S. Pat. No. 5,766,764; Roberts, U.S. Pat. No. 5,828,156; Mason, Chemistry with Ultrasound, Elsevier, Oxford, (1990); Suslick (editor), Ultrasound: its Chemical, Physical and Biological Effects, VCH, Weinheim, (1988); Price, "Current Trends in Sonochemistry" Royal Society of Chemistry, Cambridge, (1992); Suslick et al., Ann. Rev. Mater. Sci. 29, 295, (1999); Suslick et al., Nature 353, 414 (1991); Hiller et al., Phys. Rev. Lett. 69, 1182 (1992); Barber et al., Nature, 352, 414 (1991); Suslick et al., J. Am. Chem. Soc., 108, 5641 (1986); Tang et al., Chem. Comm., 2119 (2000); Wang et al., Advanced Mater., 12, 1137 (2000); Landau et al., J. of Catalysis, 201, 22 (2001); Perkas et al., Chem. Comm., 988 (2001); Nikitenko et al., Angew. Chem. Inter. Ed. (December 2001); Shafi et al., J. Phys. Chem B 103, 3358 (1999); Avivi et al., J. Amer. Chem. Soc. 121, 4196 (1999); and Avivi et al., J. Amer. Chem. Soc. 122, 4331 (2000).

Sonication Systems

Figure 12:
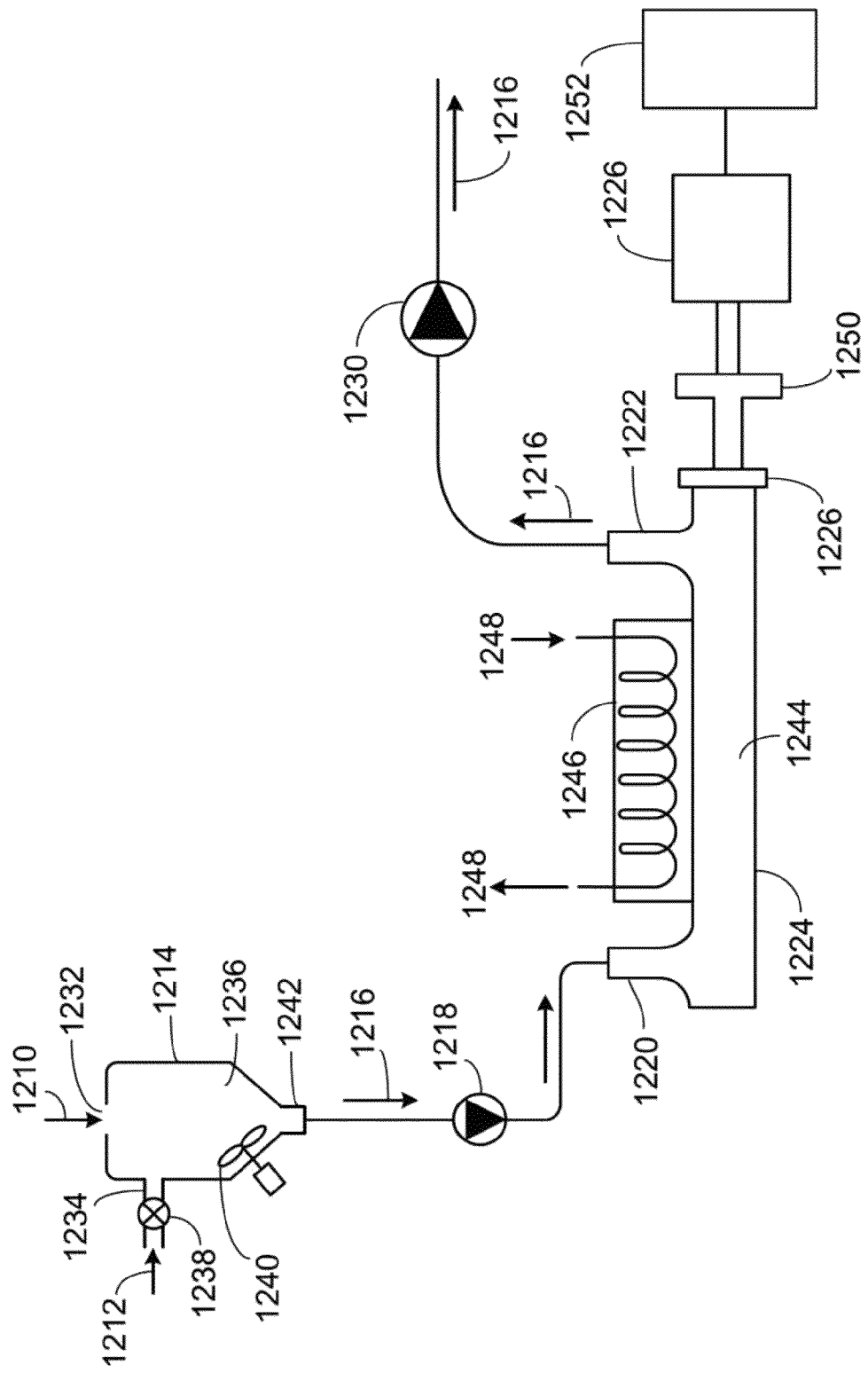
FIG. 12 is a schematic view of a system for sonicating a process stream of cellulosic material in a liquid medium.

FIG. 12 shows a general system in which a cellulosic material stream 1210 is mixed with a water stream 1212 in a reservoir 1214 to form a process stream 1216. A first pump 1218 draws process stream 1216 from reservoir 1214 and toward a flow cell 1224. Ultrasonic transducer 1226 transmits ultrasonic energy into process stream 1216 as the process stream flows through flow cell 1224. A second pump 1230 draws process stream 1216 from flow cell 1224 and toward subsequent processing.

Reservoir 1214 includes a first intake 1232 and a second intake 1234 in fluid communication with a volume 1236. A conveyor (not shown) delivers cellulosic material stream 1210 to reservoir 1214 through first intake 1232. Water stream 1212 enters reservoir 1214 through second intake 1234. In some embodiments, water stream 1212 enters volume 1236 along a tangent establishing a swirling flow within volume 1236. In certain embodiments, cellulosic material stream 1210 and water stream 1212 can be introduced into volume 1236 along opposing axes to enhance mixing within the volume.

Valve 1238 controls the flow of water stream 1212 through second intake 1232 to produce a desired ratio of cellulosic material to water (e.g., approximately 10% cellulosic material, weight by volume). For example, 2000 tons/day of cellulosic material can be combined with 1 million to 1.5 million gallons/day, e.g., 1.25 million gallons/day, of water.

Mixing of cellulosic material and water in reservoir 1214 is controlled by the size of volume 1236 and the flow rates of cellulosic material and water into the volume. In some embodiments, volume 1236 is sized to create a minimum mixing residence time for the cellulosic material and water. For example, when 2000 tons/day of cellulosic material and 1.25 million gallons/day of water are flowing through reservoir 1214, volume 1236 can be about 32,000 gallons to produce a minimum mixing residence time of about 15 minutes.

Reservoir 1214 includes a mixer 1240 in fluid communication with volume 1236. Mixer 1240 agitates the contents of volume 1236 to disperse cellulosic material throughout the water in the volume. For example, mixer 1240 can be a rotating vane disposed in reservoir 1214. In some embodiments, mixer 1240 disperses the cellulosic material substantially uniformly throughout the water.

Reservoir 1214 further includes an exit 1242 in fluid communication with volume 1236 and process stream 1216. The mixture of cellulosic material and water in volume 1236 flows out of reservoir 1214 via exit 1242. Exit 1242 is arranged near the bottom of reservoir 1214 to allow gravity to pull the mixture of cellulosic material and water out of reservoir 1214 and into process stream 1216.

First pump 1218 (e.g., any of several recessed impeller vortex pumps made by Essco Pumps & Controls, Los Angeles, Calif.) moves the contents of process stream 1216 toward flow cell 1224. In some embodiments, first pump 1218 agitates the contents of process stream 1216 such that the mixture of cellulosic material and water is substantially uniform at inlet 1220 of flow cell 1224. For example, first pump 1218 agitates process stream 1216 to create a turbulent flow that persists along the process stream between the first pump and inlet 1220 of flow cell 1224.

Flow cell 1224 includes a reactor volume 1244 in fluid communication with inlet 1220 and outlet 1222. In some embodiments, reactor volume 1244 is a stainless steel tube capable of withstanding elevated pressures (e.g., 10 bars). In addition or in the alternative, reactor volume 1244 includes a rectangular cross section.

Flow cell 1224 further includes a heat exchanger 1246 in thermal communication with at least a portion of reactor volume 1244. Cooling fluid 1248 (e.g., water) flows into heat exchanger 1246 and absorbs heat generated when process stream 1216 is sonicated in reactor volume 1244. In some embodiments, the flow rate and/or the temperature of cooling fluid 1248 into heat exchanger 1246 is controlled to maintain an approximately constant temperature in reactor volume 1244. In some embodiments, the temperature of reactor volume 1244 is maintained at 20 to 50° C., e.g., 25, 30, 35, 40, or 45° C. Additionally or alternatively, heat transferred to cooling fluid 1248 from reactor volume 1244 can be used in other parts of the overall process.

An adapter section 1226 creates fluid communication between reactor volume 1244 and a booster 1250 coupled (e.g., mechanically coupled using a flange) to ultrasonic transducer 1226. For example, adapter section 1226 can include a flange and O-ring assembly arranged to create a leak tight connection between reactor volume 1244 and booster 1250. In some embodiments, ultrasonic transducer 1226 is a high-powered ultrasonic transducer made by Hielscher Ultrasonics of Teltow, Germany.

In operation, a generator 1252 delivers electricity to ultrasonic transducer 1252. Ultrasonic transducer 1226 includes a piezoelectric element that converts the electrical energy into sound in the ultrasonic range. In some embodiments, the materials are sonicated using sound having a frequency of from about 16 kHz to about 110 kHz, e.g., from about 18 kHz to about 75 kHz or from about 20 kHz to about 40 kHz. (e.g., sound having a frequency of 20 kHz to 40 kHz). In some implementations, sonication is performed, for example, at a frequency of between about 15 kHz and about 25 kHz, such as between about 18 kHz and 22 kHz. In specific embodiments, sonicating can be performed utilizing a 1 KW or larger horn, e.g., a 2, 3, 4, 5, or even a 10 KW horn.

The ultrasonic energy is then delivered to the working medium through booster 1248. The ultrasonic energy traveling through booster 1248 in reactor volume 1244 creates a series of compressions and rarefactions in process stream 1216 with an intensity sufficient to create cavitation in process stream 1216. Cavitation disaggregates the cellulosic material dispersed in process stream 1216. Cavitation also produces free radicals in the water of process stream 1216. These free radicals act to further break down the cellulosic material in process stream 1216.

In general, 5 to 4000 MJ/m$^3$, e.g., 10, 25, 50, 100, 250, 500, 750, 1000, 2000, or 3000 MJ/m$^3$, of ultrasonic energy is applied to process stream 16 flowing at a rate of about 0.2 m$^3$/s (about 3200 gallons/min). After exposure to ultrasonic energy in reactor volume 1244, process stream 1216 exits flow cell 1224 through outlet 1222. Second pump 1230 moves process stream 1216 to subsequent processing (e.g., any of several recessed impeller vortex pumps made by Essco Pumps & Controls, Los Angeles, Calif.).

While certain embodiments have been described, other embodiments are possible.

As an example, while process stream 1216 has been described as a single flow path, other arrangements are possible. In some embodiments, for example, process stream 1216 includes multiple parallel flow paths (e.g., flowing at a rate of 10 gallon/min). In addition or in the alternative, the multiple parallel flow paths of process stream 1216 flow into separate flow cells and are sonicated in parallel (e.g., using a plurality of 16 kW ultrasonic transducers).

As another example, while a single ultrasonic transducer 1226 has been described as being coupled to flow cell 1224, other arrangements are possible. In some embodiments, a plurality of ultrasonic transducers 1226 are arranged in flow cell 1224 (e.g., ten ultrasonic transducers can be arranged in a flow cell 1224). In some embodiments, the sound waves generated by each of the plurality of ultrasonic transducers 1226 are timed (e.g., synchronized out of phase with one another) to enhance the cavitation acting upon process stream 1216.

As another example, while a single flow cell 1224 has been described, other arrangements are possible. In some embodiments, second pump 1230 moves process stream to a second flow cell where a second booster and ultrasonic transducer further sonicate process stream 1216.

As still another example, while reactor volume 1244 has been described as a closed volume, reactor volume 1244 is open to ambient conditions in certain embodiments. In such embodiments, sonication pretreatment can be performed substantially simultaneously with other pretreatment techniques. For example, ultrasonic energy can be applied to process stream 1216 in reactor volume 1244 while electron beams are simultaneously introduced into process stream 1216.

As another example, while a flow-through process has been described, other arrangements are possible. In some embodiments, sonication can be performed in a batch process. For example, a volume can be filled with a 10% (weight by volume) mixture of cellulosic material in water and exposed to sound with intensity from about 50 W/cm$^2$ to about 600 W/cm$^2$, e.g., from about 75 W/cm$^2$ to about 300 W/cm$^2$ or from about 95 W/cm$^2$ to about 200 W/cm$^2$. Additionally or alternatively, the mixture in the volume can be sonicated from about 1 hour to about 24 hours, e.g., from about 1.5 hours to about 12 hours, or from about 2 hours to about 10 hours. In certain embodiments, the material is sonicated for a pre-determined time, and then allowed to stand for a second pre-determined time before sonicating again.

Figure 13:
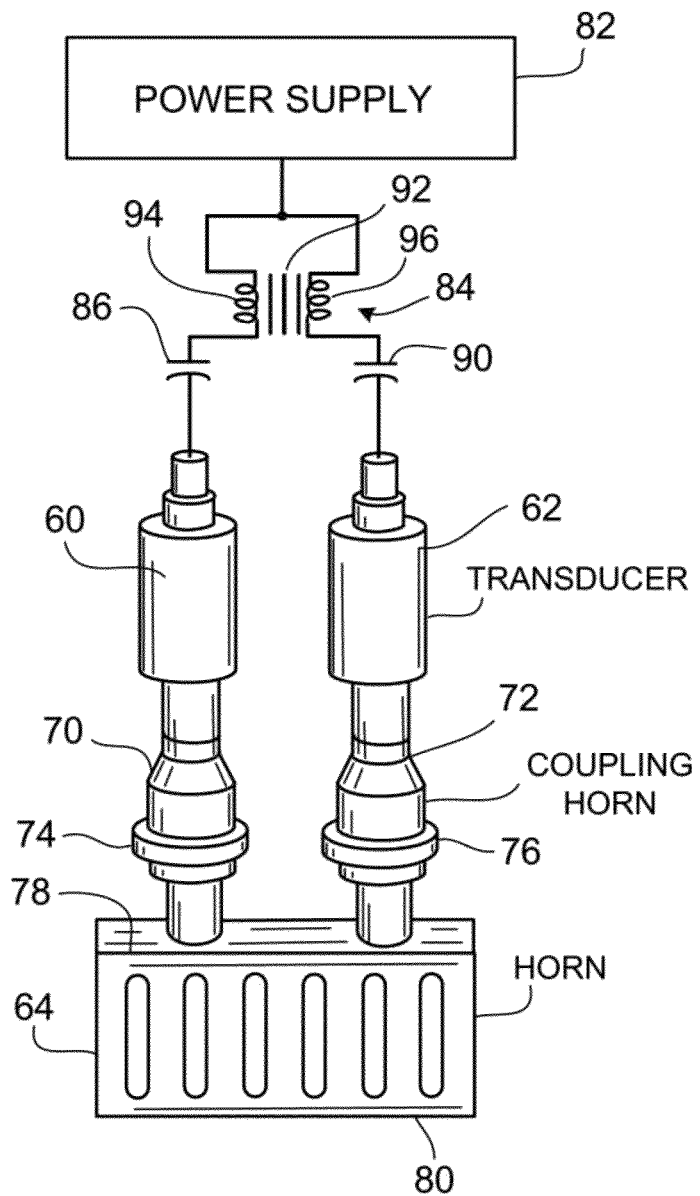
FIG. 13 is a schematic view of a sonicator having two transducers coupled to a single horn.

Referring now to FIG. 13, in some embodiments, two electroacoustic transducers are mechanically coupled to a single horn. As shown, a pair of piezoelectric transducers 60 and 62 is coupled to a slotted bar horn 64 by respective intermediate coupling horns 70 and 72, the latter also being known as booster horns. The mechanical vibrations provided by the transducers, responsive to high frequency electrical energy applied thereto, are transmitted to the respective coupling horns, which may be constructed to provide a mechanical gain, such as a ratio of 1 to 1.2. The horns are provided with a respective mounting flange 74 and 76 for supporting the transducer and horn assembly in a stationary housing.

The vibrations transmitted from the transducers through the coupling or booster horns are coupled to the input surface 78 of the horn and are transmitted through the horn to the oppositely disposed output surface 80, which, during operation, is in forced engagement with a workpiece (not shown) to which the vibrations are applied.

The high frequency electrical energy provided by the power supply 82 is fed to each of the transducers, electrically connected in parallel, via a balancing transformer 84 and a respective series connected capacitor 86 and 90, one capacitor connected in series with the electrical connection to each of the transducers. The balancing transformer is known also as "balun" standing for "balancing unit." The balancing transformer includes a magnetic core 92 and a pair of identical windings 94 and 96, also termed the primary winding and secondary winding, respectively.

In some embodiments, the transducers include commercially available piezoelectric transducers, such as Branson Ultrasonics Corporation models 105 or 502, each designed for operation at 20 kHz and a maximum power rating of 3 kW. The energizing voltage for providing maximum motional excursion at the output surface of the transducer is 930 volt rms. The current flow through a transducer may vary between zero and 3.5 ampere depending on the load impedance. At 930 volt rms the output motion is approximately 20 microns. The maximum difference in terminal voltage for the same motional amplitude, therefore, can be 186 volt. Such a voltage difference can give rise to large circulating currents flowing between the transducers. The balancing unit 430 assures a balanced condition by providing equal current flow through the transducers, hence eliminating the possibility of circulating currents. The wire size of the windings must be selected for the full load current noted above and the maximum voltage appearing across a winding input is 93 volt.

While ultrasonic transducer 1226 has been described as including one or more piezoelectric active elements to create ultrasonic energy, other arrangements are possible. In some embodiments, ultrasonic transducer 1226 includes active elements made of other types of magnetostrictive materials (e.g., ferrous metals). Design and operation of such a high-powered ultrasonic transducer is discussed in Hansen et al., U.S. Pat. No. 6,624,539. In some embodiments, ultrasonic energy is transferred to process stream 16 through an electrohydraulic system.

While ultrasonic transducer 1226 has been described as using the electromagnetic response of magnetorestrictive materials to produce ultrasonic energy, other arrangements are possible. In some embodiments, acoustic energy in the form of an intense shock wave can be applied directly to process stream 16 using an underwater spark. In some embodiments, ultrasonic energy is transferred to process stream 16 through a thermohydraulic system. For example, acoustic waves of high energy density can be produced by applying power across an enclosed volume of electrolyte, thereby heating the enclosed volume and producing a pressure rise that is subsequently transmitted through a sound propagation medium (e.g., process stream 1216). Design and operation of such a thermohydraulic transducer is discussed in Hartmann et al., U.S. Pat. No. 6,383,152.

Some embodiments use a high frequency, rotor-stator device. This type of device produces high-shear, microcavitation forces, which can disintegrate biomass in contact with such forces. Two commercially available high-frequency, rotor-stator dispersion devices are the SUPRATON™ devices manufactured by Krupp Industrietechnik GmbH and marketed by Dorr-Oliver Deutschland GmbH of Connecticut, and the DISPAX™ devices manufactured and marketed by Ika-Works, Inc. of Cincinnati, Ohio. Operation of such a microcavitation device is discussed in Stuart, U.S. Pat. No. 5,370,999.

In another biomass disruption technique, microwave or radiowave energy is applied to a treated or untreated biomass material, such as a lignocellulosic material, in a manner that water within the biomass material is vaporized, but overall the biomass material undergoes little bulk heating. For example, a frequency of from about 10 MHz to about 300,000 MHz can be applied to the biomass material. In some instances the microwave or radiowave energy is applied in short pulses, e.g., having a duration of less than 0.1 seconds, e.g., less than 0.05 seconds, less than 0.03 seconds, less than 0.01 seconds or even less, e.g., 0.005 seconds. Without wishing to be bound by any particular theory, it is believed when the microwave or radiowave energy is applied in this manner, water is vaporized within the biomass material with explosive force, which disrupts the lignin and "peels" it away from the cellulose. At the same time, since application of such energy does not heat the bulk material, the lignin does not tend to re-apply onto the cellulose, which could block access to the cellulose, e.g., by an enzyme or microbe. Many of the properties of lignin are described Carter Fox in a thesis entitled "Chemical and Thermal Characterization of Three Industrial Lignin and Their Corresponding Esters (May 2006, University of Idaho).

In another biomass disruption technique, treated (e.g., using any treatment method described herein) or untreated biomass material is subjected to a hot, compressed fluid, such as water. In such a method, the biomass is placed in a pressure vessel containing a fluid, such as water, at an elevated temperature, e.g., above 50, 60, 70, 80, 90, 100, 110, 120, 130, 140, 150, 160, 170, or above 180° C. The pressure vessel is placed under gas pressure, such as under argon, nitrogen or air, and then stirred, e.g., with a two blade turbine propeller for a period of time, e.g., 10 minutes, 20 minutes, 30 minutes, 45 minutes, 60 minutes or 90 minutes. In some embodiments, the pressure is between about 500 psig and 2000 psig, e.g., between about 650 psig and about 1500 psig or between about 700 psig and about 1200 psig. In some embodiments, the temperature is at or 5 or 10° C. above a glass transition temperature for the lignin. Without wishing to be bound by any particular theory, it is believed that when the temperature is above the glass transition temperature of the lignin, the conditions in the pressure vessel cause the lignin to "peel" away from the cellulose, making the cellulose more exposed for breakdown, e.g., by an enzyme.

In another biomass disruption technique, treated, e.g., irradiated, or untreated biomass material is delivered to a nip defined between two counter rotating pressure rolls, which can be optionally heated. Pressure in the nip can be adjusted by the amount of biomass material fed into the nip and the spacing between the pressure rolls. In some embodiments, the pressure in the nip can be greater than 1,000 psi per linear inch, e.g., greater than 2,500 psi, greater than 5,000 psi, greater than 7,500 psi, greater than 10,000 psi, or even greater than 15,000 psi per linear inch. In some embodiments, the pressure rolls are operated at an elevated temperature, e.g., above 50, 60, 70, 80, 90, 100, 110, 120, 130, 140, 150, 160, 170, or above 180° C. In some embodiments, the rolls are operated at a temperature above a glass transition temperature of the lignin. Without wishing to be bound by any particular theory, it is believed that the pressure and heat in the nip can disrupt any lignin of the biomass material, making the cellulose more accessible and available to an enzyme.

Pyrolysis

One or more pyrolysis processing sequences can be used to process raw feedstock from a wide variety of different sources to extract useful substances from the feedstock, and to provide partially degraded organic material which functions as input to further processing steps and/or sequences.

Referring again to the general schematic in FIG. 8, a first material 2 that includes cellulose having a first number average molecular weight ($^TM_{n1}$) is pyrolyzed, e.g., by heating the first material in a tube furnace, to provide a second material 3 that includes cellulose having a second number average molecular weight ($^TM_{n2}$) lower than the first number average molecular weight. The second material (or the first and second material in certain embodiments) is/are combined with a microorganism (e.g., a bacterium or a yeast) that can utilize the second and/or first material to produce a fuel 5 that is or includes hydrogen, an alcohol (e.g., ethanol or butanol, such as n-, sec or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing the microorganism, e.g., at a concentration of greater than $10^6$ microorganisms/mL. These properties make the second material 3 more susceptible to chemical, enzymatic and/or microbial attack relative to the first material 2, which can greatly improve the production rate and/or production level of a desired product, e.g., ethanol. Pyrolysis can also sterilize the first and second materials.

In some embodiments, the second number average molecular weight ($^TM_{n2}$) is lower than the first number average molecular weight ($^TM_{n1}$) by more than about 10 percent, e.g., 15, 20, 25, 30, 35, 40, 50 percent, 60 percent, or even more than about 75 percent.

In some instances, the second material has cellulose that has as crystallinity ($^TC_2$) that is lower than the crystallinity ($^TC_1$) of the cellulose of the first material. For example, ($^TC_2$) can be lower than ($^TC_1$) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($^TO_2$) that is higher than the level of oxidation ($^TO_1$) of the first material. A higher level of oxidation of the material can aid in its dispersibility, swellability and/or solubility, further enhancing the materials susceptibility to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, which can increase its hydrophilicity.

In some embodiments, the pyrolysis of the materials is continuous. In other embodiments, the material is pyrolyzed for a pre-determined time, and then allowed to cool for a second pre-determined time before pyrolyzing again.

Pyrolysis Systems

Figure 14:
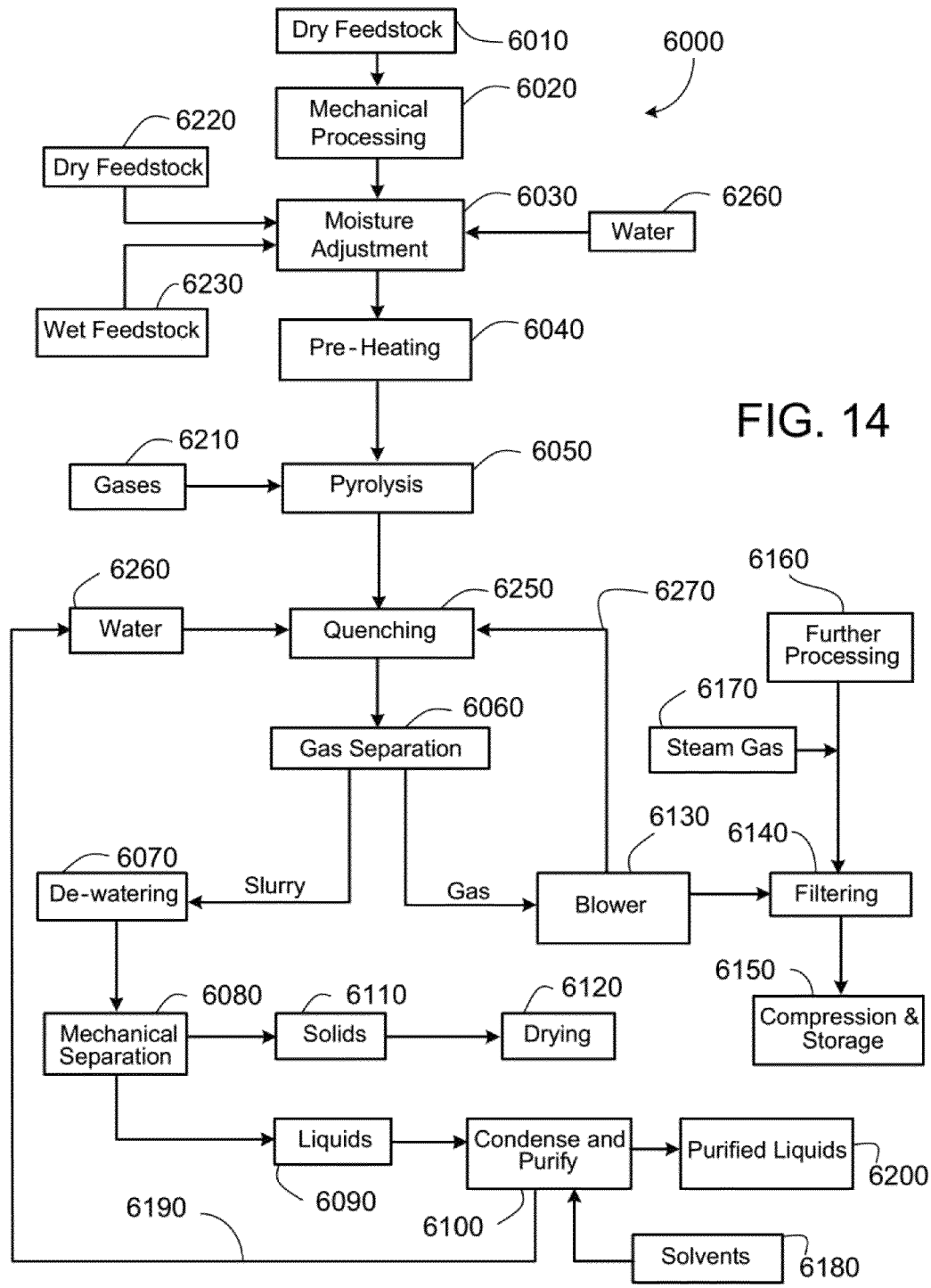
FIG. 14 is a block diagram illustrating a pyrolytic feedstock pretreatment system.

FIG. 14 shows a process flow diagram 6000 that includes various steps in a pyrolytic feedstock pretreatment system. In first step 6010, a supply of dry feedstock is received from a feed source.

As described above, the dry feedstock from the feed source may be pre-processed prior to delivery to the pyrolysis chamber. For example, if the feedstock is derived from plant sources, certain portions of the plant material may be removed prior to collection of the plant material and/or before the plant material is delivered by the feedstock transport device. Alternatively, or in addition, the biomass feedstock can be subjected to mechanical processing 6020 (e.g., to reduce the average length of fibers in the feedstock) prior to delivery to the pyrolysis chamber.

Following mechanical processing, the feedstock undergoes a moisture adjustment step 6030. The nature of the moisture adjustment step depends upon the moisture content of the mechanically processed feedstock. Typically, pyrolysis of feedstock occurs most efficiently when the moisture content of the feedstock is between about 10% and about 30% (e.g., between 15% and 25%) by weight of the feedstock. If the moisture content of the feedstock is larger than about 40% by weight, the extra thermal load presented by the water content of the feedstock increases the energy consumption of subsequent pyrolysis steps.

In some embodiments, if the feedstock has a moisture content which is larger than about 30% by weight, drier feedstock material 6220, which has a low moisture content, can be blended in, creating a feedstock mixture in step 6030 with an average moisture content that is within the limits discussed above. In certain embodiments, feedstock with a high moisture content can simply be dried by dispersing the feedstock material on a moving conveyor that cycles the feedstock through an in-line heating unit. The heating unit evaporates a portion of the water present in the feedstock.

In some embodiments, if the feedstock from step 6020 has a moisture content which is too low (e.g., lower than about 10% by weight), the mechanically processed feedstock can be combined with wetter feedstock material 6230 with a higher moisture content, such as sewage sludge. Alternatively, or in addition, water 6240 can be added to the dry feedstock from step 6020 to increase its moisture content.

In step 6040, the feedstock—now with its moisture content adjusted to fall within suitable limits—can be preheated in an optional preheating step 6040. Preheating step 6040 can be used to increase the temperature of the feedstock to between 75° C. and 150° C. in preparation for subsequent pyrolysis of the feedstock. Depending upon the nature of the feedstock and the particular design of the pyrolysis chamber, preheating the feedstock can ensure that heat distribution within the feedstock remains more uniform during pyrolysis, and can reduce the thermal load on the pyrolysis chamber.

The feedstock is then transported to a pyrolysis chamber to undergo pyrolysis in step 6050. In some embodiments, transport of the feedstock is assisted by adding one or more pressurized gases 6210 to the feedstock stream. The gases create a pressure gradient in a feedstock transport conduit, propelling the feedstock into the pyrolysis chamber (and even through the pyrolysis chamber). In certain embodiments, transport of the feedstock occurs mechanically; that is, a transport system that includes a conveyor such as an auger transports the feedstock to the pyrolysis chamber.

Other gases 6210 can also be added to the feedstock prior to the pyrolysis chamber. In some embodiments, for example, one or more catalyst gases can be added to the feedstock to assist decomposition of the feedstock during pyrolysis. In certain embodiments, one or more scavenging agents can be added to the feedstock to trap volatile materials released during pyrolysis. For example, various sulfur-based compounds such as sulfides can be liberated during pyrolysis, and an agent such as hydrogen gas can be added to the feedstock to cause desulfurization of the pyrolysis products. Hydrogen combines with sulfides to form hydrogen sulfide gas, which can be removed from the pyrolyzed feedstock.

Pyrolysis of the feedstock within the chamber can include heating the feedstock to relatively high temperatures to cause partial decomposition of the feedstock. Typically, the feedstock is heated to a temperature in a range from 150° C. to 1100° C. The temperature to which the feedstock is heated depends upon a number of factors, including the composition of the feedstock, the feedstock average particle size, the moisture content, and the desired pyrolysis products. For many types of biomass feedstock, for example, pyrolysis temperatures between 300° C. and 550° C. are used.

The residence time of the feedstock within the pyrolysis chamber generally depends upon a number of factors, including the pyrolysis temperature, the composition of the feedstock, the feedstock average particle size, the moisture content, and the desired pyrolysis products. In some embodiments, feedstock materials are pyrolyzed at a temperature just above the decomposition temperature for the material in an inert atmosphere, e.g., from about 2° C. above to about 10° C. above the decomposition temperature or from about 3° C. above to about 7° C. above the decomposition temperature. In such embodiments, the material is generally kept at this temperature for greater than 0.5 hours, e.g., greater than 1.0 hour or greater than about 2.0 hours. In other embodiments, the materials are pyrolyzed at a temperature well above the decomposition temperature for the material in an inert atmosphere, e.g., from about 75° C. above to about 175° C. above the decomposition temperature or from about 85° C. above to about 150° C. above the decomposition temperature. In such embodiments, the material is generally kept at this temperature for less than 0.5 hour, e.g., less 20 minutes, less than 10 minutes, less than 5 minutes or less than 2 minutes. In still other embodiments, the materials are pyrolyzed at an extreme temperature, e.g., from about 200° C. above to about 500° C. above the decomposition temperature of the material in an inert environment or from about 250° C. above to about 400° C. above the decomposition temperature. In such embodiments, the material is generally kept at this temperature for less than 1 minute, e.g., less than 30 seconds, 15 seconds, 10 seconds, 5 seconds, 1 second or less than 500 ms. Such embodiments are typically referred to as flash pyrolysis.

In some embodiments, the feedstock is heated relatively rapidly to the selected pyrolysis temperature within the chamber. For example, the chamber can be designed to heat the feedstock at a rate of between 500° C./s and 11,000° C./s, for example, from 500° C./s to 1000° C./s.

A turbulent flow of feedstock material within the pyrolysis chamber is usually advantageous, as it ensures relatively efficient heat transfer to the feedstock material from the heating sub-system. Turbulent flow can be achieved, for example, by blowing the feedstock material through the chamber using one or more injected carrier gases 6210. In general, the carrier gases are relatively inert towards the feedstock material, even at the high temperatures in the pyrolysis chamber. Exemplary carrier gases include, for example, nitrogen, argon, methane, carbon monoxide, and carbon dioxide. Alternatively, or in addition, mechanical transport systems such as augers can transport and circulate the feedstock within the pyrolysis chamber to create a turbulent feedstock flow.

In some embodiments, pyrolysis of the feedstock occurs substantially in the absence of oxygen and other reactive gases. Oxygen can be removed from the pyrolysis chamber by periodic purging of the chamber with high pressure nitrogen (e.g., at nitrogen pressures of 2 bar or more). Following purging of the chamber, a gas mixture present in the pyrolysis chamber (e.g., during pyrolysis of the feedstock) can include less than 4 mole % oxygen (e.g., less than 1 mole % oxygen, and even less than 0.5 mole % oxygen). The absence of oxygen ensures that ignition of the feedstock does not occur at the elevated pyrolysis temperatures.

In certain embodiments, relatively small amounts of oxygen can be introduced into the feedstock and are present during pyrolysis. This technique is referred to as oxidative pyrolysis. Typically, oxidative pyrolysis occurs in multiple heating stages. For example, in a first heating stage, the feedstock is heated in the presence of oxygen to cause partial oxidation of the feedstock. This stage consumes the available oxygen in the pyrolysis chamber. Then, in subsequent heating stages, the feedstock temperature is further elevated. With all of the oxygen in the chamber consumed, however, feedstock combustion does not occur, and combustion-free pyrolytic decomposition of the feedstock (e.g., to generate hydrocarbon products) occurs. In general, the process of heating feedstock in the pyrolysis chamber to initiate decomposition is endothermic. However, in oxidative pyrolysis, formation of carbon dioxide by oxidation of the feedstock is an exothermic process. The heat released from carbon dioxide formation can assist further pyrolysis heating stages, thereby lessening the thermal load presented by the feedstock.

In some embodiments, pyrolysis occurs in an inert environment, such as while feedstock materials are bathed in argon or nitrogen gas. In certain embodiments, pyrolysis can occur in an oxidizing environment, such as in air or argon enriched in air. In some embodiments, pyrolysis can take place in a reducing environment, such as while feedstock materials are bathed in hydrogen gas. To aid pyrolysis, various chemical agents, such as oxidants, reductants, acids or bases can be added to the material prior to or during pyrolysis. For example, sulfuric acid can be added, or a peroxide (e.g., benzoyl peroxide) can be added.

As discussed above, a variety of different processing conditions can be used, depending upon factors such as the feedstock composition and the desired pyrolysis products. For example, for cellulose-containing feedstock material, relatively mild pyrolysis conditions can be employed, including flash pyrolysis temperatures between 375° C. and 450° C., and residence times of less than 1 second. As another example, for organic solid waste material such as sewage sludge, flash pyrolysis temperatures between 500° C. and 650° C. are typically used, with residence times of between 0.5 and 3 seconds. In general, many of the pyrolysis process parameters, including residence time, pyrolysis temperature, feedstock turbulence, moisture content, feedstock composition, pyrolysis product composition, and additive gas composition can be regulated automatically by a system of regulators and an automated control system.

Following pyrolysis step 6050, the pyrolysis products undergo a quenching step 6250 to reduce the temperature of the products prior to further processing. Typically, quenching step 6250 includes spraying the pyrolysis products with streams of cooling water 6260. The cooling water also forms a slurry that includes solid, undissolved product material and various dissolved products. Also present in the product stream is a mixture that includes various gases, including product gases, carrier gases, and other types of process gases.

The product stream is transported via in-line piping to a gas separator that performs a gas separation step 6060, in which product gases and other gases are separated from the slurry formed by quenching the pyrolysis products. The separated gas mixture is optionally directed to a blower 6130, which increases the gas pressure by blowing air into the mixture. The gas mixture can be subjected to a filtration step 6140, in which the gas mixture passes through one or more filters (e.g., activated charcoal filters) to remove particulates and other impurities. In a subsequent step 6150, the filtered gas can be compressed and stored for further use. Alternatively, the filtered gas can be subjected to further processing steps 6160. For example, in some embodiments, the filtered gas can be condensed to separate different gaseous compounds within the gas mixture. The different compounds can include, for example, various hydrocarbon products (e.g., alcohols, alkanes, alkenes, alkynes, ethers) produced during pyrolysis. In certain embodiments, the filtered gas containing a mixture of hydrocarbon components can be combined with steam gas 6170 (e.g., a mixture of water vapor and oxygen) and subjected to a cracking process to reduce molecular weights of the hydrocarbon components.

In some embodiments, the pyrolysis chamber includes heat sources that burn hydrocarbon gases such as methane, propane, and/or butane to heat the feedstock. A portion 6270 of the separated gases can be recirculated into the pyrolysis chamber for combustion, to generate process heat to sustain the pyrolysis process.

In certain embodiments, the pyrolysis chamber can receive process heat that can be used to increase the temperature of feedstock materials. For example, irradiating feedstock with radiation (e.g., gamma radiation, electron beam radiation, or other types of radiation) can heat the feedstock materials to relatively high temperatures. The heated feedstock materials can be cooled by a heat exchange system that removes some of the excess heat from the irradiated feedstock. The heat exchange system can be configured to transport some of the heat energy to the pyrolysis chamber to heat (or pre-heat) feedstock material, thereby reducing energy cost for the pyrolysis process.

The slurry containing liquid and solid pyrolysis products can undergo an optional de-watering step 6070, in which excess water can be removed from the slurry via processes such as mechanical pressing and evaporation. The excess water 6280 can be filtered and then recirculated for further use in quenching the pyrolysis decomposition products in step 6250.

The de-watered slurry then undergoes a mechanical separation step 6080, in which solid product material 6110 is separated from liquid product material 6090 by a series of increasingly fine filters. In step 6100, the liquid product material 6090 can then be condensed (e.g., via evaporation) to remove waste water 6190, and purified by processes such as extraction. Extraction can include the addition of one or more organic solvents 6180, for example, to separate products such as oils from products such as alcohols. Suitable organic solvents include, for example, various hydrocarbons and halohydrocarbons. The purified liquid products 6200 can then be subjected to further processing steps. Waste water 6190 can be filtered if necessary, and recirculated for further use in quenching the pyrolysis decomposition products in step 6250.

After separation in step 6080, the solid product material 6110 is optionally subjected to a drying step 6120 that can include evaporation of water. Solid material 6110 can then be stored for later use, or subjected to further processing steps, as appropriate.

The pyrolysis process parameters discussed above are exemplary. In general, values of these parameters can vary widely according to the nature of the feedstock and the desired products. Moreover, a wide variety of different pyrolysis techniques, including using heat sources such as hydrocarbon flames and/or furnaces, infrared lasers, microwave heaters, induction heaters, resistive heaters, and other heating devices and configurations can be used.

A wide variety of different pyrolysis chambers can be used to decompose the feedstock. In some embodiments, for example, pyrolyzing feedstock can include heating the material using a resistive heating member, such as a metal filament or metal ribbon. The heating can occur by direct contact between the resistive heating member and the material.

In certain embodiments, pyrolyzing can include heating the material by induction, such as by using a Curie-Point pyrolyzer. In some embodiments, pyrolyzing can include heating the material by the application of radiation, such as infrared radiation. The radiation can be generated by a laser, such as an infrared laser.

In certain embodiments, pyrolyzing can include heating the material with a convective heat. The convective heat can be generated by a flowing stream of heated gas. The heated gas can be maintained at a temperature of less than about 1200° C., such as less than 1000° C., less than 750° C., less than 600° C., less than 400° C. or even less than 300° C. The heated gas can be maintained at a temperature of greater than about 250° C. The convective heat can be generated by a hot body surrounding the first material, such as in a furnace.

In some embodiments, pyrolyzing can include heating the material with steam at a temperature above about 250° C.

Figure 15:
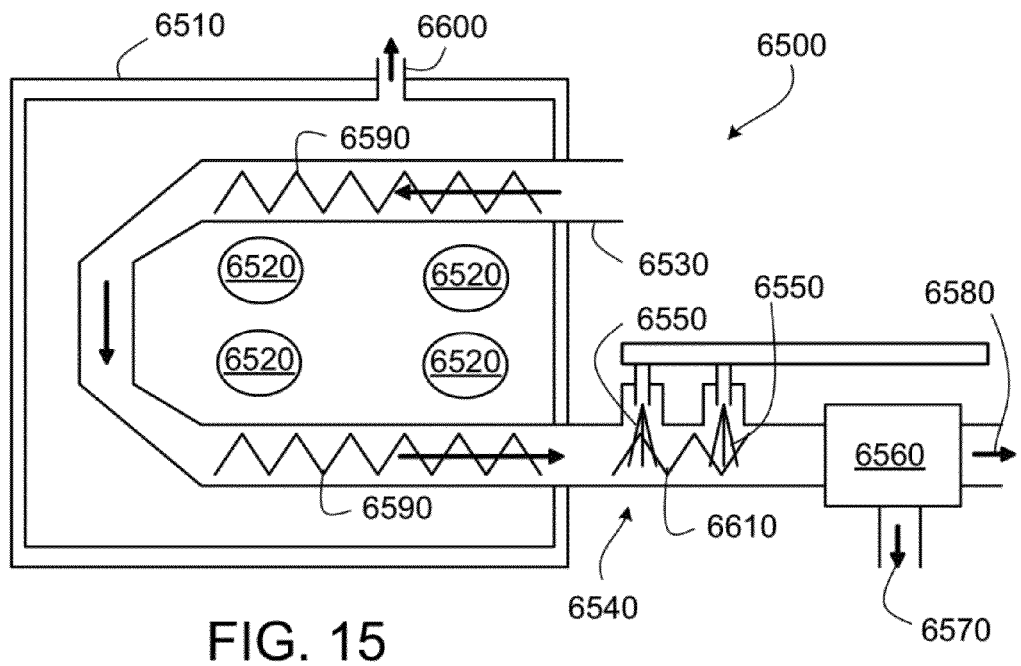
FIG. 15 is a cross-sectional side view of a pyrolysis chamber.

An embodiment of a pyrolysis chamber is shown in FIG. 15. Chamber 6500 includes an insulated chamber wall 6510 with a vent 6600 for exhaust gases, a plurality of burners 6520 that generate heat for the pyrolysis process, a transport duct 6530 for transporting the feedstock through chamber 6500, augers 6590 for moving the feedstock through duct 6530 in a turbulent flow, and a quenching system 6540 that includes an auger 6610 for moving the pyrolysis products, water jets 6550 for spraying the pyrolysis products with cooling water, and a gas separator for separating gaseous products 6580 from a slurry 6570 containing solid and liquid products.

Figure 16:
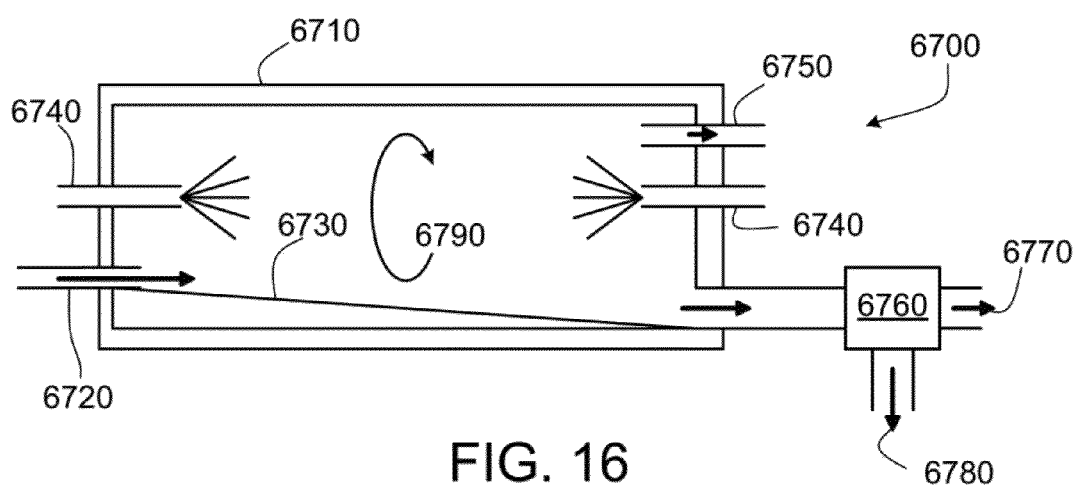
FIG. 16 is a cross-sectional side view of a pyrolysis chamber.

Another embodiment of a pyrolysis chamber is shown in FIG. 16. Chamber 6700 includes an insulated chamber wall 6710, a feedstock supply duct 6720, a sloped inner chamber wall 6730, burners 6740 that generate heat for the pyrolysis process, a vent 6750 for exhaust gases, and a gas separator 6760 for separating gaseous products 6770 from liquid and solid products 6780. Chamber 6700 is configured to rotate in the direction shown by arrow 6790 to ensure adequate mixing and turbulent flow of the feedstock within the chamber.

Figure 17:
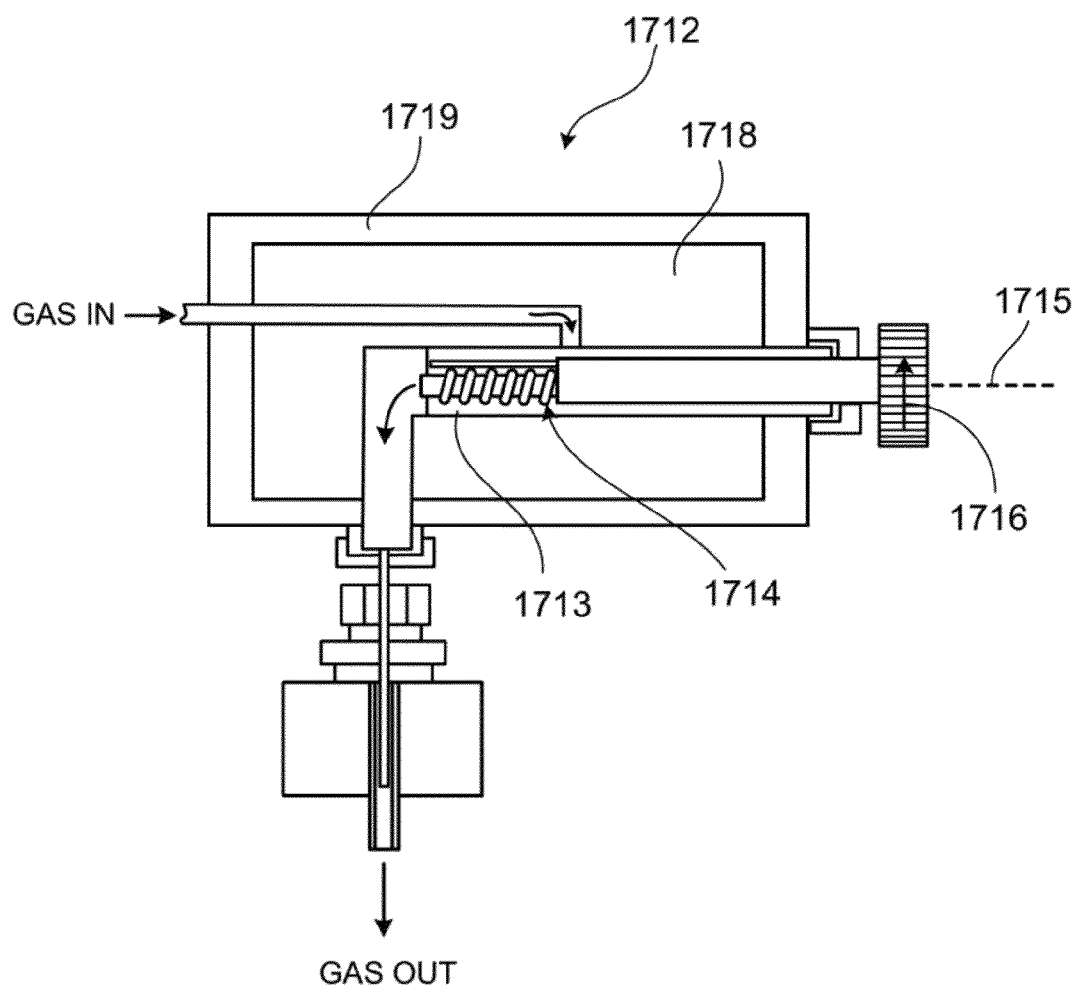
FIG. 17 is a cross-sectional side view of a pyrolyzer that includes a heated filament.

A further embodiment of a pyrolysis chamber is shown in FIG. 17. Filament pyrolyzer 1712 includes a sample holder 1713 with resistive heating element 1714 in the form of a wire winding through the open space defined by the sample holder

1713. Optionally, the heated element can be spun about axis 1715 (as indicated by arrow 1716) to tumble the material that includes the cellulosic material in sample holder 1713. The space 1718 defined by enclosure 1719 is maintained at a temperature above room temperature, e.g., 200 to 250° C. In a typical usage, a carrier gas, e.g., an inert gas, or an oxidizing or reducing gas, traverses through the sample holder 1713 while the resistive heating element is rotated and heated to a desired temperature, e.g., 325° C. After an appropriate time, e.g., 5 to 10 minutes, the pyrolyzed material is emptied from the sample holder. The system shown in FIG. 17 can be scaled and made continuous. For example, rather than a wire as the heating member, the heating member can be an auger screw. Material can continuously fall into the sample holder, striking a heated screw that pyrolyzes the material. At the same time, the screw can push the pyrolyzed material out of the sample holder to allow for the entry of fresh, unpyrolyzed material.

Figure 18:
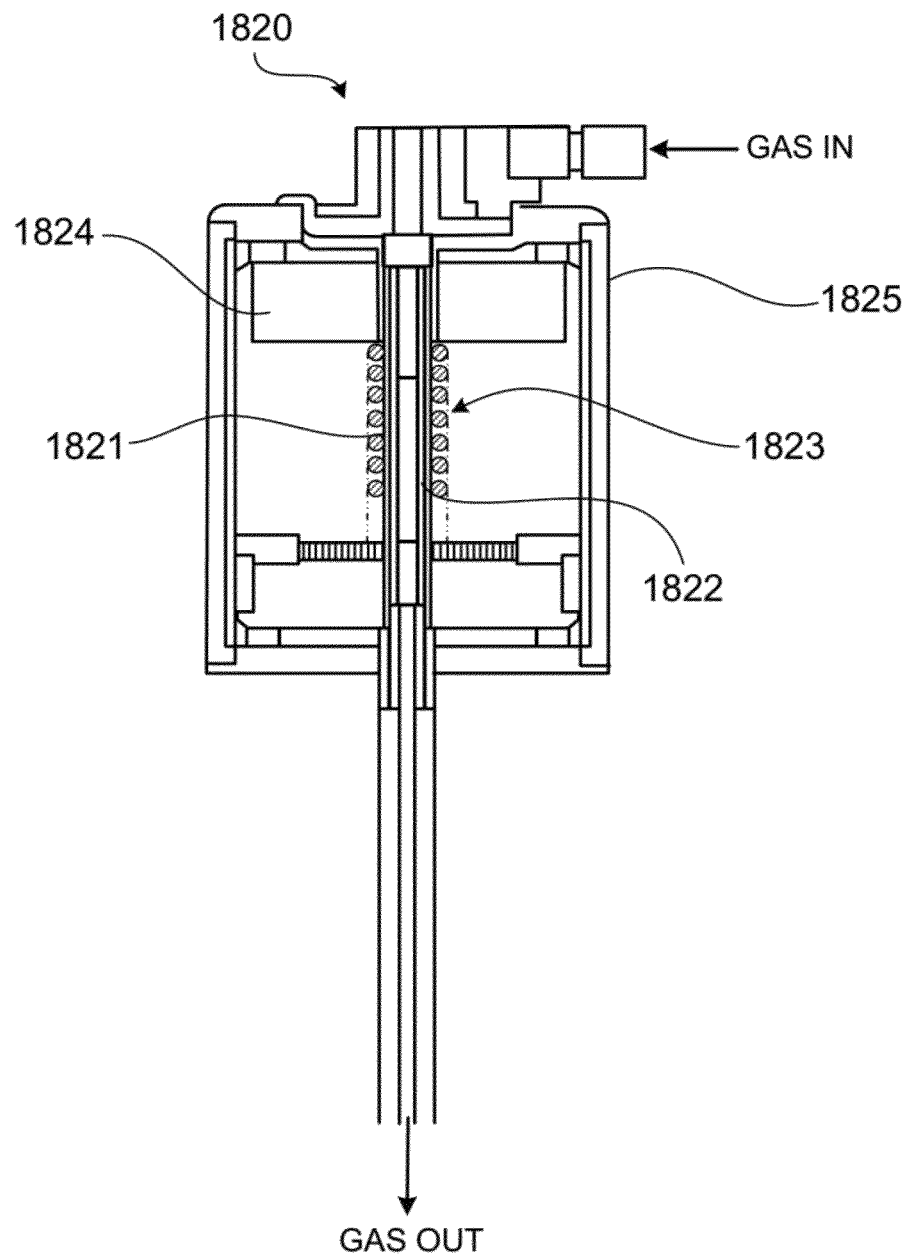
FIG. 18 is a schematic cross-sectional side view of a Curie-Point pyrolyzer.

Another embodiment of a pyrolysis chamber is shown in FIG. 18, which features a Curie-Point pyrolyzer 1820 that includes a sample chamber 1821 housing a ferromagnetic foil 1822. Surrounding the sample chamber 1821 is an RF coil 1823. The space 1824 defined by enclosure 1825 is maintained at a temperature above room temperature, e.g., 200 to 250° C. In a typical usage, a carrier gas traverses through the sample chamber 1821 while the foil 1822 is inductively heated by an applied RF field to pyrolize the material at a desired temperature.

Figure 19:
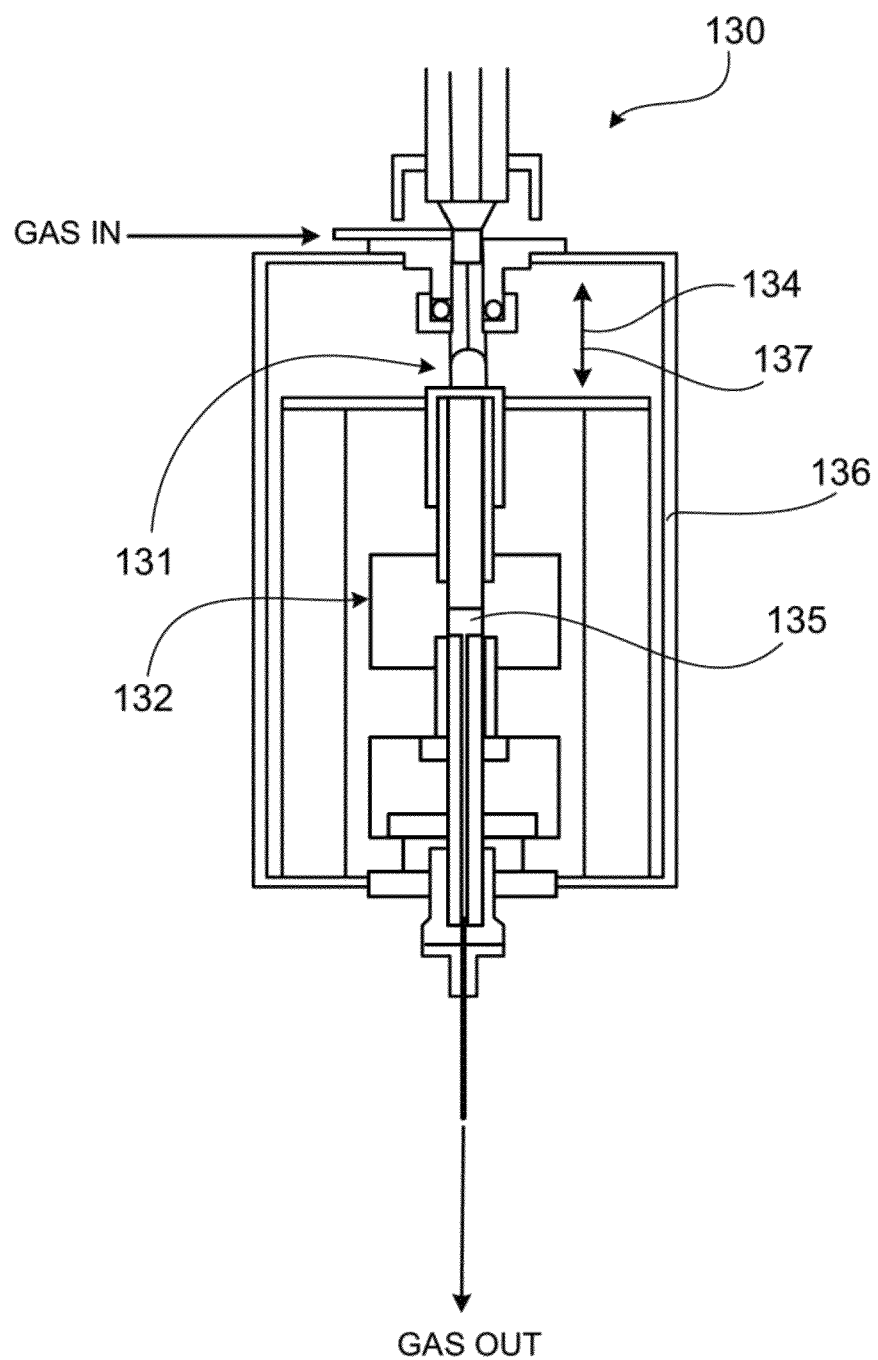
FIG. 19 is a schematic cross-sectional side view of a furnace pyrolyzer.

Yet another embodiment of a pyrolysis chamber is shown in FIG. 19. Furnace pyrolyzer 130 includes a movable sample holder 131 and a furnace 132. In a typical usage, the sample is lowered (as indicated by arrow 137) into a hot zone 135 of furnace 132, while a carrier gas fills the housing 136 and traverses through the sample holder 131. The sample is heated to the desired temperature for a desired time to provide a pyrolyzed product. The pyrolyzed product is removed from the pyrolyzer by raising the sample holder (as indicated by arrow 134).

Figure 20:
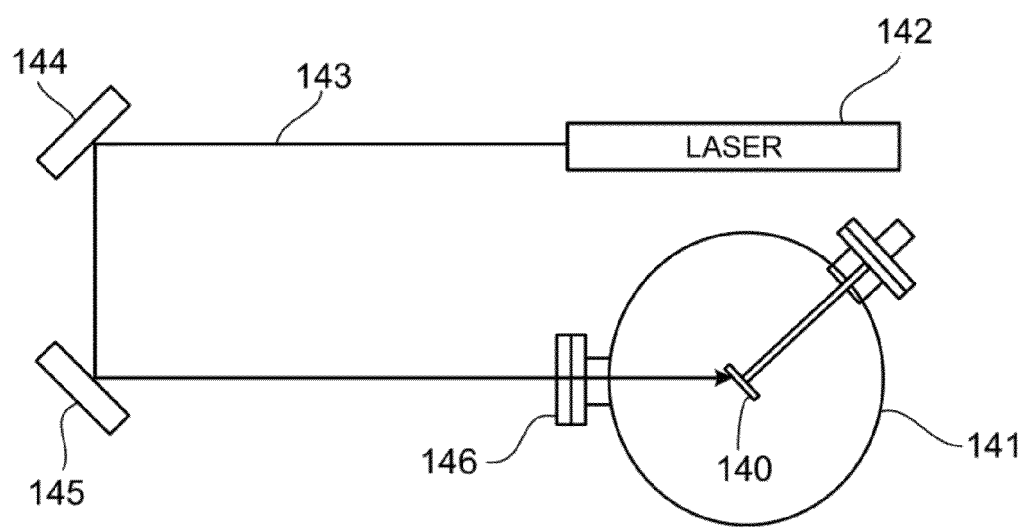
FIG. 20 is a schematic cross-sectional top view of a laser pyrolysis apparatus.

In certain embodiments, as shown in FIG. 20, a cellulosic target 140 can be pyrolyzed by treating the target, which is housed in a vacuum chamber 141, with laser light, e.g., light having a wavelength of from about 225 nm to about 1500 nm. For example, the target can be ablated at 266 nm, using the fourth harmonic of a Nd-YAG laser (Spectra Physics, GCR170, San Jose, Calif.). The optical configuration shown allows the nearly monochromatic light 143 generated by the laser 142 to be directed using mirrors 144 and 145 onto the target after passing through a lens 146 in the vacuum chamber 141. Typically, the pressure in the vacuum chamber is maintained at less than about $10^{-6}$ mm Hg. In some embodiments, infrared radiation is used, e.g., 1.06 micron radiation from an Nd-YAG laser. In such embodiments, an infrared sensitive dye can be combined with the cellulosic material to produce a cellulosic target. The infrared dye can enhance the heating of the cellulosic material. Laser ablation is described by Blanchet-Fincher et al., in U.S. Pat. No. 5,942,649.

Figure 21:
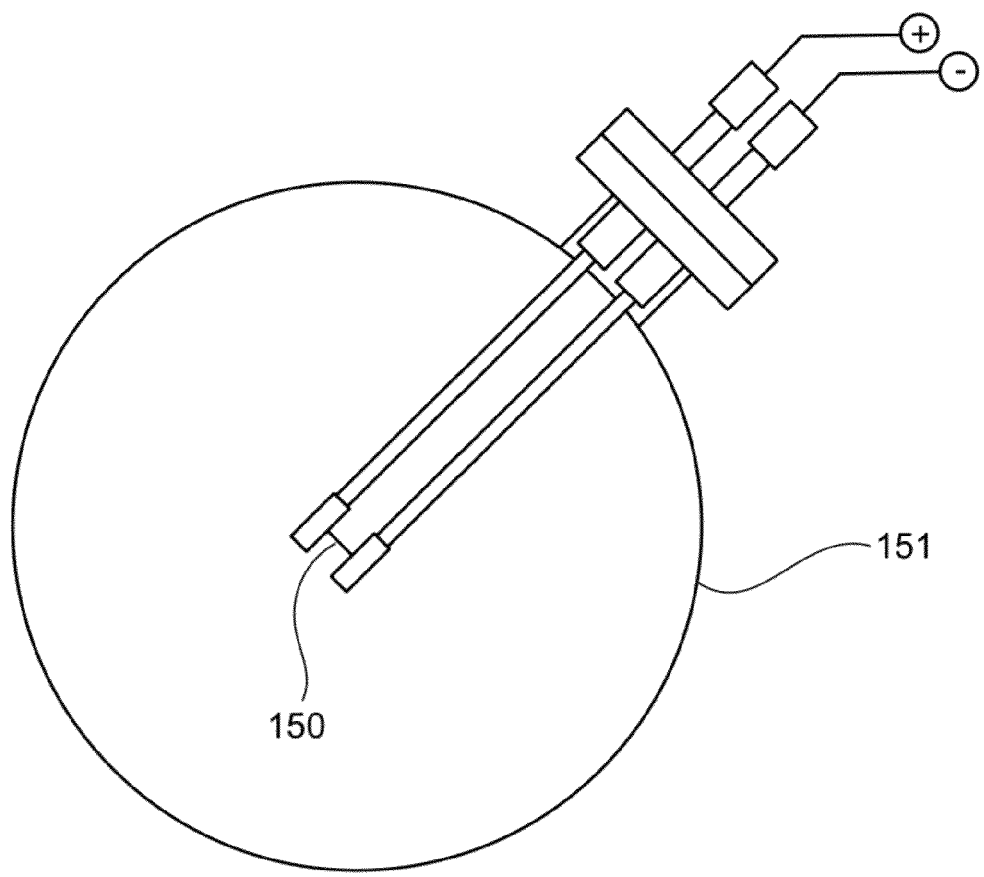
FIG. 21 is a schematic cross-sectional top view of a tungsten filament flash pyrolyzer.

Referring to FIG. 21, in some embodiments, a cellulosic material can be flash pyrolyzed by coating a tungsten filament 150, such as a 5 to 25 mil tungsten filament, with the desired cellulosic material while the material is housed in a vacuum chamber 151. To affect pyrolysis, current is passed through the filament, which causes a rapid heating of the filament for a desired time. Typically, the heating is continued for seconds before allowing the filament to cool. In some embodiments, the heating is performed a number of times to effect the desired amount of pyrolysis.

In certain embodiments, carbohydrate-containing biomass material can be heated in an absence of oxygen in a fluidized bed reactor. If desired, the carbohydrate containing biomass can have relatively thin cross-sections, and can include any of the fibrous materials described herein, for efficient heat transfer. The material can be heated by thermal transfer from a hot metal or ceramic, such as glass beads or sand in the reactor, and the resulting pyrolysis liquid or oil can be transported to a central refinery for making combustible fuels or other useful products.

In some embodiments, irradiating the biomass material, e.g., with a beam of particles, such as electrons, prior to pyrolysis can lower the pyrolysis temperature, resulting in less energy being consumed during pyrolysis.

Oxidation

One or more oxidative processing sequences can be used to process raw feedstock from a wide variety of different sources to extract useful substances from the feedstock, and to provide partially degraded organic material which functions as input to further processing steps and/or sequences.

Referring again to FIG. 8, a first material 2 that includes cellulose having a first number average molecular weight ($^{T}M_{n1}$) and having a first oxygen content ($^{T}O_1$) is oxidized, e.g., by heating the first material in a tube furnace in stream of air or oxygen-enriched air, to provide a second material 3 that includes cellulose having a second number average molecular weight ($^{T}M_{n2}$) and having a second oxygen content ($^{T}O_2$) higher than the first oxygen content ($^{T}O_1$). The second material (or the first and second material in certain embodiments) can be, e.g., combined with a resin, such as a molten thermoplastic resin or a microorganism, to provide a composite 4 having desirable mechanical properties, or a fuel 5

Such materials can also be combined with a solid and/or a liquid. For example, the liquid can be in the form of a solution and the solid can be particulate in form. The liquid and/or solid can include a microorganism, e.g., a bacterium, and/or an enzyme. For example, the bacterium and/or enzyme can work on the cellulosic or lignocellulosic material to produce a fuel, such as ethanol, or a coproduct, such as a protein. Fuels and coproducts are described in FIBROUS MATERIALS AND COMPOSITES," U.S. Ser. No. 11/453,951, filed Jun. 15, 2006. The entire contents of each of the foregoing applications are incorporated herein by reference.

In some embodiments, the second number average molecular weight is not more than 97 percent lower than the first number average molecular weight, e.g., not more than 95 percent, 90, 85, 80, 75, 70, 65, 60, 55, 50, 45, 40, 30, 20, 12.5, 10.0, 7.5, 5.0, 4.0, 3.0, 2.5, 2.0 or not more than 1.0 percent lower than the first number average molecular weight. The amount of reduction of molecular weight will depend upon the application.

In some embodiments in which the materials are used to make a fuel or a coproduct, the starting number average molecular weight (prior to oxidation) is from about 200,000 to about 3,200,000, e.g., from about 250,000 to about 1,000,000 or from about 250,000 to about 700,000, and the number average molecular weight after oxidation is from about 50,000 to about 200,000, e.g., from about 60,000 to about 150,000 or from about 70,000 to about 125,000. However, in some embodiments, e.g., after extensive oxidation, it is possible to have a number average molecular weight of less than about 10,000 or even less than about 5,000.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the oxygen content of the first material. Oxygen content is measured by elemental analysis by pyrolyzing a sample in a furnace operating 1300° C. or higher. A suitable elemental analyzer is the LECO CHNS-932 analyzer with a VTF-900 high temperature pyrolysis furnace.

In some embodiments, oxidation of first material 200 does not result in a substantial change in the crystallinity of the cellulose. However, in some instances, e.g., after extreme oxidation, the second material has cellulose that has as crystallinity ($^TC_2$) that is lower than the crystallinity ($^TC_1$) of the cellulose of the first material. For example, ($^TC_2$) can be lower than ($^TC_1$) by more than about 5 percent, e.g., 10, 15, 20, or even 25 percent. This can be desirable to enhance solubility of the materials in a liquid, such as a liquid that includes a bacterium and/or an enzyme.

In some embodiments, the starting crystallinity index (prior to oxidation) is from about 40 to about 87.5 percent, e.g., from about 50 to about 75 percent or from about 60 to about 70 percent, and the crystallinity index after oxidation is from about 30 to about 75.0 percent, e.g., from about 35.0 to about 70.0 percent or from about 37.5 to about 65.0 percent. However, in certain embodiments, e.g., after extensive oxidation, it is possible to have a crystallinity index of lower than 5 percent. In some embodiments, the material after oxidation is substantially amorphous.

Without wishing to be bound by any particular theory, it is believed that oxidation increases the number of hydrogen-bonding groups on the cellulose, such as hydroxyl groups, aldehyde groups, ketone groups carboxylic acid groups or anhydride groups, which can increase its dispersibility and/or its solubility (e.g., in a liquid). To further improve dispersibility in a resin, the resin can include a component that includes hydrogen-bonding groups, such as one or more anhydride groups, carboxylic acid groups, hydroxyl groups, amide groups, amine groups or mixtures of any of these groups. In some preferred embodiments, the component includes a polymer copolymerized with and/or grafted with maleic anhydride. Such materials are available from Dupont under the tradename FUSABOND®.

Generally, oxidation of first material 200 occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Oxidation Systems

Figure 22:
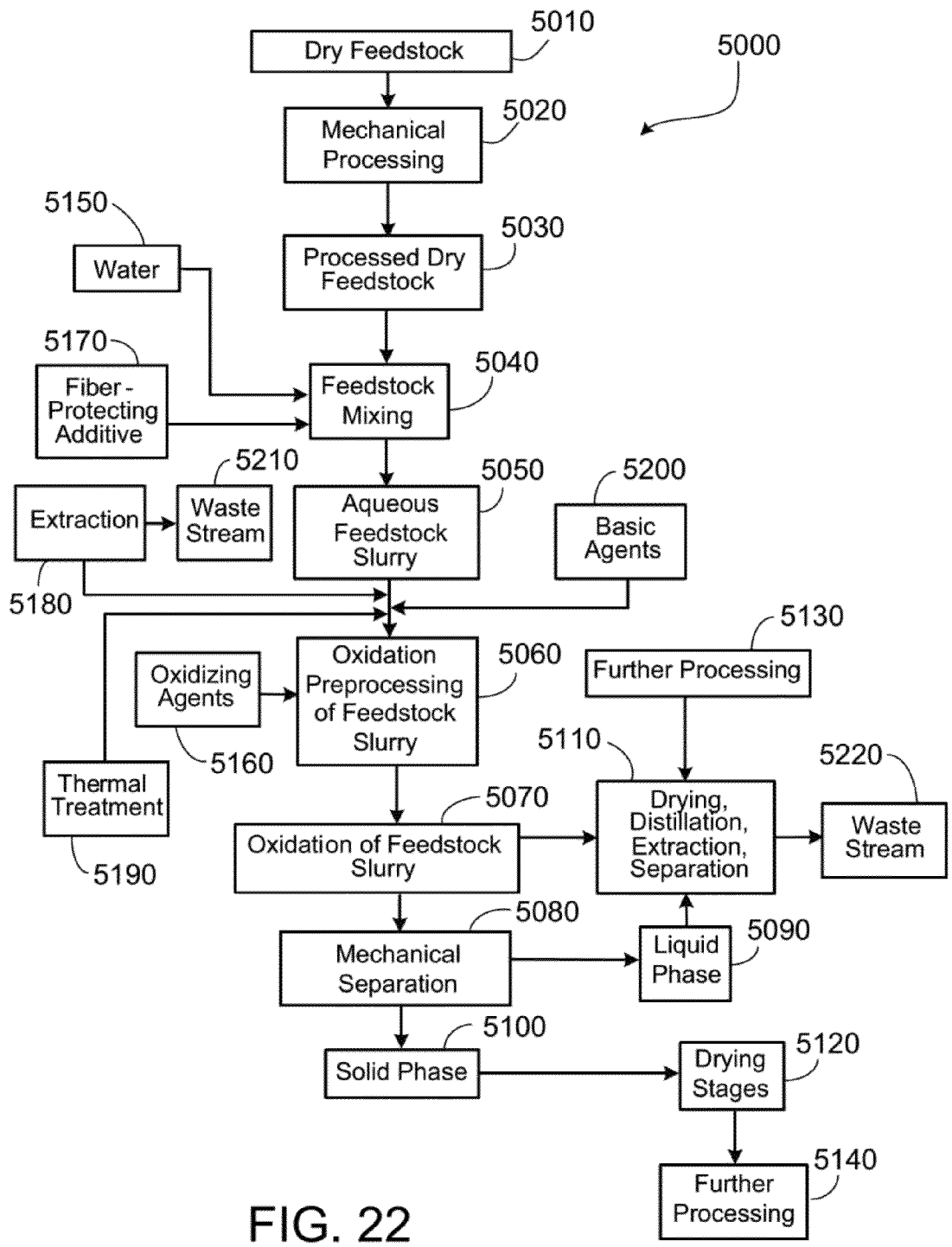
FIG. 22 is a block diagram illustrating an oxidative feedstock pretreatment system.

FIG. 22 shows a process flow diagram 5000 that includes various steps in an oxidative feedstock pretreatment system. In first step 5010, a supply of dry feedstock is received from a feed source. The feed source can include, for example, a storage bed or container that is connected to an in-line oxidation reactor via a conveyor belt or another feedstock transport device.

As described above, the dry feedstock from the feed source may be pre-processed prior to delivery to the oxidation reactor. For example, if the feedstock is derived from plant sources, certain portions of the plant material may be removed prior to collection of the plant material and/or before the plant material is delivered by the feedstock transport device. Alternatively, or in addition, the biomass feedstock can be subjected to mechanical processing (e.g., to reduce the average length of fibers in the feedstock) prior to delivery to the oxidation reactor.

Following mechanical processing 5020, feedstock 5030 is transported to a mixing system which introduces water 5150 into the feedstock in a mechanical mixing process. Combining water with the processed feedstock in mixing step 5040 creates an aqueous feedstock slurry 5050, which can then be treated with one or more oxidizing agents.

Typically, one liter of water is added to the mixture for every 0.02 kg to 1.0 kg of dry feedstock. The ratio of feedstock to water in the mixture depends upon the source of the feedstock and the specific oxidizing agents used further downstream in the overall process. For example, in typical industrial processing sequences for lignocellulosic biomass, aqueous feedstock slurry 5050 includes from about 0.5 kg to about 1.0 kg of dry biomass per liter of water.

In some embodiments, one or more fiber-protecting additives 5170 can also be added to the feedstock slurry in feedstock mixing step 5040. Fiber-protecting additives help to reduce degradation of certain types of biomass fibers (e.g., cellulose fibers) during oxidation of the feedstock. Fiber-protecting additives can be used, for example, if a desired product from processing a lignocellulosic feedstock includes cellulose fibers. Exemplary fiber-protecting additives include magnesium compounds such as magnesium hydroxide. Concentrations of fiber-protecting additives in feedstock slurry 5050 can be from 0.1% to 0.4% of the dry weight of the biomass feedstock, for example.

In certain embodiments, aqueous feedstock slurry 5050 can be subjected to an optional extraction 5180 with an organic solvent to remove water-insoluble substances from the slurry. For example, extraction of slurry 5050 with one or more organic solvents yields a purified slurry and an organic waste stream 5210 that includes water-insoluble materials such as fats, oils, and other non-polar, hydrocarbon-based substances. Suitable solvents for performing extraction of slurry 5050 include various alcohols, hydrocarbons, and halo-hydrocarbons, for example.

In some embodiments, aqueous feedstock slurry 5050 can be subjected to an optional thermal treatment 5190 to further prepare the feedstock for oxidation. An example of a thermal treatment includes heating the feedstock slurry in the presence of pressurized steam. In fibrous biomass feedstock, the pressurized steam swells the fibers, exposing a larger fraction of fiber surfaces to the aqueous solvent and to oxidizing agents that are introduced in subsequent processing steps.

In certain embodiments, aqueous feedstock slurry 5050 can be subjected to an optional treatment with basic agents 5200. Treatment with one or more basic agents can help to separate lignin from cellulose in lignocellulosic biomass feedstock, thereby improving subsequent oxidation of the feedstock. Exemplary basic agents include alkali and alkaline earth hydroxides such as sodium hydroxide, potassium hydroxide, and calcium hydroxide. In general, a variety of basic agents can be used, typically in concentrations from about 0.01% to about 0.5% of the dry weight of the feedstock.

Aqueous feedstock slurry 5050 is transported (e.g., by an in-line piping system) to a chamber, which can be an oxidation preprocessing chamber or an oxidation reactor. In oxidation preprocessing step 5060, one or more oxidizing agents 5160 are added to feedstock slurry 5050 to form an oxidizing medium. In some embodiments, for example, oxidizing agents 5160 can include hydrogen peroxide. Hydrogen peroxide can be added to slurry 5050 as an aqueous solution, and in proportions ranging from 3% to between 30% and 35% by weight of slurry 5050. Hydrogen peroxide has a number of advantages as an oxidizing agent. For example, aqueous hydrogen peroxide solution is relatively inexpensive, is relatively chemically stable, and is not particularly hazardous relative to other oxidizing agents (and therefore does not require burdensome handling procedures and expensive safety equipment). Moreover, hydrogen peroxide decomposes to form water during oxidation of feedstock, so that waste stream cleanup is relatively straightforward and inexpensive.

In certain embodiments, oxidizing agents 5160 can include oxygen (e.g., oxygen gas) either alone, or in combination with hydrogen peroxide. Oxygen gas can be bubbled into slurry 5050 in proportions ranging from 0.5% to 10% by weight of slurry 5050. Alternatively, or in addition, oxygen gas can also be introduced into a gaseous phase in equilibrium with slurry 5050 (e.g., a vapor head above slurry 5050). The oxygen gas can be introduced into either an oxidation preprocessing chamber or into an oxidation reactor (or into both), depending upon the configuration of the oxidative processing system. Typically, for example, the partial pressure of oxygen in the vapor above slurry 5050 is larger than the ambient pressure of oxygen, and ranges from 0.5 bar to 35 bar, depending upon the nature of the feedstock.

The oxygen gas can be introduced in pure form, or can be mixed with one or more carrier gases. For example, in some embodiments, high-pressure air provides the oxygen in the vapor. In certain embodiments, oxygen gas can be supplied continuously to the vapor phase to ensure that a concentration of oxygen in the vapor remains within certain predetermined limits during processing of the feedstock. In some embodiments, oxygen gas can be introduced initially in sufficient concentration to oxidize the feedstock, and then the feedstock can be transported to a closed, pressurized vessel (e.g., an oxidation reactor) for processing.

In certain embodiments, oxidizing agents 5160 can include nascent oxygen (e.g., oxygen radicals). Typically, nascent oxygen is produced as needed in an oxidation reactor or in a chamber in fluid communication with an oxidation reactor by one or more decomposition reactions. For example, in some embodiments, nascent oxygen can be produced from a reaction between NO and $O_2$ in a gas mixture or in solution. In certain embodiments, nascent oxygen can be produced from decomposition of HOCl in solution. Other methods by which nascent oxygen can be produced include via electrochemical generation in electrolyte solution, for example.

In general, nascent oxygen is an efficient oxidizing agent due to the relatively high reactivity of the oxygen radical. However, nascent oxygen can also be a relatively selective oxidizing agent. For example, when lignocellulosic feedstock is treated with nascent oxygen, selective oxidation of lignin occurs in preference to the other components of the feedstock such as cellulose. As a result, oxidation of feedstock with nascent oxygen provides a method for selective removal of the lignin fraction in certain feedstocks. Typically, nascent oxygen concentrations of between about 0.5% and 5% of the dry weight of the feedstock are used to effect efficient oxidation.

Without wishing to be bound by theory, it is believed that nascent oxygen reacts with lignocellulosic feedstock according to at least two different mechanisms. In a first mechanism, nascent oxygen undergoes an addition reaction with the lignin, resulting in partial oxidation of the lignin, which solubilizes the lignin in aqueous solution. As a result, the solubilized lignin can be removed from the rest of the feedstock via washing. In a second mechanism, nascent oxygen disrupts butane cross-links and/or opens aromatic rings that are connected via the butane cross-links. As a result, solubility of the lignin in aqueous solution increases, facilitating separation of the lignin fraction from the remainder of the feedstock via washing.

In some embodiments, oxidizing agents 5160 include ozone ($O_3$). The use of ozone can introduce several chemical handling considerations in the oxidation processing sequence. If heated too vigorously, an aqueous solution of ozone can decompose violently, with potentially adverse consequences for both human system operators and system equipment. Accordingly, ozone is typically generated in a thermally isolated, thick-walled vessel separate from the vessel that contains the feedstock slurry, and transported thereto at the appropriate process stage.

Without wishing to be bound by theory, it is believed that ozone decomposes into oxygen and oxygen radicals, and that the oxygen radicals (e.g., nascent oxygen) are responsible for the oxidizing properties of ozone in the manner discussed above. Ozone typically preferentially oxidizes the lignin fraction in lignocellulosic materials, leaving the cellulose fraction relatively undisturbed.

Conditions for ozone-based oxidation of biomass feedstock generally depend upon the nature of the biomass. For example, for cellulosic and/or lignocellulosic feedstocks, ozone concentrations of from 0.1 $g/m^3$ to 20 $g/m^3$ of dry feedstock provide for efficient feedstock oxidation. Typically, the water content in slurry 5050 is between 10% by weight and 80% by weight (e.g., between 40% by weight and 60% by weight). During ozone-based oxidation, the temperature of slurry 5050 can be maintained between 0° C. and 100° C. to avoid violent decomposition of the ozone.

In some embodiments, feedstock slurry 5050 can be treated with an aqueous, alkaline solution that includes one or more alkali and alkaline earth hydroxides such as sodium hydroxide, potassium hydroxide, and calcium hydroxide, and then treated thereafter with an ozone-containing gas in an oxidation reactor. This process has been observed to significantly increase decomposition of the biomass in slurry 5050. Typically, for example, a concentration of hydroxide ions in the alkaline solution is between 0.001% and 10% by weight of slurry 5050. After the feedstock has been wetted via contact with the alkaline solution, the ozone-containing gas is introduced into the oxidation reactor, where it contacts and oxidizes the feedstock.

Oxidizing agents 5160 can also include other substances. In some embodiments, for example, halogen-based oxidizing agents such as chlorine and oxychlorine agents (e.g., hypochlorite) can be introduced into slurry 5050. In certain embodiments, nitrogen-containing oxidizing substances can be introduced into slurry 5050. Exemplary nitrogen-containing oxidizing substances include NO and $NO_2$, for example. Nitrogen-containing agents can also be combined with oxygen in slurry 5050 to create additional oxidizing agents. For example, NO and $NO_2$ both combine with oxygen in slurry 5050 to form nitrate compounds, which are effective oxidizing agents for biomass feedstock. Halogen- and nitrogen-based oxidizing agents can, in some embodiments, cause bleaching of the biomass feedstock, depending upon the nature of the feedstock. The bleaching may be desirable for certain biomass-derived products that are extracted in subsequent processing steps.

Other oxidizing agents can include, for example, various peroxyacids, peroxyacetic acids, persulfates, percarbonates, permanganates, osmium tetroxide, and chromium oxides.

Following oxidation preprocessing step 5060, feedstock slurry 5050 is oxidized in step 5070. If oxidizing agents 5160 were added to slurry 5050 in an oxidation reactor, then oxidation proceeds in the same reactor. Alternatively, if oxidizing agents 5160 were added to slurry 5050 in a preprocessing chamber, then slurry 5050 is transported to an oxidation reactor via an in-line piping system. Once inside the oxidation reactor, oxidation of the biomass feedstock proceeds under a controlled set of environmental conditions. Typically, for example, the oxidation reactor is a cylindrical vessel that is closed to the external environment and pressurized. Both batch and continuous operation is possible, although environmental conditions are typically easier to control in in-line batch processing operations.

Oxidation of feedstock slurry 5050 typically occurs at elevated temperatures in the oxidation reactor. For example, the temperature of slurry 5050 in the oxidation reactor is typically maintained above 100° C., e.g., in a range from 120° C. to 240° C. For many types of biomass feedstock, oxidation is particularly efficient if the temperature of slurry 5050 is maintained between 150° C. and 220° C. Slurry 5050 can be heating using a variety of thermal transfer devices. For example, in some embodiments, the oxidation reactor contacts a heating bath that includes oil or molten salts. In certain embodiments, a series of heat exchange pipes surround and contact the oxidation reactor, and circulation of hot fluid within the pipes heats slurry 5050 in the reactor. Other heating devices that can be used to heat slurry 5050 include resistive heating elements, induction heaters, and microwave sources, for example.

The residence time of feedstock slurry 5050 in the oxidation reactor can be varied as desired to process the feedstock. Typically, slurry 5050 spends from 1 minute to 60 minutes undergoing oxidation in the reactor. For relatively soft biomass material such as lignocellulosic matter, the residence time in the oxidation reactor can be from 5 minutes to 30 minutes, for example, at an oxygen pressure of between 3 and 12 bars in the reactor, and at a slurry temperature of between 160° C. and 210° C. For other types of feedstock, however, residence times in the oxidation reactor can be longer, e.g., as long 48 hours. To determine appropriate residence times for slurry 5050 in the oxidation reactor, aliquots of the slurry can be extracted from the reactor at specific intervals and analyzed to determine concentrations of particular products of interest such as complex saccharides. Information about the increase in concentrations of certain products in slurry 5050 as a function of time can be used to determine residence times for particular classes of feedstock material.

In some embodiments, during oxidation of feedstock slurry 5050, adjustment of the slurry pH may be performed by introducing one or more chemical agents into the oxidation reactor. For example, in certain embodiments, oxidation occurs most efficiently in a pH range of about 9-11. To maintain a pH in this range, agents such as alkali and alkaline earth hydroxides, carbonates, ammonia, and alkaline buffer solutions can be introduced into the oxidation reactor.

Circulation of slurry 5050 during oxidation can be important to ensure sufficient contact between oxidizing agents 5160 and the feedstock. Circulation of the slurry can be achieved using a variety of techniques. For example, in some embodiments, a mechanical stirring apparatus that includes impeller blades or a paddle wheel can be implemented in the oxidation reactor. In certain embodiments, the oxidation reactor can be a loop reactor, in which the aqueous solvent in which the feedstock is suspended is simultaneously drained from the bottom of the reactor and recirculated into the top of the reactor via pumping, thereby ensuring that the slurry is continually re-mixed and does not stagnate within the reactor.

After oxidation of the feedstock is complete, the slurry is transported to a separation apparatus where a mechanical separation step 5080 occurs. Typically, mechanical separation step 5080 includes one or more stages of increasingly fine filtering of the slurry to mechanically separate the solid and liquid constituents.

Liquid phase 5090 is separated from solid phase 5100, and the two phases are processed independently thereafter. Solid phase 5100 can optionally undergo a drying step 5120 in a drying apparatus, for example. Drying step 5120 can include, for example, mechanically dispersing the solid material onto a drying surface, and evaporating water from solid phase 5100 by gentle heating of the solid material. Following drying step 5120 (or, alternatively, without undergoing drying step 5120), solid phase 5100 is transported for further processing steps 5140.

Liquid phase 5090 can optionally undergo a drying step 5110 to reduce the concentration of water in the liquid phase. In some embodiments, for example, drying step 5110 can include evaporation and/or distillation and/or extraction of water from liquid phase 5090 by gentle heating of the liquid. Alternatively, or in addition, one or more chemical drying agents can be used to remove water from liquid phase 5090. Following drying step 5110 (or alternatively, without undergoing drying step 5110), liquid phase 5090 is transported for further processing steps 5130, which can include a variety of chemical and biological treatment steps such as chemical and/or enzymatic hydrolysis.

Drying step 5110 creates waste stream 5220, an aqueous solution that can include dissolved chemical agents such as acids and bases in relatively low concentrations. Treatment of waste stream 5220 can include, for example, pH neutralization with one or more mineral acids or bases. Depending upon the concentration of dissolved salts in waste stream 5220, the solution may be partially de-ionized (e.g., by passing the waste stream through an ion exchange system). Then, the waste stream—which includes primarily water—can be re-circulated into the overall process (e.g., as water 5150), diverted to another process, or discharged.

Typically, for lignocellulosic biomass feedstocks following separation step 5070, liquid phase 5090 includes a variety of soluble poly- and oligosaccharides, which can then be separated and/or reduced to smaller-chain saccharides via further processing steps. Solid phase 5100 typically includes primarily cellulose, for example, with smaller amounts of hemicellulose- and lignin-derived products.

In some embodiments, oxidation can be carried out at elevated temperature in a reactor such as a pyrolysis chamber. For example, referring again to FIG. 17, feedstock materials can be oxidized in filament pyrolyzer 1712. In a typical usage, an oxidizing carrier gas, e.g., air or an air/argon blend, traverses through the sample holder 1713 while the resistive heating element is rotated and heated to a desired temperature, e.g., 325° C. After an appropriate time, e.g., 5 to 10 minutes, the oxidized material is emptied from the sample holder. The system shown in FIG. 17 can be scaled and made continuous. For example, rather than a wire as the heating member, the heating member can be an auger screw. Material can continuously fall into the sample holder, striking a heated screw that pyrolizes the material. At the same time, the screw can push the oxidized material out of the sample holder to allow for the entry of fresh, unoxidized material.

Feedstock materials can also be oxidized in any of the pyrolysis systems shown in FIGS. 18-20 and described above in the Pyrolysis Systems section.

Referring again to FIG. 21, feedstock materials can be rapidly oxidized by coating a tungsten filament 150, together with an oxidant, such as a peroxide, with the desired cellulosic material while the material is housed in a vacuum chamber 151. To affect oxidation, current is passed through the filament, which causes a rapid heating of the filament for a desired time. Typically, the heating is continued for seconds before allowing the filament to cool. In some embodiments, the heating is performed a number of times to effect the desired amount of oxidation.

Referring again to FIG. 12, in some embodiments, feedstock materials can be oxidized with the aid of sound and/or cavitation. Generally, to effect oxidation, the materials are sonicated in an oxidizing environment, such as water saturated with oxygen or another chemical oxidant, such as hydrogen peroxide.

Referring again to FIGS. 9 and 10, in certain embodiments, ionizing radiation is used to aid in the oxidation of feedstock materials. Generally, to effect oxidation, the materials are irradiated in an oxidizing environment, such as air or oxygen. For example, gamma radiation and/or electron beam radiation can be employed to irradiate the materials.

Other Processes

Steam explosion can be used alone without any of the processes described herein, or in combination with any one or more of the processes described herein.

Figure 23:
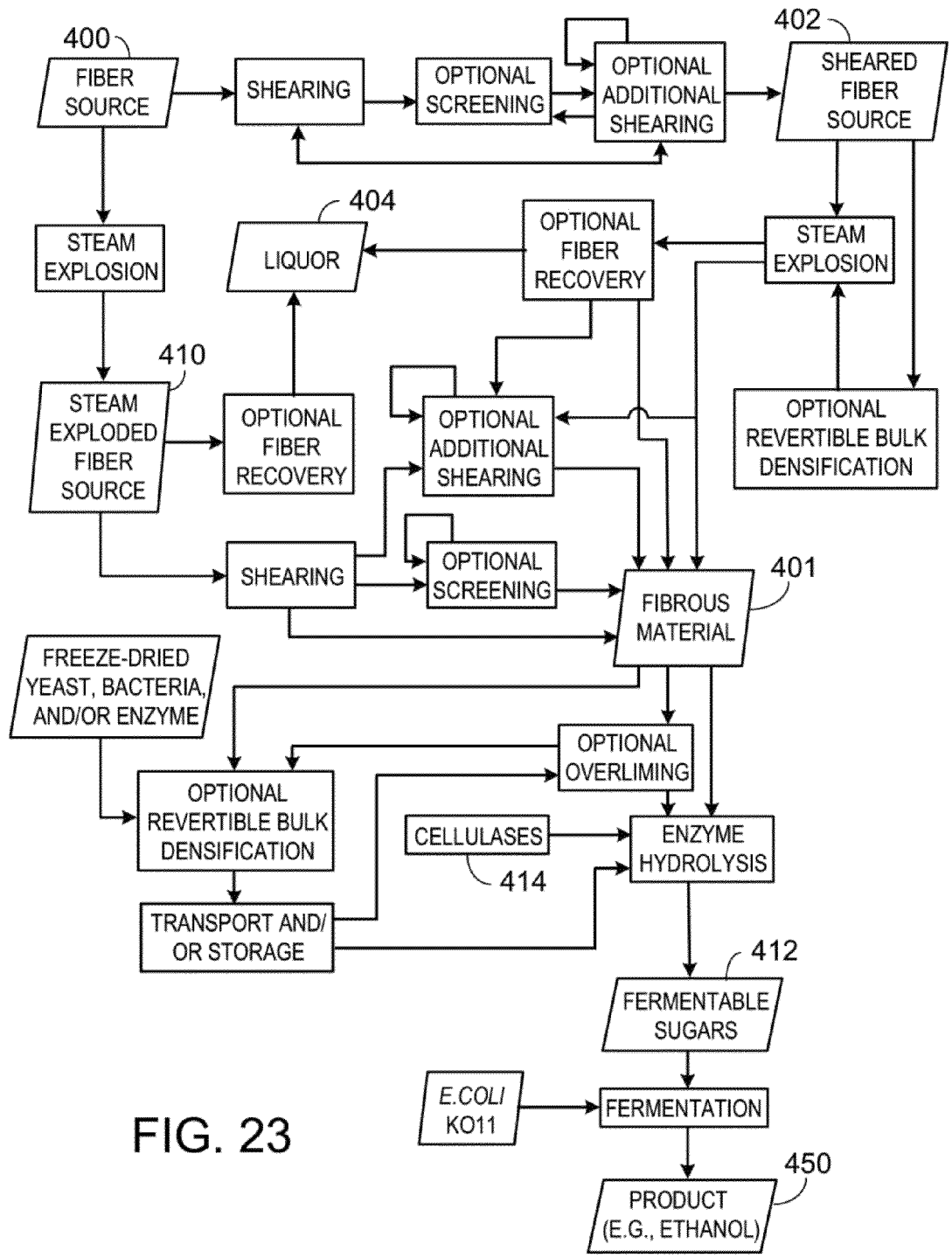
FIG. 23 is block diagram illustrating a general overview of the process of converting a fiber source into a product, e.g., ethanol.

FIG. 23 shows an overview of the entire process of converting a fiber source or feedstock 400 into a product 450, such as ethanol, by a process that includes shearing and steam explosion to produce a fibrous material 401, which is then hydrolyzed and converted, e.g., fermented, to produce the product. The fiber source can be transformed into the fibrous material 401 through a number of possible methods, including at least one shearing process and at least one steam explosion process.

For example, one option includes shearing the fiber source, followed by optional screening step(s) and optional additional shearing step(s) to produce a sheared fiber source 402, which can then be steam exploded to produce the fibrous material 401. The steam explosion process is optionally followed by a fiber recovery process to remove liquids or the "liquor" 404, resulting from the steam exploding process. The material resulting from steam exploding the sheared fiber source may be further sheared by optional additional shearing step(s) and/or optional screening step(s).

In another method, the fibrous material 401 is first steam exploded to produce a steam exploded fiber source 410. The resulting steam exploded fiber source is then subjected to an optional fiber recovery process to remove liquids, or the liquor. The resulting steam exploded fiber source can then be sheared to produce the fibrous material. The steam exploded fiber source can also be subject to one or more optional screening steps and/or one or more optional additional shearing steps. The process of shearing and steam exploding the fiber source to produce the sheared and steam exploded fibrous material will be further discussed below.

The fiber source can be cut into pieces or strips of confetti material prior to shearing or steam explosion. The shearing processes can take place with the material in a dry state (e.g., having less than 0.25 percent by weight absorbed water), a hydrated state, or even while the material is partially or fully submerged in a liquid, such as water or isopropanol. The process can also optimally include steps of drying the output after steam exploding or shearing to allow for additional steps of dry shearing or steam exploding. The steps of shearing, screening, and steam explosion can take place with or without the presence of various chemical solutions.

In a steam explosion process, the fiber source or the sheared fiber source is contacted with steam under high pressure, and the steam diffuses into the structures of the fiber source (e.g., the lignocellulosic structures). The steam then condenses under high pressure thereby "wetting" the fiber source. The moisture in the fiber source can hydrolyze any acetyl groups in the fiber source (e.g., the acetyl groups in the hemicellulose fractions), forming organic acids such as acetic and uronic acids. The acids, in turn, can catalyze the depolymerization of hemicellulose, releasing xylan and limited amounts of glucan. The "wet" fiber source (or sheared fiber source, etc.) is then "exploded" when the pressure is released. The condensed moisture instantaneously evaporates due to the sudden decrease in pressure and the expansion of the water vapor exerts a shear force upon the fiber source (or sheared fiber source, etc.). A sufficient shear force will cause the mechanical breakdown of the internal structures (e.g., the lignocellulosic structures) of the fiber source.

The sheared and steam exploded fibrous material is then converted into a useful product, such as ethanol. In some embodiments, the fibrous material is converted into a fuel. One method of converting the fibrous material into a fuel is by hydrolysis to produce fermentable sugars, 412, which are then fermented to produce the product. Other methods of converting fibrous materials into fuels may also be used.

In some embodiments, prior to combining with the microorganism, the sheared and steam exploded fibrous material 401 is sterilized to kill any competing microorganisms that may be on the fibrous material. For example, the fibrous material can be sterilized by exposing the fibrous material to radiation, such as infrared radiation, ultraviolet radiation, or an ionizing radiation, such as gamma radiation. The microorganisms can also be killed using chemical sterilants, such as bleach (e.g., sodium hypochlorite), chlorhexidine, or ethylene oxide.

One method to hydrolyze the sheared and steam exploded fibrous material is by the use of cellulases. Cellulases are a group of enzymes that act synergistically to hydrolyze cellulose. Commercially available Accellerase® 1000 enzyme complex, which contains a complex of enzymes that reduces lignocellulosic biomass into fermentable sugars, can also be used.

According to current understanding, the components of cellulase include endoglucanases, exoglucanases (cellobiohydrolases), and b-glucosidases (cellobiases). Synergism between the cellulase components exists when hydrolysis by a combination of two or more components exceeds the sum of the activities expressed by the individual components. The generally accepted mechanism of action of a cellulase system (particularly of *T. longibrachiatum*) on crystalline cellulose is that endoglucanase hydrolyzes internal β-1,4-glycosidic bonds of the amorphous regions, thereby increasing the number of exposed non-reducing ends. Exoglucanases then cleave off cellobiose units from the non-reducing ends, which in turn are hydrolyzed to individual glucose units by b-glucosidases. There are several configurations of both endo- and exo-glucanases differing in stereospecificities. In general, the synergistic action of the components in various configurations is required for optimum cellulose hydrolysis. Cellulases, however, are more inclined to hydrolyze the amorphous regions of cellulose. A linear relationship between crystallinity and hydrolysis rates exists whereby higher crystallinity indices correspond to slower enzyme hydrolysis rates. Amorphous regions of cellulose hydrolyze at twice the rate of crystalline regions. The hydrolysis of the sheared and steam exploded fibrous material may be performed by any hydrolyzing biomass process.

Steam explosion of biomass sometimes causes the formation of by-products, e.g., toxicants, that are inhibitory to microbial and enzymatic activities. The process of converting the sheared and steam exploded fibrous material into a fuel can therefore optionally include an overliming step prior to fermentation to precipitate some of the toxicants. For example, the pH of the sheared and steam exploded fibrous material may be raised to exceed the pH of 10 by adding calcium hydroxide ($Ca(OH)_2$) followed by a step of lowering the pH to about 5 by adding $H_2SO_4$. The overlimed fibrous material may then be used as is without the removal of precipitates. As shown in FIG. 23, the optional overliming step occurs just prior to the step of hydrolysis of the sheared and steam exploded fibrous material, but it is also contemplated to perform the overliming step after the hydrolysis step and prior to the fermenting step.

Figure 24:
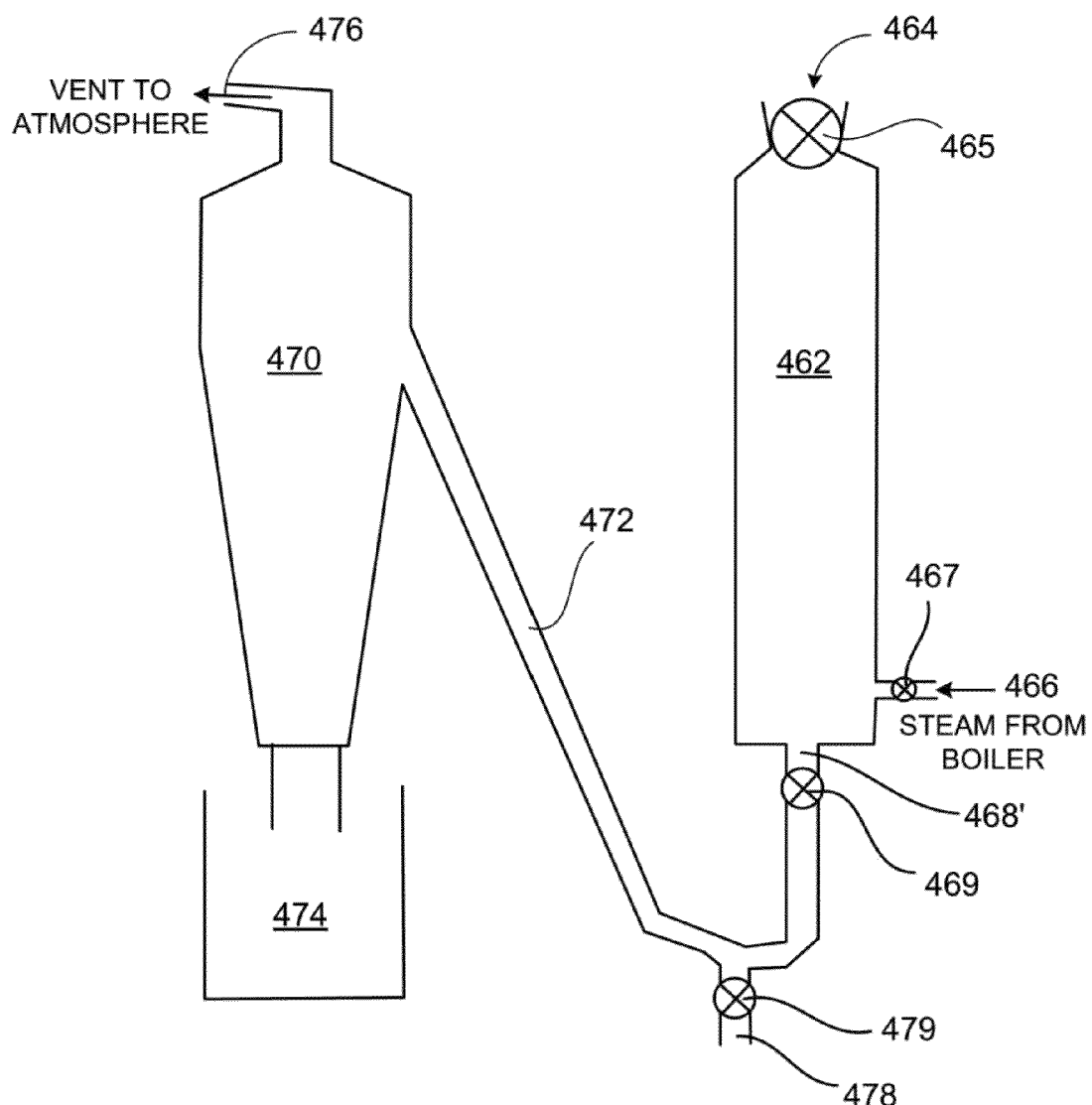
FIG. 24 is a cross-sectional view of a steam explosion apparatus.

FIG. 24 depicts an example of a steam explosion apparatus 460. The steam explosion apparatus 460 includes a reaction chamber 462, in which the fiber source and/or the fibrous material is placed through a fiber source inlet 464. The reaction chamber is sealed by closing fiber source inlet valve 465. The reaction chamber further includes a pressurized steam inlet 466 that includes a steam valve 467. The reaction chamber further includes an explosive depressurization outlet 468 that includes an outlet valve 469 in communication with the cyclone 470 through the connecting pipe 472. Once the reaction chamber contains the fiber source and/or sheared fiber source and is sealed by closing valves 465, 467 and 469, steam is delivered into the reaction chamber 462 by opening the steam inlet valve 467 allowing steam to travel through steam inlet 466. Once the reaction chamber reaches target temperature, which can take about 20-60 seconds, the holding time begins. The reaction chamber is held at the target temperature for the desired holding time, which typically lasts from about 10 seconds to 5 minutes. At the end of the holding time period, outlet valve is opened to allow for explosive depressurization to occur. The process of explosive depressurization propels the contents of the reaction chamber 462 out of the explosive depressurization outlet 468, through the connecting pipe 472, and into the cyclone 470. The steam exploded fiber source or fibrous material then exits the cyclone in a sludge form into the collection bin 474 as much of the remaining steam exits the cyclone into the atmosphere through vent 476. The steam explosion apparatus further includes wash outlet 478 with wash outlet valve 479 in communication with connecting pipe 472. The wash outlet valve 479 is closed during the use of the steam explosion apparatus 460 for steam explosion, but opened during the washing of the reaction chamber 462.

The target temperature of the reaction chamber 462 is preferably between 180 and 240 degrees Celsius or between 200 and 220 degrees Celsius. The holding time is preferably between 10 seconds and 30 minutes, or between 30 seconds and 10 minutes, or between 1 minute and 5 minutes.

Because the steam explosion process results in a sludge of steam exploded fibrous material, the steam exploded fibrous material may optionally include a fiber recovery process where the "liquor" is separated from the steam exploded fibrous material. This fiber recovery step is helpful in that it enables further shearing and/or screening processes and can allow for the conversion of the fibrous material into fuel. The fiber recovery process occurs through the use of a mesh cloth to separate the fibers from the liquor. Further drying processes can also be included to prepare the fibrous material or steam exploded fiber source for subsequent processing.

Combined Irradiating, Pyrolyzing, Sonicating, and/or Oxidizing Devices

In some embodiments, it may be advantageous to combine two or more separate irradiation, sonication, pyrolization, and/or oxidation devices into a single hybrid machine. Using such a hybrid machine, multiple processes may be performed in close juxtaposition or even simultaneously, with the benefit of increasing pretreatment throughput and potential cost savings.

For example, consider the electron beam irradiation and sonication processes. Each separate process is effective in lowering the mean molecular weight of cellulosic material by an order of magnitude or more, and by several orders of magnitude when performed serially.

Figure 25:
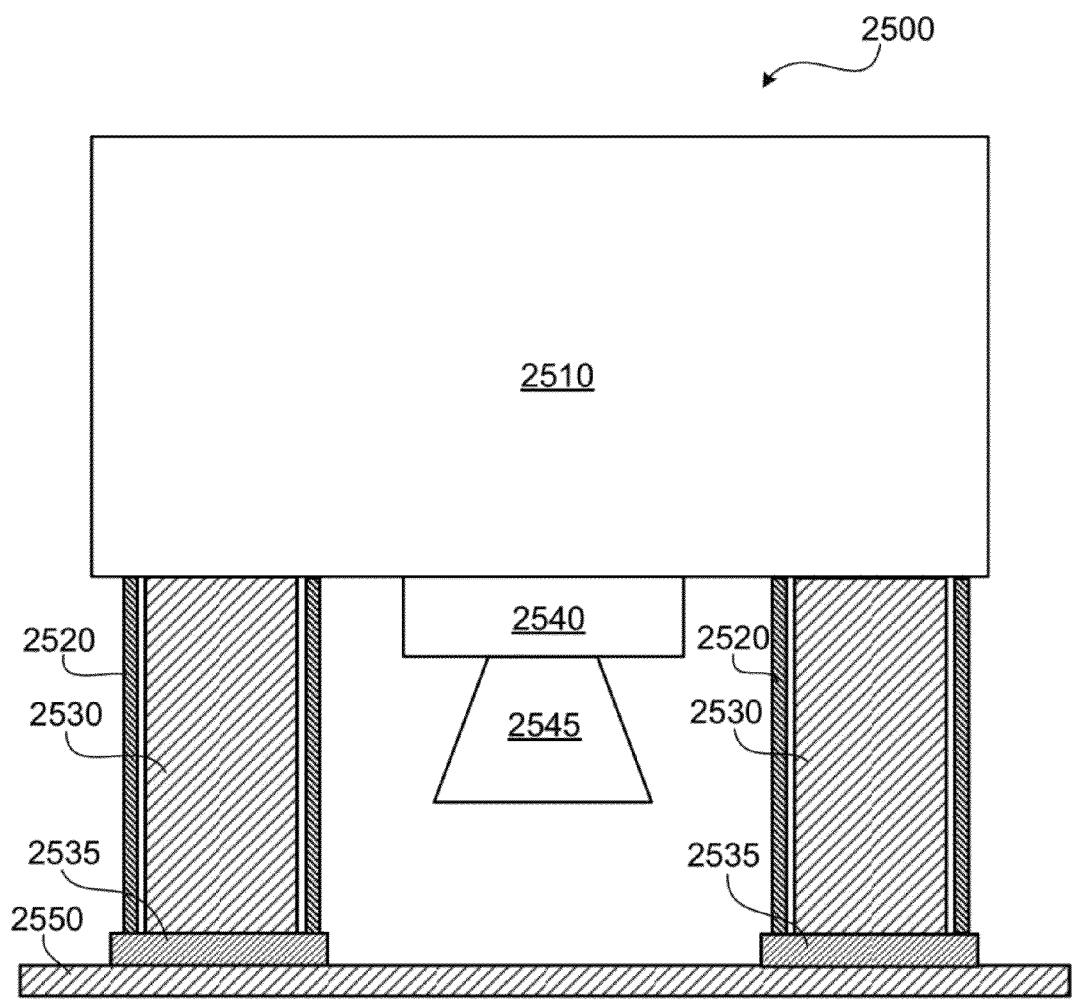
FIG. 25 is a schematic cross-sectional side view of a hybrid electron beam/sonication device.

Both irradiation and sonication processes can be applied using a hybrid electron beam/sonication device as is illustrated in FIG. 25. Hybrid electron beam/sonication device 2500 is pictured above a shallow pool (depth ~3-5 cm) of a slurry of cellulosic material 2550 dispersed in an aqueous, oxidant medium, such as hydrogen peroxide or carbamide peroxide. Hybrid device 2500 has an energy source 2510, which powers both electron beam emitter 2540 and sonication horns 2530.

Electron beam emitter 2540 generates electron beams, which pass through an electron beam aiming device 2545 to impact the slurry 2550 containing cellulosic material. The electron beam aiming device can be a scanner that sweeps a beam over a range of up to about 6 feet in a direction approximately parallel to the surface of the slurry 2550.

On either side of the electron beam emitter 2540 are sonication horns 2530, which deliver ultrasonic wave energy to the slurry 2550. The sonication horns 2530 end in a detachable endpiece 2535 that is in contact with the slurry 2550.

The sonication horns 2530 are at risk of damage from long-term residual exposure to the electron beam radiation. Thus, the horns can be protected with a standard shield 2520, e.g., made of lead or a heavy-metal-containing alloy such as Lipowitz metal, which is impervious to electron beam radiation. Precautions must be taken, however, to ensure that the ultrasonic energy is not affected by the presence of the shield. The detachable endpieces 2535, which are constructed of the same material and attached to the horns 2530, are in contact with the cellulosic material 2550 during processing and are expected to be damaged. Accordingly, the detachable endpieces 2535 are constructed to be easily replaceable.

A further benefit of such a simultaneous electron beam and ultrasound process is that the two processes have complementary results. With electron beam irradiation alone, an insufficient dose may result in cross-linking of some of the polymers in the cellulosic material, which lowers the efficiency of the overall depolymerization process. Lower doses of electron beam irradiation and/or ultrasound radiation may also be used to achieve a similar degree of depolymerization as that achieved using electron beam irradiation and sonication separately. An electron beam device can also be combined with one or more of high frequency, rotor-stator devices, which can be used as an alternative to ultrasonic sonication devices.

Further combinations of devices are also possible. For example, an ionizing radiation device that produces gamma radiation emitted from, e.g., $^{60}$Co pellets, can be combined with an electron beam source and/or an ultrasonic wave source. Shielding requirements may be more stringent in this case.

The radiation devices for pretreating biomass discussed above can also be combined with one or more devices that perform one or more pyrolysis processing sequences. Such a combination may again have the advantage of higher throughput. Nevertheless, caution must be observed, as there may be conflicting requirements between some radiation processes and pyrolysis. For example, ultrasonic radiation devices may require the feedstock be immersed in a liquid oxidizing medium. On the other hand, as discussed previously, it may be advantageous for a sample of feedstock undergoing pyrolysis to be of a particular moisture content. In this case, the new systems automatically measure and monitor for a particular moisture content and regulate the same. Further, some or all of the above devices, especially the pyrolysis device, can be combined with an oxidation device as discussed previously.

Primary Processes
Fermentation

Generally, various microorganisms can produce a number of useful products, such as a fuel, by operating on, e.g., fermenting the pretreated biomass materials. For example, alcohols, organic acids, hydrocarbons, hydrogen, proteins or mixtures of any of these materials can be produced by fermentation or other processes.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

To aid in the breakdown of the materials that include the cellulose, one or more enzymes, e.g., a cellulolytic enzyme can be utilized. In some embodiments, the materials that include the cellulose are first treated with the enzyme, e.g., by combining the material and the enzyme in an aqueous solution. This material can then be combined with the microorganism. In other embodiments, the materials that include the cellulose, the one or more enzymes and the microorganism are combined at the concurrently, e.g., by combining in an aqueous solution.

Also, to aid in the breakdown of the materials that include the cellulose, the materials can be treated post irradiation with heat, a chemical (e.g., mineral acid, base or a strong oxidizer such as sodium hypochlorite), and/or an enzyme.

During the fermentation, sugars released from cellulolytic hydrolysis or the saccharification step, are fermented to, e.g., ethanol, by a fermenting microorganism such as yeast. Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Saccharomyces* spp. e.g., *Saccharomyces cerevisiae* (baker's yeast), *Saccharomyces distaticus*, *Saccharomyces uvarum*; the genus *Kluyveromyces*, e.g., species *Kluyveromyces marxianus*, *Kluyveromyces fragilis*; the genus *Candida*, e.g., *Candida pseudotropicalis*, and *Candida brassicae*, *Pichia stipitis* (a relative of *Candida shehatae*, the genus *Clavispora*, e.g., species *Clavispora lusitaniae* and *Clavispora opuntiae* the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212). In particular embodiments, such as when xylose is present, *Pichia stipitis* (ATCC 66278) is utilized in fermentation.

Commercially available yeast include, for example, Red Star®/Lesaffre Ethanol Red (available from Red Star/Lesaffre, USA) FALI® (available from Fleischmann's Yeast, a division of Burns Philip Food Inc., USA), SUPERSTART® (available from Alltech, now Lallemand), GERT STRAND® (available from Gert Strand AB, Sweden) and FERMOL® (available from DSM Specialties).

Bacteria that can ferment biomass to ethanol and other products include, e.g., *Zymomonas mobilis* and *Clostridium thermocellum* (Philippidis, 1996, supra). Leschine et al. (*International Journal of Systematic and Evolutionary Microbiology* 2002, 52, 1155-1160) isolated an anaerobic, mesophilic, cellulolytic bacterium from forest soil, *Clostridium phytofermentans* sp. nov., which converts cellulose to ethanol.

Fermentation of biomass to ethanol and other products may be carried out using certain types of thermophilic or genetically engineered microorganisms, such *Thermoanaerobacter* species, including *T. mathranii*, and yeast species such as *Pichia* species. An example of a strain of *T. mathranii* is A3M4 described in Sonne-Hansen et al. (*Applied Microbiology and Biotechnology* 1993, 38, 537-541) or Ahring et al. (*Arch. Microbiol.* 1997, 168, 114-119). Other genetically engineered microorganisms are discussed in U.S. Pat. No. 7,192,772.

Yeast and *Zymomonas* bacteria can be used for fermentation or conversion. The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

Enzymes which break down biomass, such as cellulose, to lower molecular weight carbohydrate-containing materials, such as glucose, during saccharification are referred to as cellulolytic enzymes or cellulase. These enzymes may be a complex of enzymes that act synergistically to degrade crystalline cellulose. Examples of cellulolytic enzymes include: endoglucanases, cellobiohydrolases, and cellobiases (β-glucosidases). A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble β-1,4-linked dimer of glucose. Finally cellobiase cleaves cellobiose to yield glucose.

A cellulase is capable of degrading biomass and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei,* and *Trichoderma koningii*), alkalophilic *Bacillus* (see, for example, U.S. Pat. No. 3,844,890 and EP 458162), and *Streptomyces* (see, e.g., EP 458162) may be used. The bacterium, *Saccharophagus degradans*, produces a mixture of enzymes capable of degrading a range of cellulosic materials and may also be used in this process.

Anaerobic cellulolytic bacteria have also been isolated from soil, e.g., a novel cellulolytic species of Clostiridium, *Clostridium phytofermentans* sp. nov. (see Leschine et. al, *International Journal of Systematic and Evolutionary Microbiology* (2002), 52, 1155-1160).

Cellulolytic enzymes using recombinant technology can also be used (see, e.g., WO 2007/071818 and WO 2006/110891).

Other enzyme and enzyme formulations that can be used are discussed in U.S. Publication Nos. 2006/0008885 and 2006/0068475, and in PCT Application No. WO 2006/128304.

The cellulolytic enzymes used can be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA 1991). Suitable media are available from commercial suppliers or may be prepared according to published compositions (e.g., in catalogues of the American Type Culture Collection). Temperature ranges and other conditions suitable for growth and cellulase production are known in the art (see, e.g., Bailey, J. E., and Ollis, D. F., *Biochemical Engineering Fundamentals*, McGraw-Hill Book Company, NY, 1986).

Treatment of cellulose with cellulase is usually carried out at temperatures between 30° C. and 65° C. Cellulases are active over a range of pH of about 3 to 7. A saccharification step may last up to 120 hours. The cellulase enzyme dosage achieves a sufficiently high level of cellulose conversion. For example, an appropriate cellulase dosage is typically between 5.0 and 50 Filter Paper Units (FPU or IU) per gram of cellulose. The FPU is a standard measurement and is defined and measured according to Ghose (1987, Pure and Appl. Chem. 59:257-268).

In particular embodiments, ACCELERASE® 1000 enzyme complex (Genencor) is utilized as the enzyme system at a loading of 0.25 mL per gram of substrate. ACCELERASE® 1000 enzyme complex is a multiple enzyme cocktail with multiple activities, mainly exoglucanase, endoglucanase, hemicellulase and beta-glucosidase. The cocktail has a minimum endoglucanase activity of 2500 CMC U/g and a minimum beta-glucosidase activity of 400 pNPG U/g. The pH of the cocktail is from about 4.8 to about 5.2. In other particular embodiments, the enzyme system utilized is a blend of CELLUCLAST® 1.5 L and Novozyme 188. For example, 0.5 mL of CELLUCLAST® 1.5 L and 0.1 mL of Novozyme 188 can be used for each gram of substrate. When a higher hemicellulase (xylanase) activity is desired, OPTIMASH™ BG can be utilized.

Mobile fermentors can be utilized, as described in U.S. Provisional Patent Application Ser. 60/832,735, now Published International Application No. WO 2008/011598.

Ethanol Fermentation

Ethanol is a product of fermentation. Fermentation is a sequence of reactions which release energy from organic molecules in the absence of oxygen. In this application of fermentation, energy is obtained when sugar is changed to ethanol and carbon dioxide. All beverage ethanol, and more than half of industrial ethanol, is made by this process. Changing corn to ethanol by fermentation takes many steps. Starch in corn must be broken down into simple sugars before fermentation can occur. This can be achieved, for example, by cooking the corn and adding the enzymes alpha amylase and gluco amylase. These enzymes function as catalysts to speed up the chemical changes. Once a simple sugar is obtained, yeast is added. Yeast is a single-celled fungus, which feeds on the sugar and causes the fermentation. As the fungi feeds on the sugar, it produces alcohol (ethanol) and carbon dioxide. In fermentation, the ethanol retains much of the energy that was originally in the sugar, which explains why ethanol is an excellent fuel.

The fermentation reaction is represented by the simple equation:

$$C_6H_{12}O_6 \rightarrow 2CH_3CH_2OH + 2CO_2$$

Ethanol can be made from a wide variety of available feedstocks. Fuel ethanol can be made from crops which contain starch such as feed grains, food grains, such as corn, and tubers, such as potatoes and sweet potatoes. Crops containing sugar, such as sugar beets, sugarcane, and sweet sorghum also could be used for the production of ethanol. In addition, food processing byproducts, such as molasses, cheese whey, and cellulosic materials including grass and wood, as well as agricultural and forestry residues, can be processed to ethanol. As discussed above, these and other feedstocks can be treated as discussed herein to facilitate production of ethanol.

Conversion of Starchy Materials

FIGS. 26 and 27 show block diagrams for a dry and wet milling process, respectively, and illustrate the conversion, e.g., fermentation, of corn kernels to ethanol and other valuable co-products.

Referring particularly now to FIG. 26, in some implementations, a dry milling process for the conversion of corn kernels to ethanol, e.g., anhydrous ethanol, that can be utilized as a fuel, e.g., automobile or aviation fuel, can begin with pre-treating the dried corn kernels with any one or more pretreatments described herein, such as radiation, e.g., any one or more types of radiation described herein (e.g., a beam of electrons in which each electron has an energy of about 5 MeV or a beam of protons in which the energy of each proton is about 3-100 MeV). After pre-treatment, the corn kernels can be ground and/or sheared into a powder. Although any one or more pretreatments described herein can be applied after grinding and/or at any time during the dry milling process outlined in FIG. 26, pretreating prior to grinding and/or shearing can be advantageous in that the kernels are generally more brittle after pretreatment and, as a result, are easier and can require less energy to grind and/or shear. In some embodiments, a selected pretreatment can be applied more than once during conversion, e.g., prior to milling and then after milling.

After grinding and/or shearing, the milled, dry kernels can be optionally hydrated by adding the milled material to a vessel containing water and, optionally, hydrating agents, such as surfactants. Optionally, this reaction vessel can also include one or more enzymes, such as amylase, to aid in further breakdown of starchy biomass, or the reaction vessel may contain one or more acids, such as a mineral acid, e.g., dilute sulfuric acid. If a hydration vessel is utilized, its contents are emptied into a conversion vessel, e.g., a fermentation vessel, which includes one or more conversion microbes, such as one or more yeasts, bacteria or mixtures of yeasts and/or bacteria. If a hydration vessel is not utilized, the milled material can be directly charged to the conversion vessel, e.g., for fermentation.

After conversion, the remaining solids are removed and dried to give distillers dry grains (DDG), while the ethanol is distilled off. In some embodiments, a thermophilic microbe is utilized for the conversion and the ethanol is continuously removed by evaporation as it is produced. If desired, the distilled ethanol can be fully dehydrated, such as by passing the wet ethanol through a zeolite bed, or distilling with benzene.

Referring particularly now to FIG. 27, in some implementations, the wet milling process for the conversion of corn kernels to anhydrous ethanol begins with pretreating the dried corn kernels with any one or more pretreatments described herein, such as radiation, e.g., any one or more types of radiation described herein (e.g., a beam of electrons in which each electron has an energy of about 5 MeV). After pretreatment, the corn kernels are steeped in dilute sulfuric acid and gently stirred to break the corn kernels into its constituents. After steeping, the fiber, oil and germ portions are fractionated and dried, and then combined with any solids remaining after distillation to give corn gluten feed (CGF). After removing germ and fiber, in some embodiments, the gluten is separated to give corn gluten meal (CGM). The remaining starch can be pretreated again (or for the first time) by any pretreatment described herein, e.g., to reduce its molecular weight and/or to functionalize the starch so that it is more soluble. In some embodiments, the starch is then charged to a reaction vessel containing water and, optionally, hydrating agents, such as surfactants. Optionally, this reaction vessel can also include one or more enzymes, such as amylase, to aid in further breakdown of starch, or the reaction vessel may contain one or more acids, such as a mineral acid, e.g., dilute sulfuric acid. As shown, saccharification can occur in several vessels and then the contents of the final vessel can be emptied into a conversion vessel, e.g., a fermentation vessel, which includes one or more conversion microbes, such as one or more yeasts or bacteria.

After conversion, the ethanol is distilled off. In some embodiments, a thermophilic microbe is utilized for the conversion and the ethanol is continuously removed by evaporation as it is produced. If desired, the distilled ethanol can be fully dehydrated, such as by passing the wet ethanol through a zeolite bed.

Gasification

In addition to using pyrolysis for pre-treatment of feedstock, pyrolysis can also be used to process pre-treated feedstock to extract useful materials. In particular, a form of pyrolysis known as gasification can be employed to generate fuel gases along with various other gaseous, liquid, and solid products. To perform gasification, the pre-treated feedstock is introduced into a pyrolysis chamber and heated to a high temperature, typically 700° C. or more. The temperature used depends upon a number of factors, including the nature of the feedstock and the desired products.

Quantities of oxygen (e.g., as pure oxygen gas and/or as air) and steam (e.g., superheated steam) are also added to the pyrolysis chamber to facilitate gasification. These compounds react with carbon-containing feedstock material in a multiple-step reaction to generate a gas mixture called synthesis gas (or "syngas"). Essentially, during gasification, a limited amount of oxygen is introduced into the pyrolysis chamber to allow some feedstock material to combust to form carbon monoxide and generate process heat. The process heat can then be used to promote a second reaction that converts additional feedstock material to hydrogen and carbon monoxide.

In a first step of the overall reaction, heating the feedstock material produces a char that can include a wide variety of different hydrocarbon-based species. Certain volatile materials can be produced (e.g., certain gaseous hydrocarbon materials), resulting in a reduction of the overall weight of the feedstock material. Then, in a second step of the reaction, some of the volatile material that is produced in the first step reacts with oxygen in a combustion reaction to produce both carbon monoxide and carbon dioxide. The combustion reaction releases heat, which promotes the third step of the reaction. In the third step, carbon dioxide and steam (e.g., water) react with the char generated in the first step to form carbon monoxide and hydrogen gas. Carbon monoxide can also react with steam, in a water gas shift reaction, to form carbon dioxide and further hydrogen gas.

Gasification can be used as a primary process to generate products directly from pre-treated feedstock for subsequent transport and/or sale, for example. Alternatively, or in addition, gasification can be used as an auxiliary process for generating fuel for an overall processing system. The hydrogen-rich syngas that is generated via the gasification process can be burned, for example, to generate electricity and/or process heat that can be directed for use at other locations in the processing system. As a result, the overall processing system can be at least partially self-sustaining A number of other products, including pyrolysis oils and gaseous hydrocarbon-based substances, can also be obtained during and/or following gasification; these can be separated and stored or transported as desired.

A variety of different pyrolysis chambers are suitable for gasification of pre-treated feedstock, including the pyrolysis chambers disclosed herein. In particular, fluidized bed reactor systems, in which the pre-treated feedstock is fluidized in steam and oxygen/air, provide relatively high throughput and straightforward recovery of products. Solid char that remains following gasification in a fluidized bed system (or in other pyrolysis chambers) can be burned to generate additional process heat to promote subsequent gasification reactions.

Syngas can be reformed using a Fischer-Tropsch process, which is a catalyzed chemical reaction in which the synthesis gas is converted into liquid alcohols and hydrocarbons. The most common catalysts are based on iron and cobalt, although nickel and ruthenium have also been used.

In an alternative process, a biofilm can be used to reform the syngas to produce the liquid fuel instead of a chemical catalyst. Such a process has been described by Coskata, Inc. Any of the biomass materials described herein can be used in Coskata's process.

In some embodiments, irradiating the biomass material, e.g., with a beam of particles, such as electrons, prior to gasification can lower the gasification temperature, resulting in less energy being consumed during gasification, and can result in less char and tar formation, resulting in enhanced syngas yield.

Post-Processing

Distillation

After fermentation, the resulting fluids can be distilled using, for example, a "beer column" to separate ethanol and other alcohols from the majority of water and residual solids. The vapor exiting the beer column can be, e.g., 35% by weight ethanol, and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Waste Water Treatment

Wastewater treatment is used to minimize makeup water requirements of the plant by treating process water for reuse within the plant. Wastewater treatment can also produce fuel (e.g., sludge and biogas) that can be used to improve the overall efficiency of the ethanol production process. For example, as described in further detail below, sludge and biogas can be used to create steam and electricity that can be used in various plant processes.

Wastewater is initially pumped through a screen (e.g., a bar screen) to remove large particles, which are collected in a hopper. In some embodiments, the large particles are sent to a landfill. Additionally or alternatively, the large particles are burned to create steam and/or electricity as described in further detail below. In general, the spacing on the bar screen is between ¼ inch to 1 inch spacing (e.g., ½ inch spacing).

The wastewater then flows to an equalization tank, where the organic concentration of the wastewater is equalized during a retention time. In general, the retention time is between 8 hours and 36 hours (e.g., 24 hours). A mixer is disposed within the tank to stir the contents of the tank. In some embodiments, mixers disposed throughout the tank are used to stir the contents of the tank. In certain embodiments, the mixer substantially mixes the contents of the equalization tank such that conditions (e.g., wastewater concentration and temperature) throughout the tank are uniform.

A first pump moves water from the equalization tank through a liquid-to-liquid heat exchanger. The heat exchanger is controlled (e.g., by controlling the flow rate of fluid through the heat exchanger) such that wastewater exiting the heat exchanger is at a desired temperature for anaerobic treatment. For example, the desired temperature for anaerobic treatment can be between 40° C. to 60° C.

After exiting the heat exchanger, the wastewater enters one or more anaerobic reactors. In some embodiments, the concentration of sludge in each anaerobic reactor is the same as the overall concentration of sludge in the wastewater. In other embodiments, the anaerobic reactor has a higher concentration of sludge than the overall concentration of sludge in the wastewater.

A nutrient solution containing nitrogen and phosphorus is metered into each anaerobic reactor containing wastewater. The nutrient solution reacts with the sludge in the anaerobic reactor to produce biogas which can contain 50% methane and have a heating value of approximately 12,000 British thermal units, or Btu, per pound). The biogas exits each anaerobic reactor through a vent and flows into a manifold, where several biogas streams are combined into a single stream. A compressor moves the stream of biogas to a boiler or a combustion engine as described in further detail below. In some embodiments, the compressor also moves the single stream of biogas through a desulphurization catalyst. Additionally or alternatively, the compressor can move the single stream of biogas through a sediment trap.

A second pump moves anaerobic effluent from the anaerobic reactors to one or more aerobic reactors (e.g., activated sludge reactors). An aerator is disposed within each aerobic reactor to mix the anaerobic effluent, sludge, and oxygen (e.g., oxygen contained in air). Within each aerobic reactor, oxidation of cellular material in the anaerobic effluent produces carbon dioxide, water, and ammonia.

Aerobic effluent moves (e.g., via gravity) to a separator, where sludge is separated from treated water. Some of the sludge is returned to the one or more aerobic reactors to create an elevated sludge concentration in the aerobic reactors, thereby facilitating the aerobic breakdown of cellular material in the wastewater. A conveyor removes excess sludge from the separator. As described in further detail below, the excess sludge is used as fuel to create steam and/or electricity.

The treated water is pumped from the separator to a settling tank. Solids dispersed throughout the treated water settle to the bottom of the settling tank and are subsequently removed. After a settling period, treated water is pumped from the settling tank through a fine filter to remove any additional solids remaining in the water. In some embodiments, chlorine is added to the treated water to kill pathogenic bacteria. In some embodiments, one or more physical-chemical separation techniques are used to further purify the treated water. For example, treated water can be pumped through a carbon adsorption reactor. As another example, treated water can pumped through a reverse osmosis reactor.

In the processes disclosed herein, whenever water is used in any process, it may be grey water, e.g., municipal grey water, or black water. In some embodiments, the grey or black water is sterilized prior to use. Sterilization may be accomplished by any desired technique, for example, by irradiation, steam, or chemical sterilization.

Waste Combustion

The production of alcohol from biomass can result in the production of various by-product streams useful for generating steam and electricity to be used in other parts of the plant. For example, steam generated from burning by-product streams can be used in the distillation process. As another example, electricity generated from burning by-product streams can be used to power electron beam generators and ultrasonic transducers used in pretreatment.

The by-products used to generate steam and electricity are derived from a number of sources throughout the process. For example, anaerobic digestion of wastewater produces a biogas high in methane and a small amount of waste biomass (sludge). As another example, post-distillate solids (e.g., unconverted lignin, cellulose, and hemicellulose remaining from the pretreatment and primary processes) can be used as a fuel.

The biogas is diverted to a combustion engine connected to an electric generator to produce electricity. For example, the biogas can be used as a fuel source for a spark-ignited natural gas engine. As another example, the biogas can be used as a fuel source for a direct-injection natural gas engine. As another example, the biogas can be used as a fuel source for a combustion turbine. Additionally or alternatively, the combustion engine can be configured in a cogeneration configuration. For example, waste heat from the combustion engines can be used to provide hot water or steam throughout the plant.

The sludge, and post-distillate solids are burned to heat water flowing through a heat exchanger. In some embodiments, the water flowing through the heat exchanger is evaporated and superheated to steam. In certain embodiments, the steam is used in the pretreatment rector and in heat exchange in the distillation and evaporation processes. Additionally or alternatively, the steam expands to power a multi-stage steam turbine connected to an electric generator. Steam exiting the steam turbine is condensed with cooling water and returned to the heat exchanger for reheating to steam. In some embodiments, the flow rate of water through the heat exchanger is controlled to obtain a target electricity output from the steam turbine connected to an electric generator. For example, water can be added to the heat exchanger to ensure that the steam turbine is operating above a threshold condition (e.g., the turbine is spinning fast enough to turn the electric generator).

While certain embodiments have been described, other embodiments are possible.

As an example, while the biogas is described as being diverted to a combustion engine connected to an electric generator, in certain embodiments, the biogas can be passed through a fuel reformer to produce hydrogen. The hydrogen is then converted to electricity through a fuel cell.

As another example, while the biogas is described as being burned apart from the sludge and post-distillate solids, in certain embodiments, all of the waste by-products can be burned together to produce steam.

Products/Co-Products
Alcohols

The alcohol produced can be a monohydroxy alcohol, e.g., ethanol, or a polyhydroxy alcohol, e.g., ethylene glycol or glycerin. Examples of alcohols that can be produced include methanol, ethanol, propanol, isopropanol, butanol, e.g., n-, sec- or t-butanol, ethylene glycol, propylene glycol, 1,4-butane diol, glycerin or mixtures of these alcohols.

Each of the alcohols produced by the plant have commercial value as industrial feedstock. For example, ethanol can be used in the manufacture of varnishes and perfume. As another example, methanol can be used as a solvent used as a component in windshield wiper fluid. As still another example, butanol can be used in plasticizers, resins, lacquers, and brake fluids.

Bioethanol produced by the plant is valuable as an ingredient used in the food and beverage industry. For example, the ethanol produced by the plant can be purified to food grade alcohol and used as a primary ingredient in the alcoholic beverages.

Bioethanol produced by the plant also has commercial value as a transportation fuel. The use of ethanol as a transportation fuel can be implemented with relatively little capital investment from spark ignition engine manufacturers and owners (e.g., changes to injection timing, fuel-to-air ratio, and components of the fuel injection system). Many automotive manufacturers currently offer flex-fuel vehicles capable of operation on ethanol/gasoline blends up to 85% ethanol by volume (e.g., standard equipment on a Chevy Tahoe 4×4).

Bioethanol produced by this plant can be used as an engine fuel to improve environmental and economic conditions beyond the location of the plant. For example, ethanol produced by this plant and used as a fuel can reduce greenhouse gas emissions from manmade sources (e.g., transportation sources). As another example, ethanol produced by this plant and used as an engine fuel can also displace consumption of gasoline refined from oil.

Bioethanol has a greater octane number than conventional gasoline and, thus, can be used to improve the performance (e.g., allow for higher compression ratios) of spark ignition engines. For example, small amounts (e.g., 10% by volume) of ethanol can be blended with gasoline to act as an octane enhancer for fuels used in spark ignition engines. As another example, larger amounts (e.g., 85% by volume) of ethanol can be blended with gasoline to further increase the fuel octane number and displace larger volumes of gasoline.

Bioethanol strategies are discussed, e.g., by DiPardo in *Journal of Outlook for Biomass Ethanol Production and Demand* (*EIA Forecasts*), 2002; Sheehan in *Biotechnology Progress*, 15:8179, 1999; Martin in *Enzyme Microbes Technology*, 31:274, 2002; Greer in *BioCycle*, 61-65, April 2005; Lynd in *Microbiology and Molecular Biology Reviews*, 66:3, 506-577, 2002; Ljungdahl et al., in U.S. Pat. No. 4,292,406; and Bellamy, in U.S. Pat. No. 4,094,742.

Organic Acids

The organic acids produced can include monocarboxylic acids or polycarboxylic acids. Examples of organic acids include formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid, γ-hydroxybutyric acid or mixtures of these acids.

Co-Products
Lignin Residue

As described above, lignin-containing residues from primary and pretreatment processes has value as a high/medium energy fuel and can be used to generate power and steam for use in plant processes. However, such lignin residues are a new type of solids fuel and there is little demand for it outside of the plant boundaries, and the costs of drying it for transportation only subtract from its potential value. In some cases, gasification of the lignin residues can convert it to a higher-value product with lower cost.

Other Co-Products

Cell matter, furfural, and acetic acid have been identified as potential co-products of biomass-to-fuel processing facilities. Interstitial cell matter could be valuable, but might require significant purification. Markets for furfural and acetic acid are in place, although it is unlikely that they are large enough to consume the output of a fully commercialized lignocellulose-to-ethanol industry.

EXAMPLES

The following Examples are intended to illustrate, and do not limit the teachings of this disclosure.

Example 1

Preparation of Fibrous Material from Polycoated Paper

A 1500 pound skid of virgin, half-gallon juice cartons made of un-printed polycoated white Kraft board having a bulk density of 20 lb/ft$^3$ was obtained from International Paper. Each carton was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch).

Figure 28:
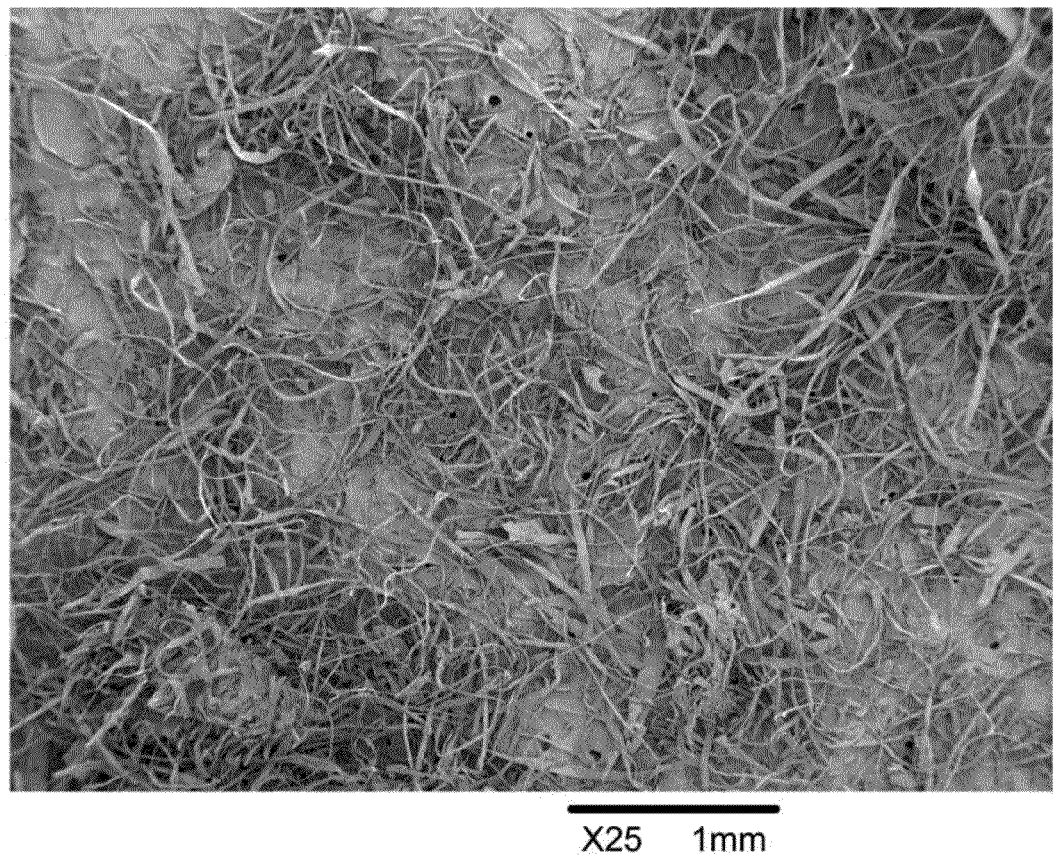
FIG. 28 is a scanning electron micrograph of a fibrous material produced from polycoated paper at 25× magnification. The fibrous material was produced on a rotary knife cutter utilizing a screen with ⅛ inch openings.

The confetti-like material was fed to a Munson rotary knife cutter, Model SC30. Model SC30 is equipped with four rotary blades, four fixed blades, and a discharge screen having ⅛ inch openings. The gap between the rotary and fixed blades was set to approximately 0.020 inch. The rotary knife cutter sheared the confetti-like pieces across the knife-edges, tearing the pieces apart and releasing a fibrous material at a rate of about one pound per hour. The fibrous material had a BET surface area of 0.9748 m$^2$/g+/−0.0167 m$^2$/g, a porosity of 89.0437 percent and a bulk density (@0.53 psia) of 0.1260 g/mL. An average length of the fibers was 1.141 mm and an average width of the fibers was 0.027 mm, giving an average L/D of 42:1. A scanning electron micrograph of the fibrous material is shown in FIG. 28 at 25× magnification.

Example 2

Preparation of Fibrous Material from Bleached Kraft Board

Figure 29:
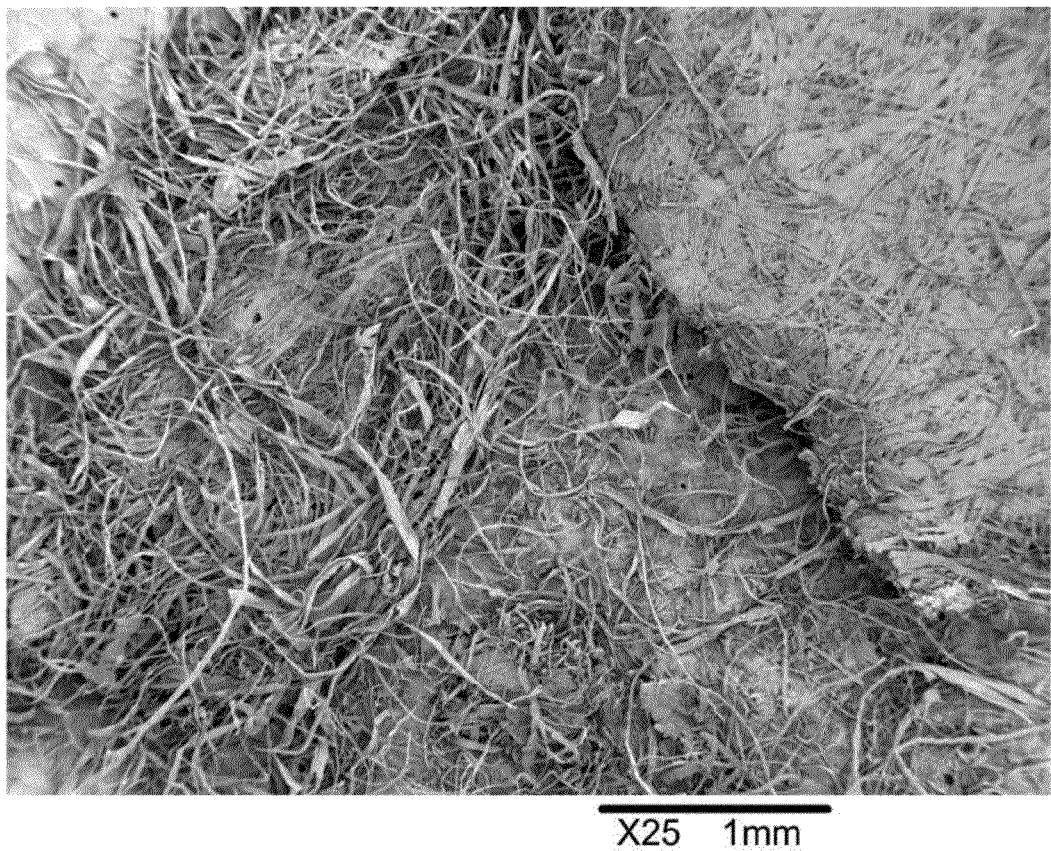
FIG. 29 is a scanning electron micrograph of a fibrous material produced from bleached Kraft board paper at 25× magnification. The fibrous material was produced on a rotary knife cutter utilizing a screen with ⅛ inch openings.

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces, releasing a fibrous material at a rate of about one pound per hour. The fibrous material had a BET surface area of 1.1316 $m^2/g$+/−0.0103 $m^2/g$, a porosity of 88.3285 percent and a bulk density (@0.53 psia) of 0.1497 g/mL. An average length of the fibers was 1.063 mm and an average width of the fibers was 0.0245 mm, giving an average L/D of 43:1. A scanning electron micrograph of the fibrous material is shown in FIG. 29 at 25× magnification.

Example 3

Preparation of Twice Sheared Fibrous Material from Bleached Kraft Board

Figure 30:
FIG. 30 is a scanning electron micrograph of a fibrous material produced from bleached Kraft board paper at 25× magnification. The fibrous material was twice sheared on a rotary knife cutter utilizing a screen with 1/16 inch openings during each shearing.

A 1500 pound skid of virgin bleached white Kraft board having a bulk density of 30 $lb/ft^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had ¹⁄₁₆ inch openings. The gap between the rotary and fixed blades was set to approximately 0.020 inch. The rotary knife cutter the confetti-like pieces, releasing a fibrous material at a rate of about one pound per hour. The material resulting from the first shearing was fed back into the same setup described above and sheared again. The resulting fibrous material had a BET surface area of 1.4408 $m^2/g$+/−0.0156 $m^2/g$, a porosity of 90.8998 percent and a bulk density (@0.53 psia) of 0.1298 g/mL. An average length of the fibers was 0.891 mm and an average width of the fibers was 0.026 mm, giving an average L/D of 34:1. A scanning electron micrograph of the fibrous material is shown in FIG. 30 at 25× magnification.

Example 4

Preparation of Thrice Sheared Fibrous Material from Bleached Kraft Board

Figure 31:
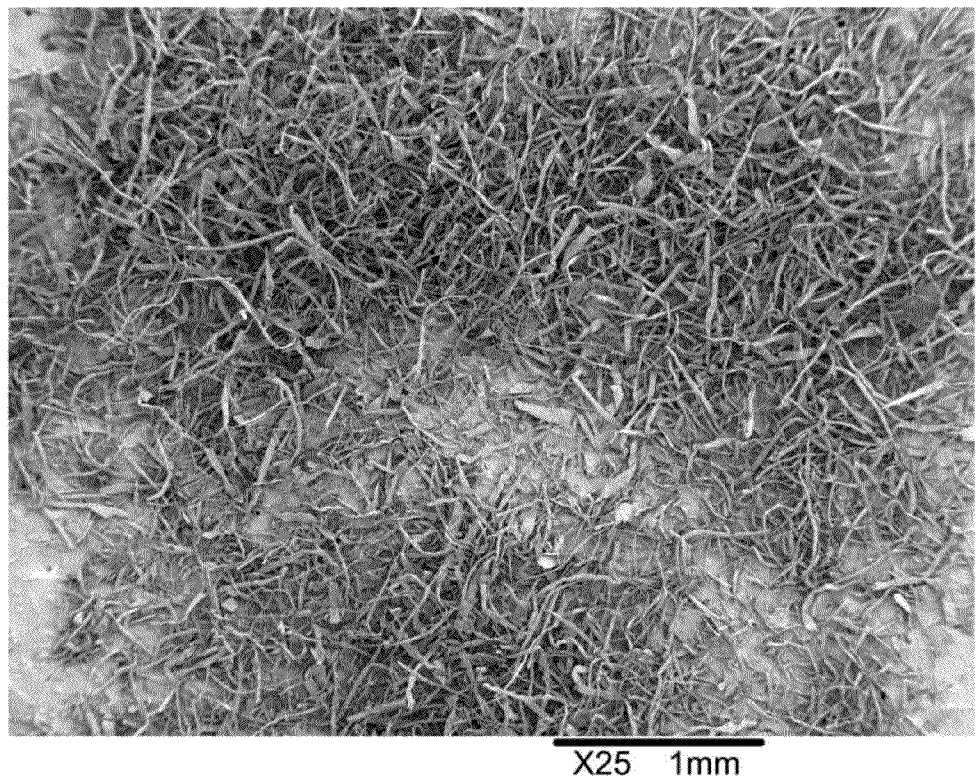
FIG. 31 is a scanning electron micrograph of a fibrous material produced from bleached Kraft board paper at 25× magnification. The fibrous material was thrice sheared on a rotary knife cutter. During the first shearing, a ⅛ inch screen was used; during the second shearing, a 1/16 inch screen was used, and during the third shearing a 1/32 inch screen was used.

A 1500 pound skid of virgin bleached white Kraft board having a bulk density of 30 $lb/ft^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces across the knife-edges. The material resulting from the first shearing was fed back into the same setup and the screen was replaced with a ¹⁄₁₆ inch screen. This material was sheared. The material resulting from the second shearing was fed back into the same setup and the screen was replaced with a ¹⁄₃₂ inch screen. This material was sheared. The resulting fibrous material had a BET surface area of 1.6897 $m^2/g$+/−0.0155 $m^2/g$, a porosity of 87.7163 percent and a bulk density (@0.53 psia) of 0.1448 g/mL. An average length of the fibers was 0.824 mm and an average width of the fibers was 0.0262 mm, giving an average L/D of 32:1. A scanning electron micrograph of the fibrous material is shown in FIG. 31 at 25× magnification.

Example 5

Preparation of Densified Fibrous Material from Bleached Kraft Board without Added Binder Fibrous material was prepared according to Example 2. Approximately 1 lb of water was sprayed onto each 10 lb of fibrous material. The fibrous material was densified using a California Pellet Mill 1100 operating at 75° C. Pellets were obtained having a bulk density ranging from about 7 $lb/ft^3$ to about 15 $lb/ft^3$.

Example 6

Preparation of Densified Fibrous Material from Bleached Kraft Board with Binder

Fibrous material was prepared according to Example 2.
A 2 weight percent stock solution of POLYOX™ WSR N10 (polyethylene oxide) was prepared in water.
Approximately 1 lb of the stock solution was sprayed onto each 10 lb of fibrous material. The fibrous material was densified using a California Pellet Mill 1100 operating at 75° C. Pellets were obtained having a bulk density ranging from about 15 $lb/ft^3$ to about 40 $lb/ft^3$.

Example 7

Reducing the Molecular Weight of Cellulose in Fibrous Kraft Paper by Gamma Radiation with Minimum Oxidation Fibrous material is prepared according to Example 4. The fibrous Kraft paper is densified according to Example 5.
The densified pellets are placed in a glass ampoule having a maximum capacity of 250 mL. The glass ampoule is evacuated under high vacuum ($10^{-5}$ ton) for 30 minutes, and then back-filled with argon gas. The ampoule is sealed under argon. The pellets in the ampoule are irradiated with gamma radiation for about 3 hours at a dose rate of about 1 Mrad per hour to provide an irradiated material in which the cellulose has a lower molecular weight than the fibrous Kraft starting material.

Example 8

Reducing the Molecular Weight of Cellulose in Fibrous Kraft Paper by Gamma Radiation with Maximum Oxidation Fibrous material is prepared according to Example 4. The fibrous Kraft paper is densified according to Example 5.

The densified pellets are placed in a glass ampoule having a maximum capacity of 250 mL. The glass ampoule is sealed under an atmosphere of air. The pellets in the ampoule are irradiated with gamma radiation for about 3 hours at a dose rate of about 1 Mrad per hour to provide an irradiated material in which the cellulose has a lower molecular weight than the fibrous Kraft starting material.

Example 9

Methods of Determining Molecular Weight of Cellulosic and Lignocellulosic Materials by Gel Permeation Chromatography Cellulosic and lignocellulosic materials for analysis were treated according to Example 4. Sample materials presented in the following tables include Kraft paper (P), wheat straw (WS), alfalfa (A), and switchgrass (SG). The number "132" of the Sample ID refers to the particle size of the material after shearing through a 1/32 inch screen. The number after the dash refers to the dosage of radiation (MRad) and "US" refers to ultrasonic treatment. For example, a sample ID "P132-10" refers to Kraft paper that has been sheared to a particle size of 132 mesh and has been irradiated with 10 MRad.

TABLE 1

Peak Average Molecular Weight of Irradiated Kraft Paper

| Sample Source | Sample ID | Dosage[1] (MRad) | Ultrasound[2] | Std Average MW ± Std Dev. |
|---|---|---|---|---|
| Kraft Paper | P132 | 0 | No | 32853 ± 10006 |
| | P132-10 | 10 | " | 61398 ± 2468** |
| | P132-100 | 100 | " | 8444 ± 580 |
| | P132-181 | 181 | " | 6668 ± 77 |
| | P132-US | 0 | Yes | 3095 ± 1013 |

**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

TABLE 2

Peak Average Molecular Weight of Irradiated Materials

| Sample ID | Peak # | Dosage[1] (MRad) | Ultrasound[2] | Average MW ± Std Dev. |
|---|---|---|---|---|
| WS132 | 1 | 0 | No | 1407411 ± 175191 |
| | 2 | " | " | 39145 ± 3425 |
| | 3 | " | " | 2886 ± 177 |
| WS132-10* | 1 | 10 | " | 26040 ± 3240 |
| WS132-100* | 1 | 100 | " | 23620 ± 453 |
| A132 | 1 | 0 | " | 1604886 ± 151701 |
| | 2 | " | " | 37525 ± 3751 |
| | 3 | " | " | 2853 ± 490 |
| A132-10* | 1 | 10 | " | 50853 ± 1665 |
| | 2 | " | " | 2461 ± 17 |
| A132-100* | 1 | 100 | " | 38291 ± 2235 |
| | 2 | " | " | 2487 ± 15 |
| SG132 | 1 | 0 | " | 1557360 ± 83693 |
| | 2 | " | " | 42594 ± 4414 |
| | 3 | " | " | 3268 ± 249 |
| SG132-10* | 1 | 10 | " | 60888 ± 9131 |
| SG132-100* | 1 | 100 | " | 22345 ± 3797 |
| SG132-10-US | 1 | 10 | Yes | 86086 ± 43518 |
| | 2 | " | " | 2247 ± 468 |
| SG132-100-US | 1 | 100 | " | 4696 ± 1465 |

*Peaks coalesce after treatment
**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

Gel Permeation Chromatography (GPC) is used to determine the molecular weight distribution of polymers. During GPC analysis, a solution of the polymer sample is passed through a column packed with a porous gel trapping small molecules. The sample is separated based on molecular size with larger molecules eluting sooner than smaller molecules. The retention time of each component is most often detected by refractive index (RI), evaporative light scattering (ELS), or ultraviolet (UV) and compared to a calibration curve. The resulting data is then used to calculate the molecular weight distribution for the sample.

A distribution of molecular weights rather than a unique molecular weight is used to characterize synthetic polymers. To characterize this distribution, statistical averages are utilized. The most common of these averages are the "number average molecular weight" ($M_n$) and the "weight average molecular weight" ($M_w$). Methods of calculating these values are described in the art, e.g., in Example 9 of WO 2008/073186.

The polydispersity index or PI is defined as the ratio of $M_w/M_n$. The larger the PI, the broader or more disperse the distribution. The lowest value that a PI can be is 1. This represents a monodisperse sample; that is, a polymer with all of the molecules in the distribution being the same molecular weight.

The peak molecular weight value ($M_P$) is another descriptor defined as the mode of the molecular weight distribution. It signifies the molecular weight that is most abundant in the distribution. This value also gives insight to the molecular weight distribution.

Most GPC measurements are made relative to a different polymer standard. The accuracy of the results depends on how closely the characteristics of the polymer being analyzed match those of the standard used. The expected error in reproducibility between different series of determinations, calibrated separately, is ca. 5-10% and is characteristic to the limited precision of GPC determinations. Therefore, GPC results are most useful when a comparison between the molecular weight distributions of different samples is made during the same series of determinations.

The lignocellulosic samples required sample preparation prior to GPC analysis. First, a saturated solution (8.4% by weight) of lithium chloride (LiCl) was prepared in dimethyl acetamide (DMAc). Approximately 100 mg of each sample was added to approximately 10 g of a freshly prepared saturated LiCl/DMAc solution, and each mixture was heated to approximately 150° C.-170° C. with stirring for 1 hour. The resulting solutions were generally light- to dark-yellow in color. The temperature of the solutions was decreased to approximately 100° C. and the solutions were heated for an additional 2 hours. The temperature of the solutions was then decreased to approximately 50° C. and each sample solution was heated for approximately 48 to 60 hours. Of note, samples irradiated at 100 MRad were more easily solubilized as compared to their untreated counterpart. Additionally, the sheared samples (denoted by the number 132) had slightly lower average molecular weights as compared with uncut samples.

The resulting sample solutions were diluted 1:1 using DMAc as solvent and were filtered through a 0.45 μm PTFE filter. The filtered sample solutions were then analyzed by GPC. The peak average molecular weight (Mp) of the samples, as determined by Gel Permeation Chromatography (GPC), are summarized in Tables 1 and 2. Each sample was prepared in duplicate and each preparation of the sample was analyzed in duplicate (two injections) for a total of four injections per sample. The EasiCal polystyrene standards PS1A and PS1B were used to generate a calibration curve for the molecular weight scale from about 580 to 7,500,00 Daltons.

TABLE 3

GPC Analysis Conditions

| | |
|---|---|
| Instrument: | Waters Alliance GPC 2000 |
| | Plgel 10μ Mixed-B |
| Columns (3): | S/N's: 10M-MB-148-83; 10M-MB-148-84; 10M-MB-174-129 |
| Mobile Phase (solvent): | 0.5% LiCl in DMAc (1.0 mL/min) |
| Column/Detector Temperature: | 70 ° C. |
| Injector Temperature: | 70° C. |
| Sample Loop Size: | 323.5 μL |

Example 10

Determining Crystallinity of Irradiated Material by X-Ray Diffraction

X-ray diffraction (XRD) is a method by which a crystalline sample is irradiated with monoenergetic x-rays. The interaction of the lattice structure of the sample with these x-rays is recorded and provides information about the crystalline structure being irradiated. The resulting characteristic "fingerprint" allows for the identification of the crystalline compounds present in the sample. Using a whole-pattern fitting analysis (the Rietvelt Refinement), it is possible to perform quantitative analyses on samples containing more than one crystalline compound.

TABLE 4

XRD Data Including Domain Size and % Crystallinity

| Sample ID | Domain Size (Å) | % Crystallinity |
|---|---|---|
| P132 | 55 | 55 |
| P132-10 | 46 | 58 |
| P132-100 | 50 | 55 |
| P132-181 | 48 | 52 |
| P132-US | 26 | 40 |
| A132 | 28 | 42 |
| A132-10 | 26 | 40 |
| A132-100 | 28 | 35 |
| WS132 | 30 | 36 |
| WS132-10 | 27 | 37 |
| WS132-100 | 30 | 41 |
| SG132 | 29 | 40 |
| SG132-10 | 28 | 38 |
| SG132-100 | 28 | 37 |
| SG132-10-US | 25 | 42 |
| SG132-100-US | 21 | 34 |

Each sample was placed on a zero background holder and placed in a Phillips PW1800 diffractometer using Cu radiation. Scans were then run over the range of 5° to 50° with a step size of 0.05° and a counting time of 2 hours each.

Once the diffraction patterns were obtained, the phases were identified with the aid of the Powder Diffraction File published by the International Centre for Diffraction Data. In all samples the crystalline phase identified was cellulose—Ia, which has a triclinic structure.

The distinguishing feature among the 20 samples is the peak breadth, which is related to the crystallite domain size. The experimental peak breadth was used to compute the domain size and percent crystallinity, which are reported in Table 4.

Percent crystallinity ($X_c\%$) is measured as a ratio of the crystalline area to the total area under the x-ray diffraction peaks, $$X_c\% = \frac{A_C}{\{A_a + A_C\}} \times 100\%$$

where,
$A_c$=Area of crystalline phase
$A_a$=Area of amorphous phase
$X_c$=Percent of crystallinity To determine the percent crystallinity for each sample it was necessary to first extract the amount of the amorphous phase. This is done by estimating the area of each diffraction pattern that can be attributed to the crystalline phase (represented by the sharper peaks) and the non-crystalline phase (represented by the broad humps beneath the pattern and centered at 22° and 38°).

A systematic process was used to minimize error in these calculations due to broad crystalline peaks as well as high background intensity. First, a linear background was applied and then removed. Second, two Gaussian peaks centered at 22° and 38° with widths of 10-12° each were fitted to the humps beneath the crystalline peaks. Third, the area beneath the two broad Gaussian peaks and the rest of the pattern were determined. Finally, percent crystallinity was calculated by dividing the area beneath the crystalline peak by the total intensity (after background subtraction). Domain size and % crystallinity of the samples as determined by X-ray diffraction (XRD) are presented in Table 4.

Example 11

Porosimetry Analysis of Irradiated Materials

Mercury pore size and pore volume analysis (Table 5) is based on forcing mercury (a non-wetting liquid) into a porous structure under tightly controlled pressures. Since mercury does not wet most substances and will not spontaneously penetrate pores by capillary action, it must be forced into the voids of the sample by applying external pressure. The pressure required to fill the voids is inversely proportional to the size of the pores. Only a small amount of force or pressure is required to fill large voids, whereas much greater pressure is required to fill voids of very small pores.

TABLE 5

Pore Size and Volume Distribution by Mercury Porosimetry

| Sample ID | Total Intrusion Volume (mL/g) | Total Pore Area (m²/g) | Median Pore Diameter (Volume) (μm) | Median Pore Diameter (Area) (μm) | Average Pore Diameter (4 V/A) (μm) | Bulk Density @ 0.50 psia (g/mL) | Apparent (skeletal) Density (g/mL) | Porosity (%) |
|---|---|---|---|---|---|---|---|---|
| P132 | 6.0594 | 1.228 | 36.2250 | 13.7278 | 19.7415 | 0.1448 | 1.1785 | 87.7163 |
| P132-10 | 5.5436 | 1.211 | 46.3463 | 4.5646 | 18.3106 | 0.1614 | 1.5355 | 89.4875 |
| P132-100 | 5.3985 | 0.998 | 34.5235 | 18.2005 | 21.6422 | 0.1612 | 1.2413 | 87.0151 |

TABLE 5-continued

Pore Size and Volume Distribution by Mercury Porosimetry

| Sample ID | Total Intrusion Volume (mL/g) | Total Pore Area (m²/g) | Median Pore Diameter (Volume) (μm) | Median Pore Diameter (Area) (μm) | Average Pore Diameter (4 V/A) (μm) | Bulk Density @ 0.50 psia (g/mL) | Apparent (skeletal) Density (g/mL) | Porosity (%) |
|---|---|---|---|---|---|---|---|---|
| P132-181 | 3.2866 | 0.868 | 25.3448 | 12.2410 | 15.1509 | 0.2497 | 1.3916 | 82.0577 |
| P132-US | 6.0005 | 14.787 | 98.3459 | 0.0055 | 1.6231 | 0.1404 | 0.8894 | 84.2199 |
| A132 | 2.0037 | 11.759 | 64.6308 | 0.0113 | 0.6816 | 0.3683 | 1.4058 | 73.7990 |
| A132-10 | 1.9514 | 10.326 | 53.2706 | 0.0105 | 0.7560 | 0.3768 | 1.4231 | 73.5241 |
| A132-100 | 1.9394 | 10.205 | 43.8966 | 0.0118 | 0.7602 | 0.3760 | 1.3889 | 72.9264 |
| SG132 | 2.5267 | 8.265 | 57.6958 | 0.0141 | 1.2229 | 0.3119 | 1.4708 | 78.7961 |
| SG132-10 | 2.1414 | 8.643 | 26.4666 | 0.0103 | 0.9910 | 0.3457 | 1.3315 | 74.0340 |
| SG132-100 | 2.5142 | 10.766 | 32.7118 | 0.0098 | 0.9342 | 0.3077 | 1.3590 | 77.3593 |
| SG132-10-US | 4.4043 | 1.722 | 71.5734 | 1.1016 | 10.2319 | 0.1930 | 1.2883 | 85.0169 |
| SG132-100-US | 4.9665 | 7.358 | 24.8462 | 0.0089 | 2.6998 | 0.1695 | 1.0731 | 84.2010 |
| WS132 | 2.9920 | 5.447 | 76.3675 | 0.0516 | 2.1971 | 0.2773 | 1.6279 | 82.9664 |
| WS132-10 | 3.1138 | 2.901 | 57.4727 | 0.3630 | 4.2940 | 0.2763 | 1.9808 | 86.0484 |
| WS132-100 | 3.2077 | 3.114 | 52.3284 | 0.2876 | 4.1199 | 0.2599 | 1.5611 | 83.3538 |

The AutoPore 9520 can attain a maximum pressure of 414 MPa or 60,000 psia. There are four low-pressure stations for sample preparation and collection of macropore data from 0.2 psia to 50 psia. There are two high-pressure chambers, which collect data from 25 psia to 60,000 psia. The sample is placed in a bowl-like apparatus called a penetrometer, which is bonded to a glass capillary stem with a metal coating. As mercury invades the voids in and around the sample, it moves down the capillary stem. The loss of mercury from the capillary stem results in a change in the electrical capacitance. The change in capacitance during the experiment is converted to volume of mercury by knowing the stem volume of the penetrometer in use. A variety of penetrometers with different bowl (sample) sizes and capillaries are available to accommodate most sample sizes and configurations. Table 6 below defines some of the key parameters calculated for each sample.

TABLE 6

Definition of Parameters

| Parameter | Description |
|---|---|
| Total Intrusion Volume: | The total volume of mercury intruded during an experiment. This can include interstitial filling between small particles, porosity of sample, and compression volume of sample. |
| Total Pore Area: | The total intrusion volume converted to an area assuming cylindrical shaped pores. |
| Median Pore Diameter (volume): | The size at the 50$^{th}$ percentile on the cumulative volume graph. |
| Median Pore Diameter (area): | The size at the 50$^{th}$ percentile on the cumulative area graph. |
| Average Pore Diameter: | The total pore volume divided by the total pore area (4 V/A). |
| Bulk Density: | The mass of the sample divided by the bulk volume. Bulk volume is determined at the filling pressure, typically 0.5 psia. |
| Apparent Density: | The mass of sample divided by the volume of sample measured at highest pressure, typically 60,000 psia. |
| Porosity: | (Bulk Density/Apparent Density) × 100% |

Example 12

Particle Size Analysis of Irradiated Materials

The technique of particle sizing by static light scattering is based on Mie theory (which also encompasses Fraunhofer theory). Mie theory predicts the intensity vs. angle relationship as a function of the size for spherical scattering particles provided that other system variables are known and held constant. These variables are the wavelength of incident light and the relative refractive index of the sample material. Application of Mie theory provides the detailed particle size information. Table 7 summarizes particle size using median diameter, mean diameter, and modal diameter as parameters.

TABLE 7

Particle Size by Laser Light Scattering (Dry Sample Dispersion)

| Sample ID | Median Diameter (μm) | Mean Diameter (μm) | Modal Diameter (μm) |
|---|---|---|---|
| A132 | 380.695 | 418.778 | 442.258 |
| A132-10 | 321.742 | 366.231 | 410.156 |
| A132-100 | 301.786 | 348.633 | 444.169 |
| SG132 | 369.400 | 411.790 | 455.508 |
| SG132-10 | 278.793 | 325.497 | 426.717 |
| SG132-100 | 242.757 | 298.686 | 390.097 |
| WS132 | 407.335 | 445.618 | 467.978 |
| WS132-10 | 194.237 | 226.604 | 297.941 |
| WS132-100 | 201.975 | 236.037 | 307.304 |

Particle size was determined by Laser Light Scattering (Dry Sample Dispersion) using a Malvern Mastersizer 2000 using the following conditions:
  Feed Rate: 35%
  Disperser Pressure: 4 Bar
  Optical Model: (2.610, 1.000 i), 1.000
An appropriate amount of sample was introduced onto a vibratory tray. The feed rate and air pressure were adjusted to ensure that the particles were properly dispersed. The key component is selecting an air pressure that will break up agglomerations, but does not compromise the sample integrity. The amount of sample needed varies depending on the size of the particles. In general, samples with fine particles require less material than samples with coarse particles.

Example 13

Surface Area Analysis of Irradiated Materials

Table 8. Summary of Surface Area by Gas Adsorption
  Surface area of each sample was analyzed using a Micromeritics ASAP 2420 Accelerated Surface Area and Porosimetry System. The samples were prepared by first degassing for 16 hours at 40° C. Next, free space (both warm and cold) with helium is calculated and then the sample tube is evacuated again to remove the helium. Data collection begins after this second evacuation and consists of defining target pressures, which controls how much gas is dosed onto the sample. At each target pressure, the quantity of gas adsorbed and the actual pressure are determined and recorded. The pressure inside the sample tube is measured with a pressure transducer. Additional doses of gas will continue until the target pressure is achieved and allowed to equilibrate. The quantity of gas adsorbed is determined by summing multiple doses onto the sample. The pressure and quantity define a gas adsorption isotherm and are used to calculate a number of parameters, including BET surface area (Table 8).

| Sample ID | Single point surface area (m$^2$/g) | | BET Surface Area (m$^2$/g) |
|---|---|---|---|
| P132 | @ P/Po = 0.250387771 | 1.5253 | 1.6897 |
| P132-10 | @ P/Po = 0.239496722 | 1.0212 | 1.2782 |
| P132-100 | @ P/Po = 0.240538100 | 1.0338 | 1.2622 |
| P132-181 | @ P/Po = 0.239166091 | 0.5102 | 0.6448 |
| P132-US | @ P/Po = 0.217359072 | 1.0983 | 1.6793 |
| A132 | @ P/Po = 0.240040610 | 0.5400 | 0.7614 |
| A132-10 | @ P/Po = 0.211218936 | 0.5383 | 0.7212 |
| A132-100 | @ P/Po = 0.238791097 | 0.4258 | 0.5538 |
| SG132 | @ P/Po = 0.237989353 | 0.6359 | 0.8350 |
| SG132-10 | @ P/Po = 0.238576905 | 0.6794 | 0.8689 |
| SG132-100 | @ P/Po = 0.241960361 | 0.5518 | 0.7034 |
| SG132-10-US | @ P/Po = 0.225692889 | 0.5693 | 0.7510 |
| SG132-100-US | @ P/Po = 0.225935246 | 1.0983 | 1.4963 |
| WS132 | @ P/Po = 0.237823664 | 0.6582 | 0.8663 |
| WS132-10 | @ P/Po = 0.238612476 | 0.6191 | 0.7912 |
| WS132-100 | @ P/Po = 0.238398832 | 0.6255 | 0.8143 |

The BET model for isotherms is a widely used theory for calculating the specific surface area. The analysis involves determining the monolayer capacity of the sample surface by calculating the amount required to cover the entire surface with a single densely packed layer of krypton. The monolayer capacity is multiplied by the cross sectional area of a molecule of probe gas to determine the total surface area. Specific surface area is the surface area of the sample aliquot divided by the mass of the sample.

Example 14

Fiber Length Determination of Irradiated Materials

Fiber length distribution testing was performed in triplicate on the samples submitted using the Techpap MorFi LB01 system. The average length and width are reported in Table 9.

TABLE 9

Summary of Lignocellulosic Fiber Length and Width Data

| Sample ID | Arithmetic Average (mm) | Average Length Weighted in Length (mm) | Statistically Corrected Average Length Weighted in Length (mm) | Width (micrometers) (μm) |
|---|---|---|---|---|
| P132-10 | 0.484 | 0.615 | 0.773 | 24.7 |
| P132-100 | 0.369 | 0.423 | 0.496 | 23.8 |
| P132-181 | 0.312 | 0.342 | 0.392 | 24.4 |
| A132-10 | 0.382 | 0.423 | 0.650 | 43.2 |
| A132-100 | 0.362 | 0.435 | 0.592 | 29.9 |
| SG132-10 | 0.328 | 0.363 | 0.521 | 44.0 |
| SG132-100 | 0.325 | 0.351 | 0.466 | 43.8 |

TABLE 9-continued

Summary of Lignocellulosic Fiber Length and Width Data

| Sample ID | Arithmetic Average (mm) | Average Length Weighted in Length (mm) | Statistically Corrected Average Length Weighted in Length (mm) | Width (micrometers) (μm) |
|---|---|---|---|---|
| WS132-10 | 0.353 | 0.381 | 0.565 | 44.7 |
| WS132-100 | 0.354 | 0.371 | 0.536 | 45.4 |

Example 15

Ultrasonic Treatment of Irradiated and Un-Irradiated Switchgrass

Switchgrass was sheared according to Example 4. The switchgrass was treated by ultrasound alone or irradiation with 10 Mrad or 100 Mrad of gamma rays, and then sonicated. The resulting materials correspond to G132-BR (un-irradiated), G132-10-BR (10 Mrad and sonication) and G132-100-BR (100 Mrad and sonication), as presented in Table 1. Sonication was performed on each sample for 30 minutes using 20 kHz ultrasound from a 1000 W horn under re-circulating conditions. Each sample was dispersed in water at a concentration of about 0.10 g/mL.

Figure 32:
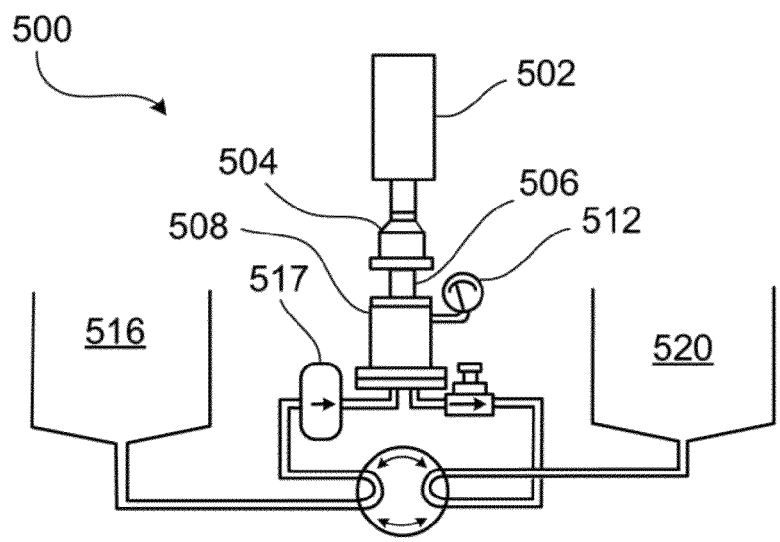
Figure 33:
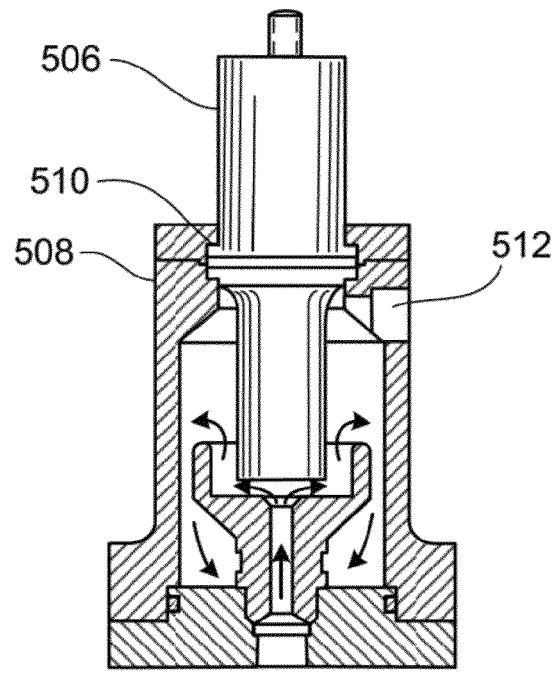
FIG. 33 is a cross-sectional view through the processing cell of FIG. 32.

FIGS. 32 and 33 show the apparatus used for sonication. Apparatus 500 includes a converter 502 connected to booster 504 communicating with a horn 506 fabricated from titanium or an alloy of titanium. The horn, which has a seal 510 made from VITON® about its perimeter on its processing side, forms a liquid tight seal with a processing cell 508. The processing side of the horn is immersed in a liquid, such as water, that has dispersed therein the sample to be sonicated. Pressure in the cell is monitored with a pressure gauge 512. In operation, each sample is moved by pump 517 from tank 516 through the processing cell and is sonicated. After, sonication, the sample is captured in tank 520. The process can be reversed in that the contents of tank 520 can be sent through the processing cell and captured in tank 516. This process can be repeated a number of times until a desired level of processing is delivered to the sample.

Example 16

Scanning Electron Micrographs of Un-Irradiated Switchgrass in Comparison to Irradiated and Irradiated and Sonicated Switchgrass Switchgrass samples for the scanning electron micrographs were applied to carbon tape and gold sputter coated (70 seconds). Images were taken with a JEOL 6500 field emission scanning electron microscope.

Figure 34:
FIG. 34 is a scanning electron micrograph at 1000× magnification of a fibrous material produced from shearing switchgrass on a rotary knife cutter, and then passing the sheared material through a 1/32 inch screen.

FIG. 34 is a scanning electron micrograph at 1000× magnification of a fibrous material produced from shearing switchgrass on a rotary knife cutter, and then passing the sheared material through a 1/32 inch screen.

Figure 35:
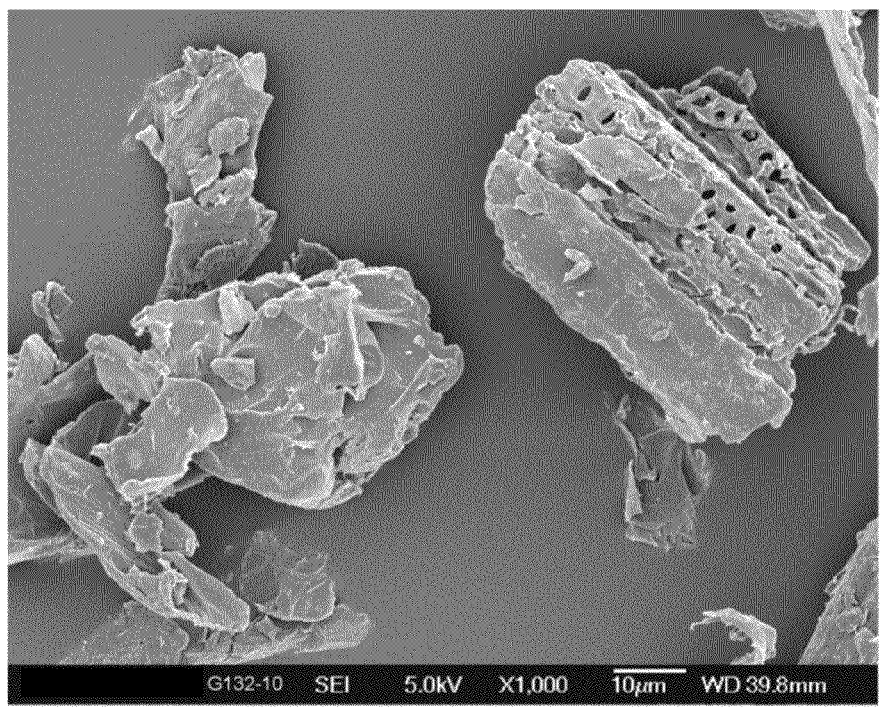
FIGS. 35 and 36 are scanning electron micrographs of the fibrous material of FIG. 34 after irradiation with 10 Mrad and 100 Mrad gamma rays, respectively, at 1000× magnification.
Figure 36:
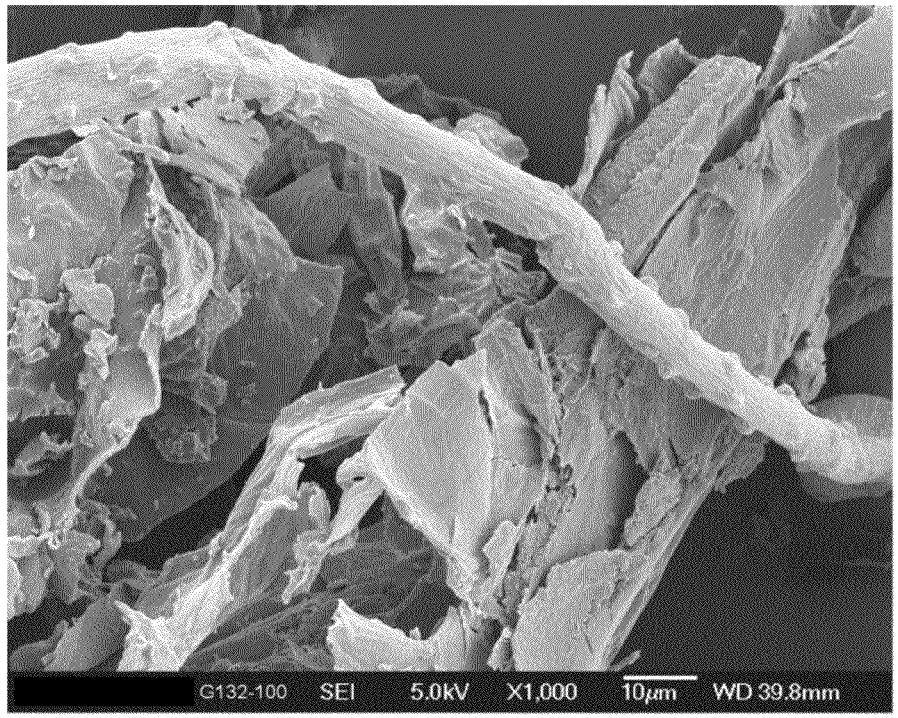

FIGS. 35 and 36 are scanning electron micrographs of the fibrous material of FIG. 34 after irradiation with 10 Mrad and 100 Mrad gamma rays, respectively, at 1000× magnification.

Figure 37:
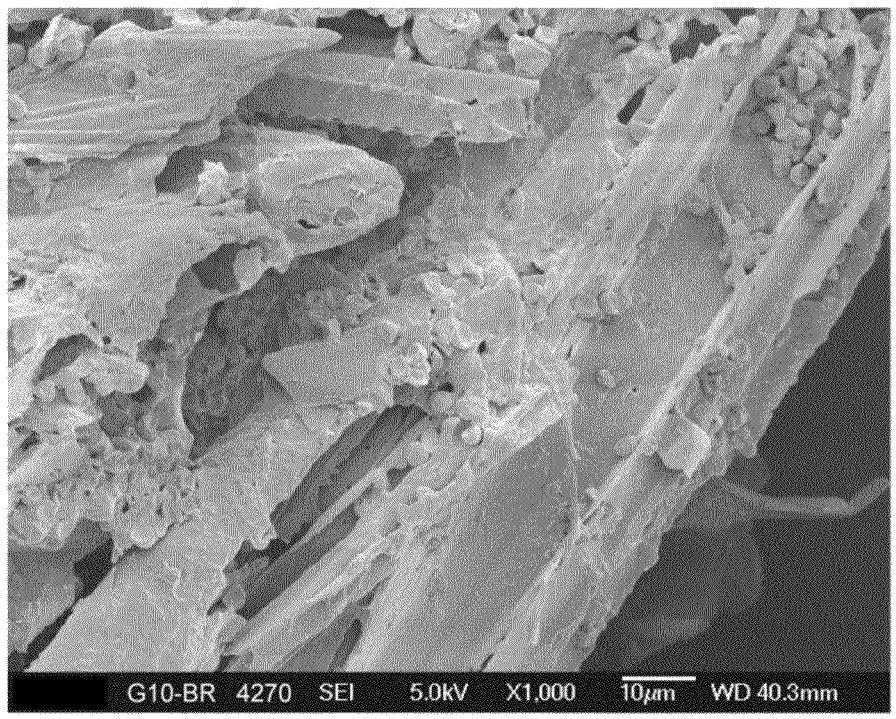
FIG. 37 is a scanning electron micrographs of the fibrous material of FIG. 34 after irradiation with 10 Mrad and sonication at 1000× magnification.

FIG. 37 is a scanning electron micrographs of the fibrous material of FIG. 34 after irradiation with 10 Mrad and sonication at 1000× magnification.

Figure 38:
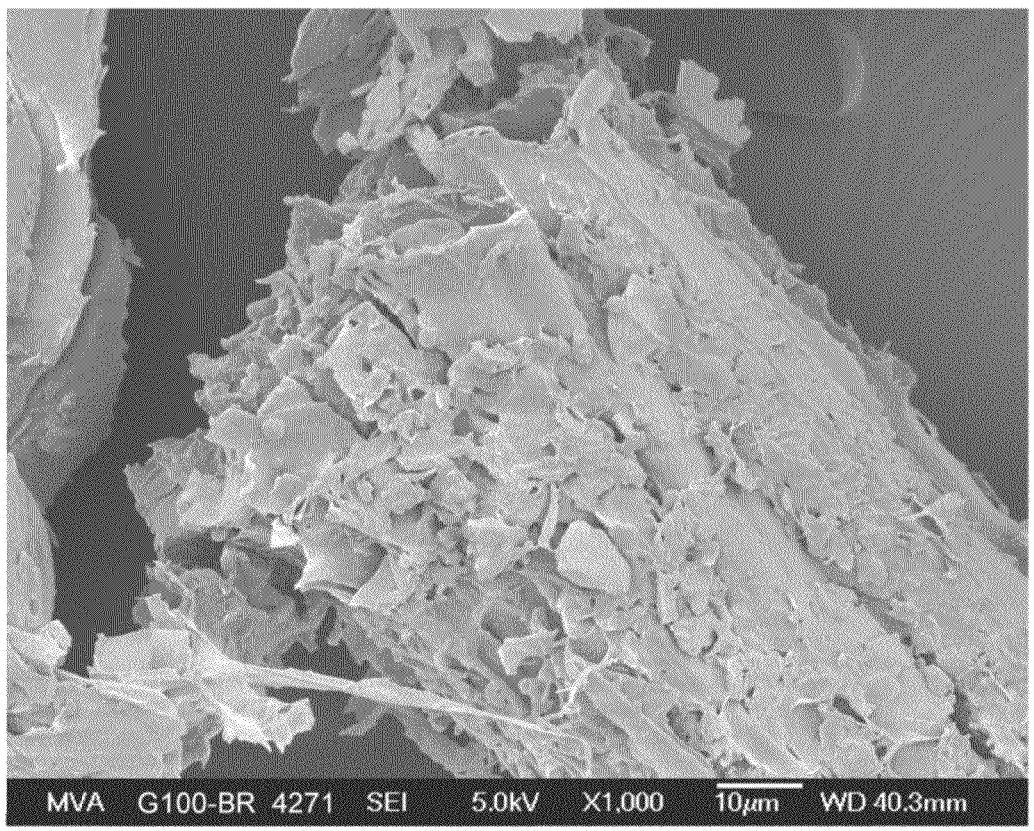
FIG. 38 is a scanning electron micrographs of the fibrous material of FIG. 34 after irradiation with 100 Mrad and sonication at 1000× magnification.

FIG. 38 is a scanning electron micrographs of the fibrous material of FIG. 34 after irradiation with 100 Mrad and sonication at 1000× magnification.

Example 17

Infrared Spectrum of Irradiated Kraft Paper in Comparison to Un-Irradiated Kraft Paper The FT-IR analysis was performed on a Nicolet/Impact 400. The results indicate that all samples reported in Table 1 are consistent with a cellulose-based material.

Figure 39:
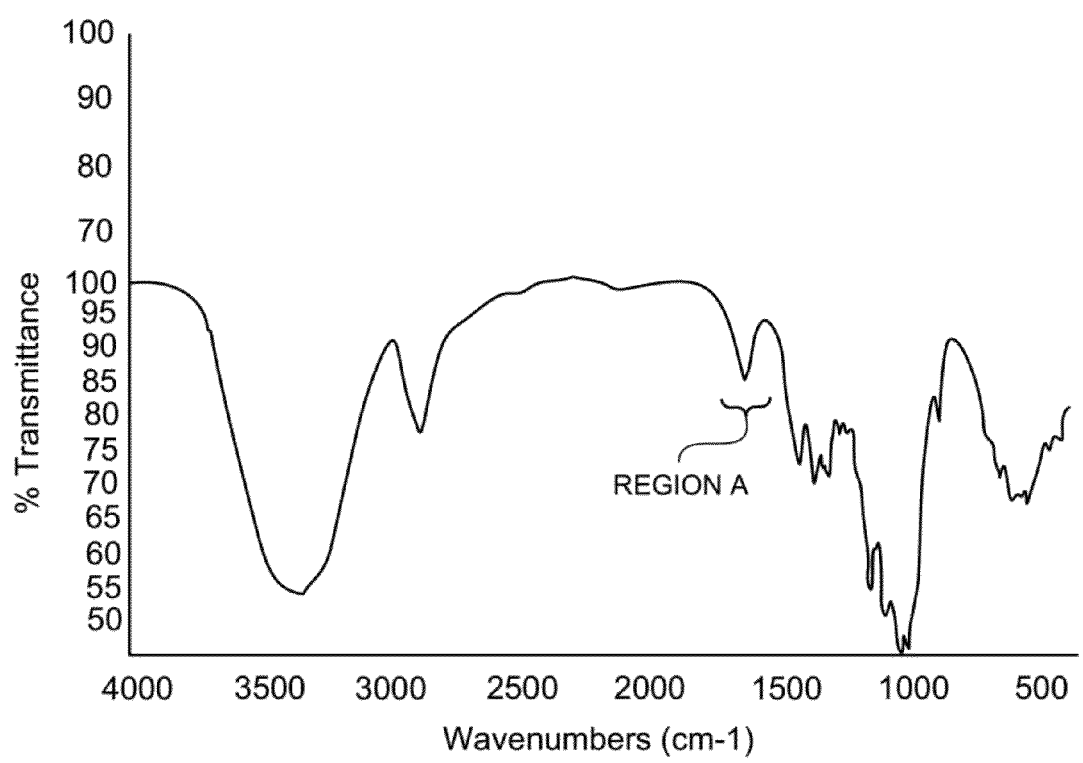
FIG. 39 is an infrared spectrum of Kraft board paper sheared on a rotary knife cutter.
Figure 40:
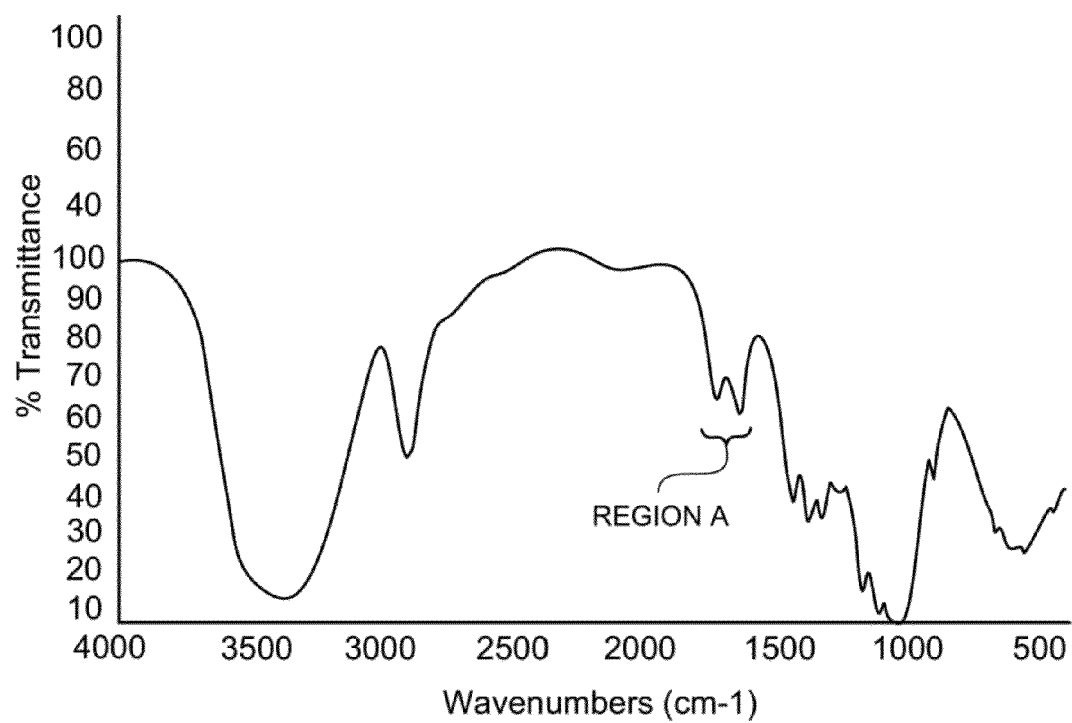
FIG. 40 is an infrared spectrum of the Kraft paper of FIG. 39 after irradiation with 100 Mrad of gamma radiation.

FIG. 39 is an infrared spectrum of Kraft board paper sheared according to Example 4, while FIG. 40 is an infrared spectrum of the Kraft paper of FIG. 39 after irradiation with 100 Mrad of gamma radiation. The irradiated sample shows an additional peak in region A (centered about 1730 cm$^{-1}$) that is not found in the un-irradiated material.

Example 18

Combination of Electron Beam and Sonication Pretreatment

Switchgrass is used as the feedstock and is sheared with a Munson rotary knife cutter into a fibrous material. The fibrous material is then evenly distributed onto an open tray composed of tin with an area of greater than about 500 in$^2$. The fibrous material is distributed so that it has a depth of about 1-2 inches in the open tray. The fibrous material may be distributed in plastic bags at lower doses of irradiation (under 10 MRad), and left uncovered on the metal tray at higher doses of radiation.

Separate samples of the fibrous material are then exposed to successive doses of electron beam radiation to achieve a total dose of 1 Mrad, 2 Mrad, 3, Mrad, 5 Mrad, 10 Mrad, 50 Mrad, and 100 Mrad. Some samples are maintained under the same conditions as the remaining samples, but are not irradiated, to serve as controls. After cooling, the irradiated fibrous material is sent on for further processing through a sonication device.

The sonication device includes a converter connected to booster communicating with a horn fabricated from titanium or an alloy of titanium. The horn, which has a seal made from VITON® about its perimeter on its processing side, forms a liquid tight seal with a processing cell. The processing side of the horn is immersed in a liquid, such as water, into which the irradiated fibrous material to be sonicated is immersed. Pressure in the cell is monitored with a pressure gauge. In operation, each sample is moved by pump through the processing cell and is sonicated.

To prepare the irradiated fibrous material for sonication, the irradiated fibrous material is removed from any container (e.g., plastic bags) and is dispersed in water at a concentration of about 0.10 g/mL. Sonication is performed on each sample for 30 minutes using 20 kHz ultrasound from a 1000 W horn under re-circulating conditions. After sonication, the irradiated fibrous material is captured in a tank. This process can be repeated a number of times until a desired level of processing is achieved based on monitoring the structural changes in the switchgrass. Again, some irradiated samples are kept under the same conditions as the remaining samples, but are not sonicated, to serve as controls. In addition, some samples that were not irradiated are sonicated, again to serve as controls. Thus, some controls are not processed, some are only irradiated, and some are only sonicated.

Example 19

Microbial Testing of Pretreated Biomass

Specific lignocellulosic materials pretreated as described herein are analyzed for toxicity to common strains of yeast and bacteria used in the biofuel industry for the fermentation step in ethanol production. Additionally, sugar content and compatibility with cellulase enzymes are examined to determine the viability of the treatment process. Testing of the pretreated materials is carried out in two phases as follows.

I. Toxicity and Sugar Content

Toxicity of the pretreated grasses and paper feedstocks is measured in yeast *Saccharomyces cerevisiae* (wine yeast) and *Pichia stipitis* (ATCC 66278) as well as the bacteria *Zymomonas mobilis* (ATCC 31821) and *Clostridium thermocellum* (ATCC 31924). A growth study is performed with each of the organisms to determine the optimal time of incubation and sampling.

Each of the feedstocks is then incubated, in duplicate, with *S. cerevisiae, P. stipitis, Z. mobilis*, and *C. thermocellum* in a standard microbiological medium for each organism. YM broth is used for the two yeast strains, *S. cerevisiae* and *P. stipitis*. RM medium is used for *Z. mobilis* and CM4 medium for *C. thermocellum*. A positive control, with pure sugar added, but no feedstock, is used for comparison. During the incubation, a total of five samples is taken over a 12 hour period at time 0, 3, 6, 9, and 12 hours and analyzed for viability (plate counts for *Z. mobilis* and direct counts for *S. cerevisiae*) and ethanol concentration.

Sugar content of the feedstocks is measured using High Performance Liquid Chromatography (HPLC) equipped with either a Shodex® sugar SP0810 or Biorad Aminex® HPX-87P column. Each of the feedstocks (approx. 5 g) is mixed with reverse osmosis (RO) water for 1 hour. The liquid portion of the mixture is removed and analyzed for glucose, galactose, xylose, mannose, arabinose, and cellobiose content. The analysis is performed according to National Bioenergy Center protocol Determination of Structural Carbohydrates and Lignin in Biomass.

II. Cellulase Compatibility

Feedstocks are tested, in duplicate, with commercially available Accellerase® 1000 enzyme complex, which contains a complex of enzymes that reduces lignocellulosic biomass into fermentable sugars, at the recommended temperature and concentration in an Erlenmeyer flask. The flasks are incubated with moderate shaking at around 200 rpm for 12 hours. During that time, samples are taken every three hours at time 0, 3, 6, 9, and 12 hours to determine the concentration of reducing sugars (Hope and Dean, Biotech J., 1974, 144: 403) in the liquid portion of the flasks.

Example 20

Alcohol Production Using Irradiation-Sonication Pretreatment

The optimum size for biomass conversion plants is affected by factors including economies of scale and the type and availability of biomass used as feedstock. Increasing plant size tends to increase economies of scale associated with plant processes. However, increasing plant size also tends to increase the costs (e.g., transportation costs) per unit of biomass feedstock. Studies analyzing these factors suggest that the appropriate size for biomass conversion plants can range from 2000 to 10,000 dried tons of biomass feedstock per day. The plant described below is sized to process 2000 tons of dry biomass feedstock per day.

Figure 41:
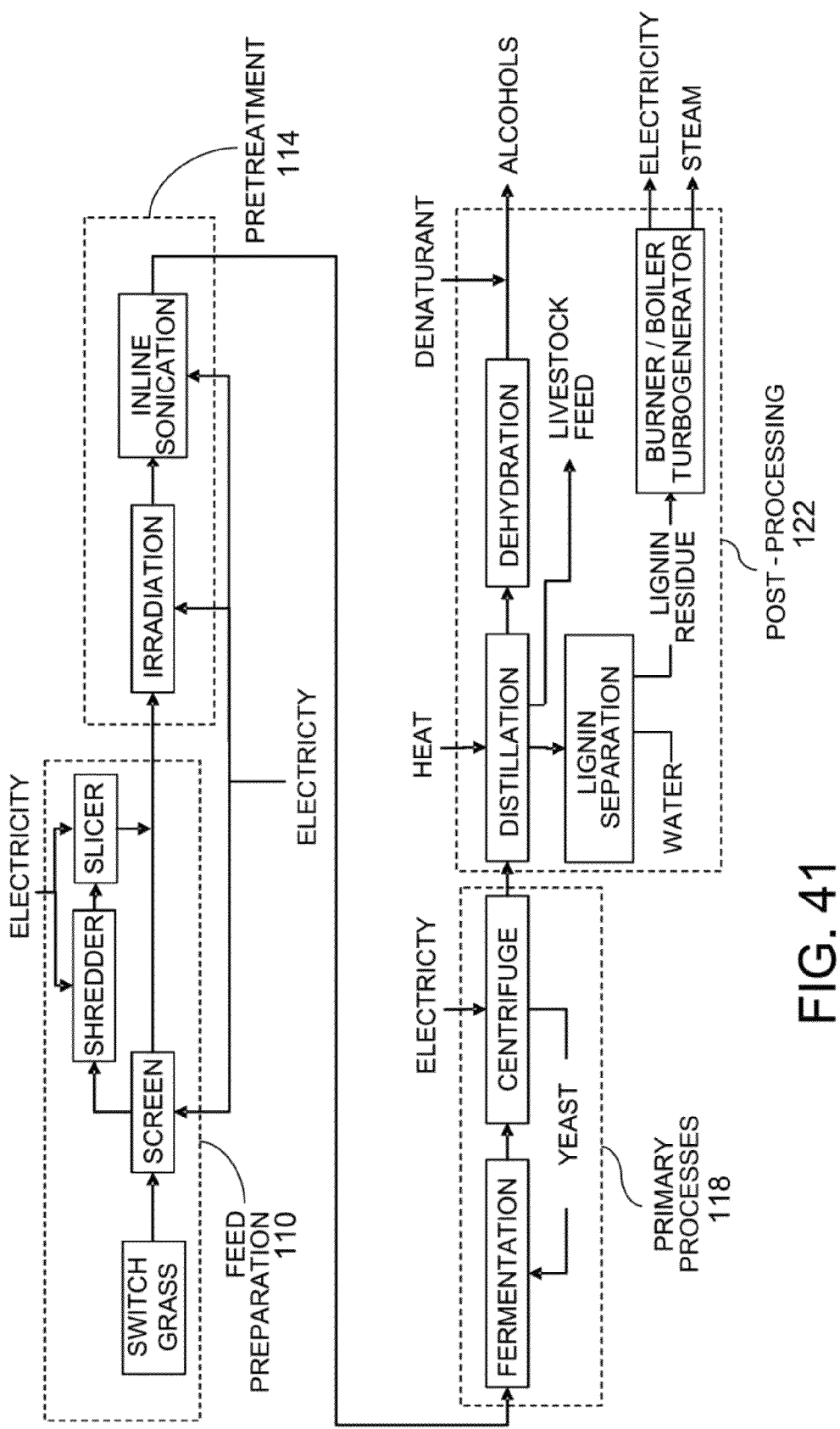
FIG. 41 is a schematic view of a process for biomass conversion.

FIG. 41 shows a process schematic of a biomass conversion system configured to process switchgrass. The feed preparation subsystem processes raw biomass feedstock to remove foreign objects and provide consistently sized particles for further processing. The pretreatment subsystem changes the molecular structure (e.g., reduces the average molecular weight and the crystallinity) of the biomass feedstock by irradiating the biomass feedstock, mixing the irradiated the biomass feedstock with water to form a slurry, and applying ultrasonic energy to the slurry. The irradiation and sonication convert the cellulosic and lignocellulosic components of the biomass feedstock into fermentable materials. The primary process subsystem ferments the glucose and other low weight sugars present after pretreatment to form alcohols.

Example 21

Electron Beam Processing of Table Sugar (Sucrose)

Sucrose was treated with a beam of electrons using a vaulted Rhodotron® TT200 continuous wave accelerator delivering 5 MeV electrons at 80 kW output power. The table below describes the nominal parameters for the TT200. The nominal doses (in MRad) and actual doses (in kgy) delivered to the samples are also given below.

| Rhodotron ® TT 200 Parameters | |
|---|---|
| Beam | |
| Beam Produced: | Accelerated electrons |
| Beam energy: | Nominal (maximum): 10 MeV (+0 keV-250 keV) |
| Energy dispersion at 10 Mev: | Full width half maximum (FWHM) 300 keV |
| Beam power at 10 MeV: | Guaranteed Operating Range 1 to 80 kW |
| Power Consumption | |
| Stand-by condition (vacuum and cooling ON): | <15 kW |
| At 50 kW beam power: | <210 kW |
| At 80 kW beam power: | <260 kW |
| RF System | |
| Frequency: | 107.5 ± 1 MHz |
| Tetrode type: | Thomson TH781 |
| Scanning Horn | |
| Nominal Scanning Length (measured at 25-35 cm from window): | 120 cm |
| Scanning Range: | From 30% to 100% of Nominal Scanning Length |
| Nominal Scanning Frequency (at max. scanning length): | 100 Hz ± 5% |
| Scanning Uniformity (across 90% of Nominal Scanning Length) | ±5% |

| Dosages Delivered to the Sucrose Samples | |
|---|---|
| Total Dosage (MRad) (Number Associated with Sample ID) | Delivered Dose (kgy)[1] |
| 1 | 9.9 |
| 3 | 29.0 |
| 5 | 50.4 |
| 7 | 69.2 |
| 10 | 100.0 |
| 15 | 150.3 |
| 20 | 198.3 |
| 30 | 330.9 |
| 50 | 529.0 |
| 70 | 695.9 |
| 100 | 993.6 |

[1]For example, 9.9 kgy was delivered in 11 seconds at a beam current of 5 mA and a line speed of 12.9 feet/minute. Cool time between 1 MRad treatments was about 2 minutes.

The solubility of the sucrose samples treated above 30 Mrad was enhanced, and at or above 30 Mrad, the sucrose appeared visually to be devoid of crystallinity. Above 70 Mrad, the sucrose was converted into a solid mass of material.

Feed Preparation

The selected design feed rate for the plant is 2,000 dry tons per day of switchgrass biomass. The design feed is chopped and/or sheared switchgrass.

Biomass feedstock, in the form of bales of switchgrass, is received by the plant on truck trailers. As the trucks are received, they are weighed and unloaded by forklifts. Some bales are sent to on-site storage while others are taken directly to the conveyors. From there, the bales are conveyed to an automatic unwrapping system that cuts away the plastic wrapping and/or net surrounding the bales. The biomass feedstock is then conveyed past a magnetic separator to remove tramp metal, after which it is introduced to shredder-shearer trains where the material is reduced in size. Finally, the biomass feedstock is conveyed to the pretreatment subsystem.

In some cases, the switchgrass bales are wrapped with plastic net to ensure they don't break apart when handled, and may also be wrapped in plastic film to protect the bale from weather. The bales are either square or round. The bales are received at the plant from off-site storage on large truck trailers.

Since switchgrass is only seasonally available, long-term storage is required to provide feed to the plant year-round. Long-term storage will likely consist of 400-500 acres of uncovered piled rows of bales at a location (or multiple locations) reasonably close to the ethanol plant. On-site short-term storage is provided equivalent to 72 hours of production at an outside storage area. Bales and surrounding access ways as well as the transport conveyors will be on a concrete slab. A concrete slab is used because of the volume of traffic required to deliver the large amount of biomass feedstock required. A concrete slab will minimize the amount of standing water in the storage area, as well as reduce the biomass feedstock's exposure to dirt. The stored material provides a short-term supply for weekends, holidays, and when normal direct delivery of material into the process is interrupted.

The bales are off-loaded by forklifts and are placed directly onto bale transport conveyors or in the short-term storage area. Bales are also reclaimed from short-term storage by forklifts and loaded onto the bale transport conveyors.

Bales travel to one of two bale unwrapping stations. Unwrapped bales are broken up using a spreader bar and then discharged onto a conveyor that passes a magnetic separator to remove metal prior to shredding. A tramp iron magnet is provided to catch stray magnetic metal and a scalping screen removes gross oversize and foreign material ahead of multiple shredder-shearer trains, which reduce the biomass feedstock to the proper size for pretreatment. The shredder-shearer trains include shredders and rotary knife cutters. The shredders reduce the size of the raw biomass feedstock and feed the resulting material to the rotary knife cutters. The rotary knife cutters concurrently shear the biomass feedstock and screen the resulting material.

Three storage silos are provided to limit overall system downtime due to required maintenance on and/or breakdowns of feed preparation subsystem equipment. Each silo can hold approximately 55,000 cubic feet of biomass feedstock (~3 hours of plant operation).

Pretreatment

Figure 42:
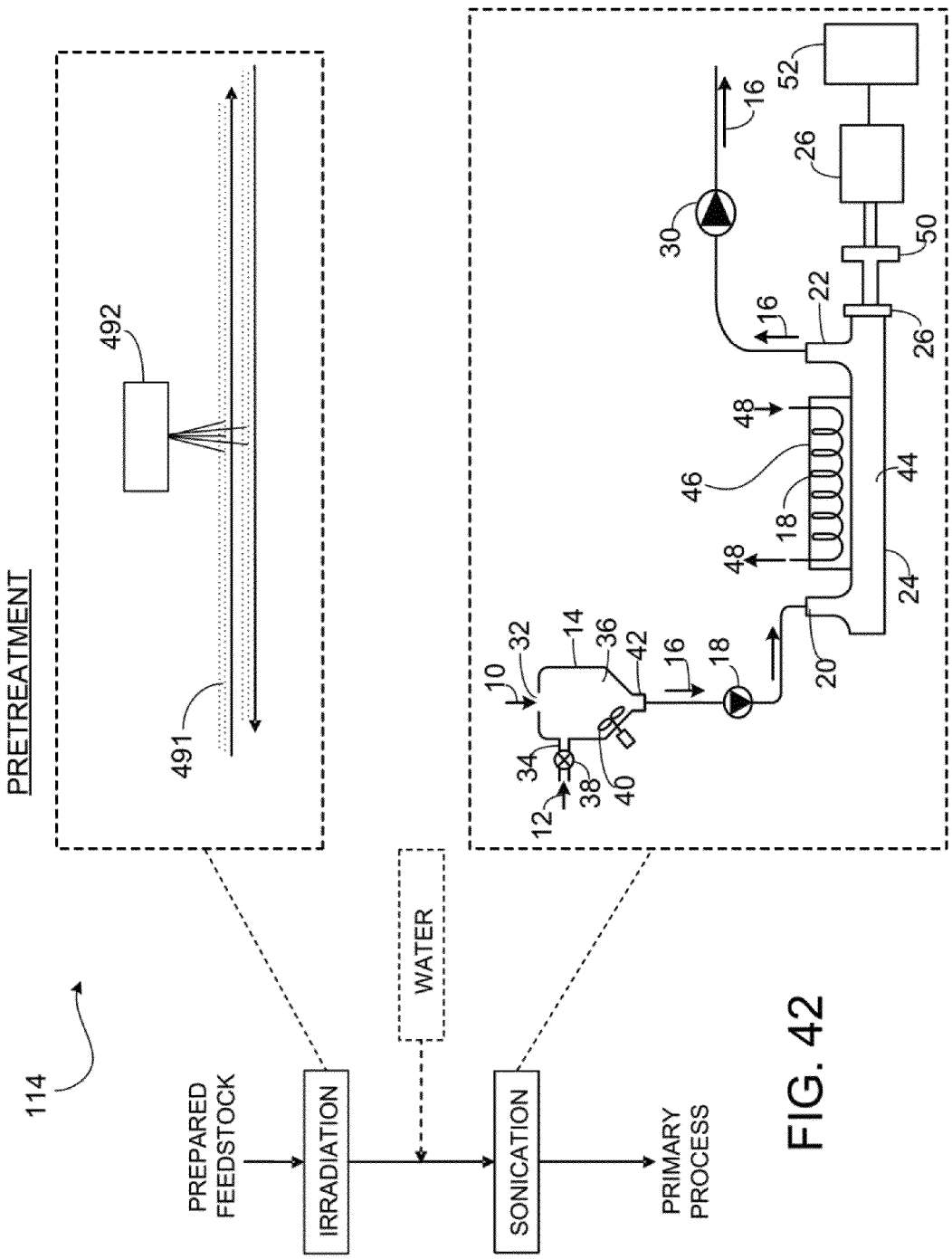
FIG. 42 is schematic view of another process for biomass conversion.

A conveyor belt carries the biomass feedstock from the feed preparation subsystem 110 to the pretreatment subsystem 114. As shown in FIG. 42, in the pretreatment subsystem 114, the biomass feedstock is irradiated using electron beam emitters, mixed with water to form a slurry, and subjected to the application of ultrasonic energy. As discussed above, irradiation of the biomass feedstock changes the molecular structure (e.g., reduces the average molecular weight and the crystallinity) of the biomass feedstock. Mixing the irradiated biomass feedstock into a slurry and applying ultrasonic energy to the slurry further changes the molecular structure of the biomass feedstock. Application of the radiation and sonication in sequence may have synergistic effects in that the combination of techniques appears to achieve greater changes to the molecular structure (e.g., reduces the average molecular weight and the crystallinity) than either technique can efficiently achieve on its own. Without wishing to be bound by theory, in addition to reducing the polymerization of the biomass feedstock by breaking intramolecular bonds between segments of cellulosic and lignocellulosic components of the biomass feedstock, the irradiation may make the overall physical structure of the biomass feedstock more brittle. After the brittle biomass feedstock is mixed into a slurry, the application of ultrasonic energy further changes the molecular structure (e.g., reduces the average molecular weight and the crystallinity) and also can reduce the size of biomass feedstock particles.

Electron Beam Irradiation

The conveyor belt 491 carrying the biomass feedstock into the pretreatment subsystem distributes the biomass feedstock into multiple feed streams (e.g., 50 feed streams) each leading to separate electron beam emitters 492. In this embodiment, the biomass feedstock is irradiated while it is dry. Each feed stream is carried on a separate conveyor belt to an associated electron beam emitter. Each irradiation feed conveyor belt can be approximately one meter wide. Before reaching the electron beam emitter, a localized vibration is induced in each conveyor belt to evenly distribute the dry biomass feedstock over the cross-sectional width of the conveyor belt.

Electron beam emitter 492 (e.g., electron beam irradiation devices commercially available from Titan Corporation, San Diego, Calif.) are configured to apply a 100 kilo-Gray dose of electrons applied at a power of 300 kW. The electron beam emitters are scanning beam devices with a sweep width of 1 meter to correspond to the width of the conveyor belt. In some embodiments, electron beam emitters with large, fixed beam widths are used. Factors including belt/beam width, desired dose, biomass feedstock density, and power applied govern the number of electron beam emitters required for the plant to process 2,000 tons per day of dry feed.

Sonication

The irradiated biomass feedstock is mixed with water to form a slurry before ultrasonic energy is applied. There can be a separate sonication system associated with each electron beam feed stream or several electron beam streams can be aggregated as feed for a single sonication system.

In each sonication system, the irradiated biomass feedstock is fed into a reservoir 1214 through a first intake 1232 and water is fed into the reservoir 1214 through second intake 1234. Appropriate valves (manual or automated) control the flow of biomass feedstock and the flow of water to produce a desired ratio of biomass feedstock to water (e.g., 10% cellulosic material, weight by volume). Each reservoir 1214 includes a mixer 1240 to agitate the contents of volume 1236 and disperse biomass feedstock throughout the water.

In each sonication system, the slurry is pumped (e.g., using a recessed impeller vortex pump 1218) from reservoir 1214 to and through a flow cell 1224 including an ultrasonic transducer 1226. In some embodiments, pump 1218 is configured to agitate the slurry 1216 such that the mixture of biomass feedstock and water is substantially uniform at inlet 1220 of the flow cell 1224. For example, the pump 1218 can agitate the slurry 1216 to create a turbulent flow that persists throughout the piping between the first pump and inlet 1220 of flow cell 1224.

Within the flow cell 1224, ultrasonic transducer 1226 transmits ultrasonic energy into slurry 1216 as the slurry flows through flow cell 1224. Ultrasonic transducer 1226 converts electrical energy into high frequency mechanical energy (e.g., ultrasonic energy), which is then delivered to the slurry through booster 48. Ultrasonic transducers are commercially available (e.g., from Hielscher USA, Inc. of Ringwood, N.J.) that are capable of delivering a continuous power of 16 kilowatts.

The ultrasonic energy traveling through booster 1248 in reactor volume 1244 creates a series of compressions and rarefactions in process stream 1216 with an intensity sufficient to create cavitation in process stream 1216. Cavitation disaggregates components of the biomass feedstock including, for example, cellulosic and lignocellulosic material dispersed in process stream 1216 (e.g., slurry). Cavitation also produces free radicals in the water of process stream 1216 (e.g., slurry). These free radicals act to further break down the cellulosic material in process stream 1216. In general, about 250 $MJ/m^3$ of ultrasonic energy is applied to process stream 1216 containing fragments of poplar chips. Other levels of ultrasonic energy (between about 5 and about 4000 $MJ/m^3$, e.g., 10, 25, 50, 100, 250, 500, 750, 1000, 2000, or 3000) can be applied to other biomass feedstocks After exposure to ultrasonic energy in reactor volume 1244, process stream 1216 exits flow cell 24 through outlet 1222.

Flow cell 1224 also includes a heat exchanger 1246 in thermal communication with at least a portion of reactor volume 1244. Cooling fluid 1248 (e.g., water) flows into heat exchanger 1246 and absorbs heat generated when process stream 1216 (e.g., slurry) is sonicated in reactor volume 1244. In some embodiments, the flow of cooling fluid 1248 into heat exchanger 1246 is controlled to maintain an approximately constant temperature in reactor volume 1244. In addition or in the alternative, the temperature of cooling fluid 1248 flowing into heat exchanger 1246 is controlled to maintain an approximately constant temperature in reactor volume 1244.

The outlet 1242 of flow cell 1224 is arranged near the bottom of reservoir 1214 to induce a gravity feed of process stream 1216 (e.g., slurry) out of reservoir 1214 towards the inlet of a second pump 1230 which pumps process stream 1216 (e.g., slurry) towards the primary process subsystem.

Sonication systems can include a single flow path (as described above) or multiple parallel flow paths each with an associated individual sonication unit. Multiple sonication units can also be arranged to series to increase the amount of sonic energy applied to the slurry.

Primary Processes

A vacuum rotary drum type filter removes solids from the slurry before fermentation. Liquid from the filter is pumped cooled prior to entering the fermentors. Filtered solids are passed to the post-processing subsystem for further processing.

The fermentation tanks are large, low pressure, stainless steel vessels with conical bottoms and slow speed agitators. Multiple first stage fermentation tanks can be arranged in series. The temperature in the first stage fermentation tanks is controlled to 30 degrees centigrade using external heat exchangers. Yeast is added to the first stage fermentation tank at the head of each series of tanks and carries through to the other tanks in the series.

Second stage fermentation consists of two continuous fermentors in series. Both fermentors are continuously agitated with slow speed mechanical mixers. Temperature is controlled with chilled water in external exchangers with continuous recirculation. Recirculation pumps are of the progressive cavity type because of the high solids concentration.

Off gas from the fermentation tanks and fermentors is combined and washed in a counter-current water column before being vented to the atmosphere. The off gas is washed to recover ethanol rather than for air emissions control.

Post-Processing
Distillation

Distillation and molecular sieve adsorption are used to recover ethanol from the raw fermentation beer and produce 99.5% ethanol. Distillation is accomplished in two columns—the first, called the beer column, removes the dissolved CO2 and most of the water, and the second concentrates the ethanol to a near azeotropic composition.

All the water from the nearly azeotropic mixture is removed by vapor phase molecular sieve adsorption. Regeneration of the adsorption columns requires that an ethanol water mixture be recycled to distillation for recovery.

Fermentation vents (containing mostly CO2, but also some ethanol) as well as the beer column vent are scrubbed in a water scrubber, recovering nearly all of the ethanol. The scrubber effluent is fed to the first distillation column along with the fermentation beer.

The bottoms from the first distillation contain all the unconverted insoluble and dissolved solids. The insoluble solids are dewatered by a pressure filter and sent to a combustor. The liquid from the pressure filter that is not recycled is concentrated in a multiple effect evaporator using waste heat from the distillation. The concentrated syrup from the evaporator is mixed with the solids being sent to the combustor, and the evaporated condensate is used as relatively clean recycle water to the process.

Because the amount of stillage water that can be recycled is limited, an evaporator is included in the process. The total amount of the water from the pressure filter that is directly recycled is set at 25%. Organic salts like ammonium acetate or lactate, steep liquor components not utilized by the organism, or inorganic compounds in the biomass end up in this stream. Recycling too much of this material can result in levels of ionic strength and osmotic pressures that can be detrimental to the fermenting organism's efficiency. For the water that is not recycled, the evaporator concentrates the dissolved solids into a syrup that can be sent to the combustor, minimizing the load to wastewater treatment.

Wastewater Treatment

The wastewater treatment section treats process water for reuse to reduce plant makeup water requirements. Wastewater is initially screened to remove large particles, which are collected in a hopper and sent to a landfill. Screening is followed by anaerobic digestion and aerobic digestion to digest organic matter in the stream. Anaerobic digestion produces a biogas stream that is rich in methane that is fed to the combustor. Aerobic digestion produces a relatively clean water stream for reuse in the process as well as a sludge that is primarily composed of cell mass. The sludge is also burned in the combustor. This screening/anaerobic digestion/aerobic digestion scheme is standard within the current ethanol industry and facilities in the 1-5 million gallons per day range can be obtained as "off-the-shelf" units from vendors.

Combustor, Boiler, and Turbogenerator

The purpose of the combustor, boiler, and turbogenerator subsystem is to burn various by-product streams for steam and electricity generation. For example, some lignin, cellulose, and hemicellulose remains unconverted through the pretreatment and primary processes. The majority of wastewater from the process is concentrated to a syrup high in soluble solids. Anaerobic digestion of the remaining wastewater produces a biogas high in methane. Aerobic digestion produces a small amount of waste biomass (sludge). Burning these by-product streams to generate steam and electricity allows the plant to be self-sufficient in energy, reduces solid waste disposal costs, and generates additional revenue through sales of excess electricity.

Three primary fuel streams (post-distillate solids, biogas, and evaporator syrup) are fed to a circulating fluidized bed combustor. The small amount of waste biomass (sludge) from wastewater treatment is also sent to the combustor. A fan moves air into the combustion chamber. Treated water enters the heat exchanger circuit in the combustor and is evaporated and superheated to 510° C. (950° F.) and 86 atm (1265 psia) steam. Flue gas from the combustor preheats the entering combustion air then enters a baghouse to remove particulates, which are landfilled. The gas is exhausted through a stack.

A multistage turbine and generator are used to generate electricity. Steam is extracted from the turbine at three different conditions for injection into the pretreatment reactor and heat exchange in distillation and evaporation. The remaining steam is condensed with cooling water and returned to the boiler feedwater system along with condensate from the various heat exchangers in the process. Treated well water is used as makeup to replace steam used in direct injection.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

The invention claimed is:

1. A method comprising:
applying a first dose of ionizing radiation to a flowing biomass,
mixing the biomass, and
applying a second dose of ionizing radiation to the biomass.

2. The method of claim 1 wherein the ionizing radiation comprises electron beam radiation.

3. The method of claim 1 wherein the biomass comprises a cellulosic or lignocellulosic material.

4. The method of claim 1 further comprising cooling the biomass between the first dose and second dose.

5. The method of claim 1 wherein the biomass is in particulate form.

6. The method of claim 1 further comprising, after applying the second dose, utilizing a microorganism and/or an enzyme to convert the biomass to a product.

7. The method of claim 6 wherein the product comprises a sugar.

8. The method of claim 6 wherein the utilizing step comprises saccharification.

9. The method of claim 6 wherein the utilizing step comprises fermentation.

10. A method comprising:
   applying a first dose of ionizing radiation to a flowing biomass on a vibratory conveyor,
   mixing the biomass, and
   applying a second dose of ionizing radiation to the biomass.

11. The method of claim 10 wherein the ionizing radiation comprises electron beam radiation.

12. The method of claim 10 wherein the biomass comprises a cellulosic or lignocellulosic material.

13. The method of claim 10 further comprising cooling the biomass between the first dose and second dose.

14. The method of claim 10 wherein the biomass is in particulate form.

15. The method of claim 10 further comprising, after applying the second dose, utilizing a microorganism and/or an enzyme to convert the biomass to a product.

16. The method of claim 15 wherein the product comprises a sugar.

17. The method of claim 15 wherein the utilizing step comprises saccharification.

18. The method of claim 15 wherein the utilizing step comprises fermentation.

* * * * *